US008367052B2

(12) United States Patent
Han et al.

(10) Patent No.: US 8,367,052 B2
(45) Date of Patent: Feb. 5, 2013

(54) METHODS FOR PROMOTING PROTECTION AND REGENERATION OF BONE MARROW USING CXCL9 AND ANTI-CXCL9 ANTIBODIES

(75) Inventors: Wei Han, Shanghai (CN); Huili Lu, Shanghai (CN)

(73) Assignee: General Regeneratives Holdings Inc., Grand Cayman (KY)

( * ) Notice: Subject to any disclaimer, the term of this patent is extended or adjusted under 35 U.S.C. 154(b) by 343 days.

(21) Appl. No.: 12/530,579

(22) PCT Filed: Mar. 26, 2007

(86) PCT No.: PCT/CN2007/000971
§ 371 (c)(1),
(2), (4) Date: Sep. 9, 2009

(87) PCT Pub. No.: WO2008/116347
PCT Pub. Date: Oct. 2, 2008

(65) Prior Publication Data
US 2010/0040603 A1 Feb. 18, 2010

(51) Int. Cl.
*A61K 38/19* (2006.01)
*A61K 45/00* (2006.01)
*A61K 39/395* (2006.01)
*C07K 14/435* (2006.01)
*C07K 14/475* (2006.01)
*C07K 14/52* (2006.01)
*C07K 16/24* (2006.01)

(52) U.S. Cl. ............... 424/85.1; 424/130.1; 424/198.1; 514/1.1; 514/7.9; 514/13.5; 530/387.1; 530/399

(58) Field of Classification Search .................. None
See application file for complete search history.

(56) References Cited

FOREIGN PATENT DOCUMENTS
WO WO 03/024404 3/2003
WO WO-2008/116347 10/2008

OTHER PUBLICATIONS

Kouroumalis et al, The Journal of Immunology, 2005, vol. 175, pp. 5403-5411.*
Lazar et al. Mol. Cell. Biol., 1988, vol. 8, pp. 1247-1252.*
Wells, Biochemistry, 1990, vol. 29:8509-8517.*
Phillips, A., J Pharm Pharmacology, 2001, vol. 53, pp. 1169-1174.*
Vidal et al. European Journal of Cancer, 2005, vol. 41, pp. 2812-2818.*
Pirollo et al. Cancer Res., 2008; vol. 68, No. 5, apges 1247-1250.*
Broxmeyer, et al., "Myeloid Progenitor Cell Proliferation and Mobilization Effects of BB10010, a Genetically Engineered Variant of Human Macrophage Inflammatory Protein-1alpha, in a Phase I Clinical Trial in Patients with Relapsed/Refractory Breast Cancer," Blood Cells, Molecules & Diseases, vol. 24, No. 1, 1998, pp. 14-30.

Broxmeyer, et al., "Regulation of Hematopoiesis by Chemokine Family Members," Intl. Jour. of Hematology, vol. 74, No. 1, 2001, pp. 9-17.
Broxmeyer, et al., "Synergistic Inhibition In Vivo of Bone Marrow Myeloid Progenitors by Myelosuppressive Chemokines and Chemokine-accelerated Recovery of Progenitors after Treatment of Mice with Ara-C," Experimental Hematology, Elsevier Inc, vol. 34, No. 1, Aug. 1, 2006, pp. 1069-1077.
Christopherson, et al., "Chemokine Regulation of Normal and Pathologic Immune Responses," Stem Cells, vol. 19, No. 5, 2001, pp. 388-396.
Supplementary European Search Report received for EP 07720545.8 completed Ocotber 27, 2010 and mailed Nov. 11, 2010.
Farber, J.M., "A macrophage mRNA selectively induced by γ-interferon encodes a member of the platelet factor 4 family of cytokines", *Proc. Natl. Acad. Sci. USA*, vol. 87, pp. 5238-5242, Jul. 1990.
Gasperini, S. et al., "Gene Expression and Production of the Monokine Induced by IFN-γ (MIG), IFN-Inducible T Cell α Chemoattractant (I-TAC), and IFN -γ-Inducible Protein-10 (IP-10) Chemokines by Human Neutrophils", *Journal of Immunology*, vol. 162, No. 8, pp. 4928-4937, Apr. 15, 1999.
Gorbachev, A.V. et al., "CXC Chemokine Ligand 9/Monokine Induced by IFN-γ Production by Tumor Cells is Critical for T Cell-Mediated Suppression of Cutaneous Tumors", *The Journal of Immunology*, vol. 178, No. 4, pp. 2278-2286, 2007.
Gosling, J. et al., "Molecular uncoupling of C-C chemokine receptor 5-induced chemotaxes and signal transduction from HIV-1 coreceptor activity", *Proc. Natl. Acad. Sci. USA*, vol. 94, pp. 5061-5066, May 1997.
Han, W. et al., "Local signals in stem cell-based bone marrow regeneration", *Cell Research*, vol. 16, pp. 189-195, 2006.
International Search Report and Written Opinion for International Application No. PCT/CN2007/000971 mailed Feb. 14, 2008.
Jinquan, T. et al., "CXC chemokine receptor 3 expression on CD34+ hematopoietic progenitors from human cord blood induced by granulocyte-macrophage colony-stimulating factor: chemotaxis and adhesion induced by its ligands, interferon γ-inducible protein 10 and monokine induced by interferon γ", *Blood Journal*, vol. 96, No. 4, pp. 1230-1238, Aug. 15, 2000.
Lazzeri, E. et al., "CXCR3-binding Chemokines: Novel Multifunctional Therapeutic Targets", *Current Drug Targets—Immune, Endocrine & Metabolic Disorders*, vol. 5, pp. 109-118, 2005.
Liao, F. et al., "Human Mig Chemokine: Biochemical and Functional Characterization", *J. Exp. Med.*, vol. 182, pp. 1301-1314, Nov. 1995.

(Continued)

*Primary Examiner* — Bridget E Bunner
*Assistant Examiner* — Fozia Hamud
(74) *Attorney, Agent, or Firm* — Foley & Lardner LLP

(57) ABSTRACT

CXCL9 promotes bone marrow regeneration, increases peripheral white blood cells, and increases survival if administered prior to treatment of a subject with chemotherapeutic drugs such as 5-FU or radiotherapy. Similar effects are obtained by administering an anti-CXCL9 antibody following chemotherapy or radiotherapy. Compositions and methods are presented for the treatment of cancer and bone marrow diseases.

15 Claims, 10 Drawing Sheets

OTHER PUBLICATIONS

Loos, T. et al., "TLR ligands and cytokines induce CXCR3 ligands in endothelial cells: enhanced CXCL9 in autoimmune arthritis", *Laboratory Investigation*, vol. 86, pp. 902-916, 2006.

Rollins, B.J., "Chemokines", *Blood Journal*, vol. 90, No. 3, pp. 909-928, 1997.

Ruehlmann, J. M. et al., MIG (CXCL9) Chemokine Gene Therapy Combines with Antibody-Cytokine Fusion Protein to Suppress Growth and Dissemination of Murine Colon Carcinoma:, *Cancer Research*, vol. 61, pp. 8498-8503, Dec. 1, 2001.

Yun, J.J. et al., "The Role of MIG/CXCL9 in Cardiac Allograft Vasculopathy", *American Journal of Pathology*, vol. 161, No. 4, Oct. 2002.

Zhang, R. et al., "Combination of Mig (CXCL9) chemokine gene therapy with low-dose cisplatin improves therapeutic efficacy against murine carcinoma", *Gene Therapy*, vol. 13, pp. 1263-1271, 2006.

Colvin, R.A. et al., "CXCR3 Requires Tyrosine Sulfation for Ligand Binding and a Second Extracellular Loop Arginine Residue for Ligand Binding and a Second Extracellular Loop Arginine Residue for Ligand-Induced Chemotaxis," Molecular and Cellular Biology, Aug. 2006, vol. 26, No. 15, pp. 5838-5849.

T6 European First Examination Report; in re: European Application Serial No. 07720545.8; Dated: Feb. 7, 2012; Applicant: General Regeneratives Limited; (5 pgs.).

Chinese Office Action (English Translation Only); In re Patent Application Serial No. 200780053094.7; Issuing Date: Aug. 9, 2011; Applicant: General Regeneratives Limited, (6 pgs.).

Groom, J. R., et al., "CXCR3 ligands: redundant, collaborative and antagonistic functions," Immunology and Cell Biology, 2011, vol. 89, pp. 207-215.

Non-final Office Action received for U.S. Appl. No. 12/565,300 dated Sep. 15, 2010.

Non-final Office Action received for U.S. Appl. No. 13/075,824 dated Feb. 29, 2012.

Notice of Allowance received for U.S. Appl. No. 12/565,300 dated Jan. 18, 2011.

Second Office Action received for Chinese Appln. No. 200780053094.7 dated Feb. 16, 2012. (English translation only).

\* cited by examiner

A

B

```
   1 gaaagacatt ctcggacttc actccaacac agtgactcaa tagaactcag ctctgccatg
  61 aagtccgctg ttcttttcct cttgggcatc atcttcctgg agcagtgtgg agttcgagga
 121 accctagtga taaggaatgc acgatgctcc tgcatcagca ccagccgagg cacgatccac
 181 tacaaatccc tcaaagacct caaacagttt gccccaagcc ccaattgcaa caaaactgaa
 241 atcattgcta cactgaagaa cggagatcaa acctgcctag atccggactc ggcaaatgtg
 301 aagaagctga tgaaagaatg ggaaaagaag atcagccaaa agaaaaagca aaagaggggg
 361 aaaaaacatc aaaagaacat gaaaaacaga aaacccaaaa caccccaaag tcgtcgtcgt
 421 tcaaggaaga ctacataaga gaccattact ttaccaacaa gcaccctgaa tcttaatggg
 481 ttttagattg tactgaaaag ccttccctgg cagagcagcc tttaatacat aggcttttaa
 541 tacattaact caactacaaa acataaagtg ttaatttgaa attataacta actttaggaa
 601 gttaattgca aaactccaat agtaacaatt gctagaggca aaaactctgt gttctacaca
 661 gccaacaaaa tttcatcacg cccttgagcc tagtcgtgat aacatcagat ctgggcaagt
 721 gtccctttcc ttcatagcta tccaatgcac aacagctgtc tggcttccag agccacacat
 781 ttggcagcct ccgaagactt ctgaggctca cgtcaccaaa tcccaggcct gtctgtttgc
 841 tggtgagcta gatagacctc accaagctgg agaggccctc ggccagctgc atttgggtca
 901 gcctagagcc cctgcacaca ttgtgtctca gagatggtgc taatggtttt ggggttctac
 961 agtggagacc accagagttg gccttcagaa cctcccacgt agctttcgag accatgggat
1021 ttcattatta acttgatccc atcttcagag cttattctaa gtttgcctct tcaataaaac
1081 tctcctagaa ggttgtggct gtagcttagt ggcagaacac ttggtgttgc agggaccagg
1141 tccttcacta acagtgcaaa aacttaacca atttaaagaa catttctgg ctactcaaat
1201 tctcttaaat ttattcctgt ttcacaagta aacacttcgc tgctatctaa ttggatttgt
1261 ttgtttgttt gttttacttt ttccaacgag acgggttttt aagagtaggg accacagact
1321 attcccctaa atcttccaca gtgcctacaa aaacttggtt ttgaataatt tcctaattgt
1381 atgtgtgaga ggtagaaagg ctgttacaca ccaggcattg gccaatcccc ggctgctcca
1441 aattgcctaa ctaaccttg gcctccttgc ttgcttacca cttttttttt ttttttttt
1501 aaagaaagtt ttatatctgg ctgtcctaaa actctcaaag tagacaaggc tggtctcaaa
1561 ttcatacata tctgtattct actgcctcct gaatgctggg gttaaaggtg tgtgctacta
1621 cacctgattg cctgccttcc ttcctttctc cctccctccc ttccttcctt ccttccttcc
1681 ttccttcctt ccttccttcc ttccttcctt ccttaaatta tctagctttc ttattatctt
1741 cagacatctt cagcgcacag agccagacag ggtgaaaaag agccttacct tgtgacagga
1801 ggctcgtgtc tttaacaaac aggaatcaca tgttcaagac atttgcggat atttgggact
1861 gctcaggaaa aattacacag gccatctaga aacataagct tacatggaag acaggtttga
1921 ctgattggca aatactagat cttttcctcac tcaaaacaaa attcctctaa tatcattctt
1981 gatcaggaca agctccctag gagtcaacaa aagagctgcc aaatcccttta gcaagtttat
2041 cttaggtgaa tatgaatttc cttgccacct tccctccctc attgcagaaa tcccagtgta
2101 tgattgtatg gattgccaca tcaggctagg agtggtgaaa tggaaagatc agggctggag
2161 agggagccag agttccattc ccagcaccca cccccacgtg tgcgtgagcc ttgtggccac
2221 ctgtgactcc agctccaggg aacccatttc tctcttctgg cctctgcaag cattgcacag
2281 gtgtacacag gcccccatga catacaccca taatctcaga cggcaaataa aaatctttac
2341 agagatattt ttaaaggaat taagagctac aggaagcagt aaattctgcg agtggaagtg
2401 tggacagggc caagttagcc tgtgtgggag ctggaaactg tctagagag gaggtctgat
2461 gaattagata gaaaagaatg tctctgggca gaagttccgt cttgagcatg cttttctca
2521 aatactgcca ttcctggcgc tgcatgcagg tggtttttgt gctgctggtg ggactcccat
2581 ccaaacaaca ttgcacagtc aaaacgttgt ccacctccct tcggtaattt actttg
(SEQ ID NO:9)
```

Figure 15

```
   1 atccaataca ggagtgactt ggaactccat tctatcacta tgaagaaaag tggtgttctt
  61 ttcctcttgg gcatcatctt gctggttctg attggagtgc aaggaacccc agtagtgaga
 121 aagggtcgct gttcctgcat cagcaccaac caagggacta tccacctaca atccttgaaa
 181 gaccttaaac aatttgcccc aagcccttcc tgcgagaaaa ttgaaatcat tgctacactg
 241 aagaatggag ttcaaacatg tctaaaccca gattcagcag atgtgaagga actgattaaa
 301 aagtgggaga aacaggtcag ccaaaagaaa aagcaaaaga atgggaaaaa acatcaaaaa
 361 aagaaagttc tgaaagttcg aaaatctcaa cgttctcgtc aaaagaagac tacataagag
 421 accacttcac caataagtat tctgtgttaa aaatgttcta ttttaattat accgctatca
 481 ttccaaagga ggatggcata taatacaaag gcttattaat ttgactagaa aatttaaaac
 541 attactctga aattgtaact aaagttagaa agttgatttt aagaatccaa acgttaagaa
 601 ttgttaaagg ctatgattgt ctttgttctt ctaccaccca ccagttgaat ttcatcatgc
 661 ttaaggccat gatttttagca atacccatgt ctacacagat gttcacccaa ccacatccca
 721 ctcacaacag ctgcctggaa gagcagccct aggcttccac gtactgcagc ctccagagag
 781 tatctgaggc acatgtcagc aagtcctaag cctgttagca tgctggtgag ccaagcagtt
 841 tgaaattgag ctggacctca ccaagctgct gtggccatca acctctgtat ttgaatcagc
 901 ctacaggcct cacacacaat gtgtctgaga gattcatgct gattgttatt gggtatcacc
 961 actggagatc accagtgtgt ggctttcaga gcctcctttc tggctttgga agccatgtga
1021 ttccatcttg cccgctcagg ctgaccactt tatttctttt tgttcccctt tgcttcattc
1081 aagtcagctc ttctccatcc taccacaatg cagtgccttt cttctctcca gtgcacctgt
1141 catatgctct gatttatctg agtcaactcc tttctcatct tgtccccaac accccacaga
1201 agtgctttct tctcccaatt catcctcact cagtccagct tagttcaagt cctgcctctt
1261 aaataaacct ttttggacac acaaattatc ttaaaactcc tgtttcactt ggttcagtac
1321 cacatggggtg aacactcaat ggttaactaa ttcttgggtg tttatcctat ctctccaacc
1381 agattgtcag ctccttgagg gcaagagcca cagtatattt ccctgtttct tccacagtgc
1441 ctaataatac tgtggaacta ggttttaata atttttttaat tgatgttgtt atgggcagga
1501 tggcaaccag accattgtct cagagcaggt gctggctctt tcctggctac tccatgttgg
1561 ctagcctctg gtaacctctt acttattatc ttcaggacac tcactacagg gaccagggat
1621 gatgcaacat ccttgtcttt ttatgacagg atgtttgctc agcttctcca acaataagaa
1681 gcacgtggta aaacacttgc ggatattctg gactgttttt aaaaaatata cagtttaccg
1741 aaaatcatat aatcttacaa tgaaaaggac tttatagatc agccagtgac caacccttttc
1801 ccaaccatac aaaaattcct tttcccgaag gaaaagggct ttctcaataa gcctcagctt
1861 tctaagatct aacaagatag ccaccgagat ccttatcgaa actcatttta ggcaaatatg
1921 agtttttattg tccgtttact tgtttcagag tttgtattgt gattatcaat taccacacca
1981 tctcccatga agaaagggaa cggtgaagta ctaagcgcta gaggaagcag ccaagtcggt
2041 tagtggaagc atgattggtg cccagttagc ctctgcagga tgtggaaacc tccttccagg
2101 ggaggttcag tgaattgtgt aggagaggtt gtctgtggcc agaatttaaa cctatactca
2161 ctttcccaaa ttgaatcact gctcacactg ctgatgattt agagtgctgt ccggtggaga
2221 tcccacccga acgtcttatc taatcatgaa actccctagt tccttcatgt aacttccctg
2281 aaaatctaa gtgtttcata aatttgagag tctgtgaccc acttaccttg catctcacag
2341 gtagacagta taactaacaa accaaagac tacatattgt cactgacaca cacgttataa
2401 tcatttatca tatatataca tacatgcata cactctcaaa gcaaataatt tttcacttca
2461 aaacagtatt gacttgtata ccttgtaatt tgaaatattt tcttttgttaa aatagaatgg
2521 tatcaataaa tagaccatta atcag     (SEQ ID NO:10)
```

Figure 16

```
   1 ccaaccacaa gcaccaaagc agaggggcag gcagcacacc acccagcagc cagagcacca
  61 gcccagccat ggtccttgag gtgagtgacc accaagtgct aaatgacgcc gaggttgccg
 121 ccctcctgga gaacttcagc tcttcctatg actatggaga aaacgagagt gactcgtgct
 181 gtacctcccc gccctgccca caggacttca gcctgaactt cgaccgggcc ttcctgccag
 241 ccctctacag cctcctcttt ctgctggggc tgctgggcaa cggcgcggtg gcagccgtgc
 301 tgctgagccg gcggacagcc ctgagcagca ccgacacctt cctgctccac ctagctgtag
 361 cagacacgct gctggtgctg acactgccgc tctgggcagt ggacgctgcc gtccagtggg
 421 tctttggctc tggcctctgc aaagtggcag gtgccctctt caacatcaac ttctacgcag
 481 gagccctcct gctggcctgc atcagctttg accgctacct gaacatagtt catgccaccc
 541 agctctaccg ccggggggccc ccggcccgcg tgaccctcac ctgcctggct gtctgggggc
 601 tctgcctgct tttcgccctc ccagacttca tcttcctgtc ggcccaccac gacgagcgcc
 661 tcaacgccac ccactgccaa tacaacttcc cacaggtggg ccgcacggct ctgcgggtgc
 721 tgcagctggt ggctggcttt ctgctgcccc tgctggtcat ggcctactgc tatgcccaca
 781 tcctggccgt gctgctggtt ccaggggcc agcggcgcct gcgggccatg cggctggtgg
 841 tggtggtcgt ggtggccttt gccctctgct ggacccccta tcacctggtg gtgctggtgg
 901 acatcctcat ggacctgggc gctttggccc gcaactgtgg ccgagaaagc agggtagacg
 961 tggccaagtc ggtcacctca ggcctgggct acatgcactg ctgcctcaac ccgctgctct
1021 atgcctttgt aggggtcaag ttccgggagc ggatgtggat gctgctcttg cgcctgggct
1081 gccccaacca gagagggctc cagaggcagc catcgtcttc ccgccgggat tcatcctggt
1141 ctgagacctc agaggcctcc tactcgggct tgtgaggccg gaatccgggc tccccttttcg
1201 cccacagtct gacttccccg cattccaggc tcctccctcc ctctgccggc tctggctctc
1261 cccaatatcc tcgctcccgg gactcactgg cagcccagc accaccaggt ctcccgggaa
1321 gccaccctcc cagctctgag gactgcacca ttgctgctcc ttagctgcca agccccatcc
1381 tgccgcccga ggtggctgcc tggagcccca ctgcccttct catttggaaa ctaaaacttc
1441 atcttcccca agtgcgggga gtacaaggca tggcgtagag ggtgctgccc catgaagcca
1501 cagcccaggc ctccagctca gcagtgactg tggccatggt ccccaagacc tctatatttg
1561 ctcttttatt tttatgtcta aaatcctgct taaaactttt caataaacaa gatcgtcagg
1621 accaaaaaaa (SEQ ID NO:11)
```

Figure 17

METHODS FOR PROMOTING PROTECTION AND REGENERATION OF BONE MARROW USING CXCL9 AND ANTI-CXCL9 ANTIBODIES

CROSS-REFERENCE TO RELATED APPLICATIONS

The present application claims priority as a national stage application of International Application No. PCT/CN2007/000971 filed on Mar. 26, 2007, the entire contents of which are incorporated herein by reference in its entirety.

FIELD OF THE INVENTION

This invention relates to methods for promoting protection and regeneration of bone marrow using CXCL9 and anti-CXCL9 antibodies.

BACKGROUND

CXCL9, also known as CXCL9 (monokine induced by IFN-γ), was first discovered from the mouse macrophage cell line RAW 264.7 in 1990 [1]. It is a member of the CXC subfamily of chemokines, characterized by its first two cysteines being separated by a single amino acid. In vivo, CXCL9 is produced by macrophages in response to IFN-γ, but not in response to other macrophage activators including IFN-α, IFN-β and LPS. CXCL9 is known as a chemoattractant for activated T lymphocytes [2], tumor-infiltrating lymphocytes [3] as well as NK cells and TH1 lymphocytes [4]. CXCL9 has been investigated primarily for its function in autoimmune diseases [6], allograft rejection [7] and cancer therapy [8].

Aside from the above mentioned functions in the immune system, CXCL9 also has two other known functions. First, CXCL9 is an angiostatic agent [10,11]. Zhang et al. designed a gene therapy method based on the anti-angiogenic effect of CXCL9 in tumors [8]. They combined pORF-CXCL9 with low-dose cisplatin to treat tumors and the combination showed significant antitumor activity. Second, CXCL9 inhibits proliferation of myeloid progenitors stimulated by multiple growth factors in vitro [5,9]. Many CXC chemokines, for example PF4 (platelet factor), have myelosuppressive activity [5]. Further, CXCR3 expression is up regulated in hematopoietic cells stimulated by factors such as G-CSF [12].

Myelosuppression is the main reason for the lethal side effects of chemotherapy or radiotherapy of cancer. Many drugs have been developed to deal with myelosuppression. Up to now, two approaches have been used to protect bone marrow from the toxicity of chemotherapy or radiotherapy. In one approach, positive regulators are administrated prior to therapy to stimulate the proliferation of critical stem cells, progenitor cells or end-stage hematopoietic cells. These positive regulators, including IL-6 [13] and CSFs [14,15], can result in an increase of hematopoietic cells before chemotherapy, thus allowing a more rapid recovery. Another approach is to administer these regulators post chemotherapy or radiotherapy, to enhance the proliferation of hematopoietic cells, also resulting in a better recovery.

There remains a need to develop new compositions and methods to prevent or reduce myelosuppression as well as to improve recovery from myelosuppression caused by chemotherapy, radiation therapy, and other myelotoxic agents.

SUMMARY OF THE INVENTION

The invention provides methods for using CXCL9 and anti-CXCL9 antibodies to protect hematopoietic cells and other bone marrow cells from the harmful effects of chemotherapy or radiotherapy. The invention also provides treatment methods for cancer and various bone marrow disorders. On the one hand, the methods are based on the myelosuppressive action of CXCL9 and, on the other hand, on the ability of anti-CXCL9 antibodies to counteract such myelosuppressive effects. The invention offers novel ways to enhance the recovery of the suppressed hematopoietic system as part of a regimen of chemotherapy or radiation therapy, particularly, in the treatment of cancer.

The methods of the invention have the ability to protect hematopoietic cells, particularly, stem cells and progenitor cells, from the destructive effects of chemotherapy, radiotherapy or a combination thereof. CXCL9 was discovered to inhibit the proliferation of hematopoietic cells in vitro. Administration of CXCL9 as an agent or therapeutic agent prior to administration of a chemotherapy agent in mice results in a more rapid recovery of bone marrow and circulating leukocytes as well as a higher survival rate in the animals. An anti-CXCL9 antibody as an agent or therapeutic agent led to better recovery of peripheral white cell counts and a higher survival rate. CXCL9 and an anti-CXCL9 antibody can also be administered as compositions comprising pharmaceutically acceptable carriers. Moreover, CXCL9 and an anti-CXCL9 antibody may be administered as part of a therapeutic protocol that can provide treatment before and after chemotherapy or radiotherapy.

In one aspect, the invention provides a method of preventing bone marrow cell damage during chemotherapy or radiotherapy. The method includes administering an effective amount (e.g., therapeutically effective amount) of CXCL9 to a subject before the subject receives chemotherapy or radiotherapy. After chemotherapy or radiation therapy, the bone marrow cell density of the subject is increased compared to what happens to a subject who does not receive CXCL9. That is, the reduction of bone marrow cell density that normally follows chemotherapy or radiation therapy is partially or entirely reversed by pretreatment with CXCL9.

Another aspect of the invention is method of increasing the level of peripheral white blood cells following chemotherapy or radiotherapy. The method comprises administering an effective amount of CXCL9 to a subject prior to administering chemotherapy or radiotherapy to the subject. The reduction of peripheral leukocytes that normally follows chemotherapy or radiation therapy is partially or entirely reversed by pretreatment with CXCL9.

A further aspect of the invention is a method of treating cancer. According to this method, CXCL9 is administered to a subject with cancer and then chemotherapy or radiation therapy is administered to the subject.

In one aspect of the invention, a method of preventing bone marrow cell damage resulting from chemotherapy or radiotherapy is provided. The method can comprise administering an effective amount of CXCL9 or a CXCR3 agonist to a subject prior to administering chemotherapy or radiotherapy to said subject. Preferably, following chemotherapy or radiotherapy, the bone marrow cell density of said subject is increased compared to a control subject not receiving CXCL9 or a CXCR3 agonist.

In another aspect, the invention provides a method of increasing the level of peripheral white blood cells following chemotherapy or radiotherapy. For example, the method comprises administering an effective amount of CXCL9 or a CXCR3 agonist to a subject prior to administering chemotherapy or radiotherapy to said subject. Following chemotherapy or radiotherapy, the level of peripheral white blood cells of said subject is preferably increased compared to a control subject not receiving CXCL9 or a CXCR3 agonist.

In one aspect of the invention, a method of treating cancer is provided that comprises administering an effective amount of CXCL9 or a CXCR3 agonist to a subject with cancer. The method can also comprise administering chemotherapy or radiotherapy to said subject following the administration of CXCL9 or a CXCR3 agonist.

In another aspect of the invention, a method of preventing bone marrow cell damage resulting from chemotherapy or radiotherapy is provided. The method comprises administering an effective amount of CXCL9 or a CXCR3 agonist to a subject prior to administering chemotherapy or radiotherapy to said subject. The method can also comprise administering chemotherapy or radiotherapy to said subject following the administration of CXCL9 or a CXCR3 agonist. Moreover, a method of the invention can further comprise administering to said subject an effective amount of an agent (e.g., therapeutic agent) selected from an anti-CXCL9 antibody, a CXCL9 siRNA, a CXCL9 antisense nucleic acid, a CXCR3 antibody, a CXCR3 siRNA, a CXCR3 antisense nucleic acid and a CXCR3 antagonist as well as combinations thereof. Preferably, following chemotherapy or radiotherapy, the bone marrow cell density of said subject is increased compared to a control subject not receiving said agent. An agent or therapeutic agent of the invention can also be administered as a composition comprising a therapeutically effective amount of the agent and a pharmaceutically acceptable carrier.

In one aspect, a method of increasing the level of peripheral white blood cells following chemotherapy or radiotherapy is provided. For example, the method can comprise administering an effective amount of CXCL9 or an agonist of CXCR3 to a subject. The method can further comprise administering chemotherapy or radiotherapy to said subject following the administration of CXCL9 or a CXCR3 agonist. In another aspect, the method can comprise administering to said subject an effective amount (e.g., therapeutically effective amount) of an agent selected from an anti-CXCL9 antibody, a CXCL9 siRNA, a CXCL9 antisense nucleic acid, a CXCR3 antibody, a CXCR3 siRNA, a CXCR3 antisense nucleic acid and a CXCR3 antagonist as well as combinations thereof such that following chemotherapy or radiotherapy, the level of peripheral white blood cells of said subject is increased compared to a control subject not receiving said agent.

In another aspect, a method of treating cancer is provided. The method comprises administering an effective amount of CXCL9 or a CXCR3 agonist to a subject with cancer. Preferably, the method also comprises administering chemotherapy or radiotherapy to said subject following the administration of CXCL9 or a CXCR3 agonist. The method can also comprise administering an effective amount of an agent selected from an anti-CXCL9 antibody, a CXCL9 siRNA, a CXCL9 antisense nucleic acid, a CXCR3 antibody, a CXCR3 siRNA, a CXCR3 antisense nucleic acid, a CXCR3 antagonist and combinations thereof to said subject.

In one aspect of the invention, a method of preventing bone marrow cell damage resulting from chemotherapy or radiotherapy is provided. The method comprises administering chemotherapy or radiotherapy to a subject. The method also comprises administering to said subject an effective amount of an agent selected from an anti-CXCL9 antibody, a CXCL9 siRNA, a CXCL9 antisense nucleic acid, a CXCR3 antibody, a CXCR3 siRNA, a CXCR3 antisense nucleic acid and a CXCR3 antagonist as well as combinations thereof. Preferably, following chemotherapy or radiotherapy, the bone marrow cell density of said subject is increased compared to a control subject not receiving said agent.

In one aspect, a method of the invention comprises increasing the level of peripheral white blood cells following chemotherapy or radiotherapy. The method can comprise administering chemotherapy or radiotherapy to said subject. Furthermore, the method can comprise administering to said subject an effective amount of an agent selected from an anti-CXCL9 antibody, a CXCL9 siRNA, a CXCL9 antisense nucleic acid, a CXCR3 antibody, a CXCR3 siRNA, a CXCR3 antisense nucleic acid, and a CXCR3 antagonist such that following chemotherapy or radiotherapy, the level of peripheral white blood cells of said subject is increased compared to a control subject not receiving said agent.

In another aspect of the invention, a method of treating cancer is provided. The method comprises administering chemotherapy or radiotherapy to a subject with cancer. The method also comprises administering an effective amount of an agent selected from an anti-CXCL9 antibody, a CXCL9 siRNA, a CXCL9 antisense nucleic acid, a CXCR3 antibody, a CXCR3 siRNA, a CXCR3 antisense nucleic acid and a CXCR3 antagonist to said subject.

A method of the invention can also be carried out with a chemotherapy (e.g., a chemotherapy protocol or regime) that is cell cycle specific. For example, the chemotherapy of a method of the invention can comprise administering an agent selected from the group consisting of 5-fluorouracil, Ara-C, vinblastine, methotrexate and combinations thereof. In one aspect, a method of the invention can be carried out with a chemotherapy that is cell cycle non-specific. For example, the chemotherapy of a method of the invention can comprise administering an agent selected from the group consisting of cyclophosphamide, doxorubicin, cisplatin, busulfan and combinations thereof.

In one aspect, a method of the invention can comprise a radiotherapy that involves administering external beam radiation or a radiopharmaceutical agent. A method of the invention can also comprise administering CXCL9 in daily doses for, but not limited to, two or more days prior to administering said chemotherapy or said radiotherapy. For example, CXCL9 can be administered for 5 days or more. In another aspect of a method of the invention, CXCL9 can be administered via a eukaryotic expression vector. An exemplary expression vector for a method of the invention is pcDNA3.1 (−).

For a method of the invention, an expression vector can be administered by electroporation of skeletal muscle. Alternatively, an expression vector can be administered in vitro to bone marrow cells from the subject. In one aspect, a method of the invention can comprise administering CXCL9 in a conjugated form or a CXCL9 fusion protein. An exemplary CXCL9 fusion protein can be a albumin-CXCL9 fusion protein. Preferably, albumin can be a serum albumin and, more preferably, a human serum albumin (HSA). The invention contemplates that a conjugated form of CXCL9 or a CXCL9 fusion protein can alter the half-life (e.g., therapeutic half-life) of CXCL9, which could be advantageous for certain chemotherapy or radiotherapy treatment protocols.

In one aspect, a method of the invention can comprise administering an agent selected from an anti-CXCL9 antibody, a CXCL9 siRNA, a CXCL9 antisense nucleic acid, a CXCR3 antibody, a CXCR3 antisense nucleic acid, a CXCR3 siRNA and combinations thereof. For example, the agent can be administered in daily doses for, but not limited to, two or more days following the administration of chemotherapy or said radiotherapy. Preferably, the agent can be administered for at least 10 days following the administration of chemotherapy or radiotherapy. In another aspect of the invention, an anti-CXCL9 antibody or CXCR3 antibody can be a polyclonal antibody or a monoclonal antibody. The anti-CXCL9 antibody or CXCR3 antibody can also be a Fab fragment, a scFv antibody or a single domain antibody. The anti-CXCL9 antibody or CXCR3 antibody can also be a chimeric antibody, a humanized antibody (optionally including back mutations) or a human antibody.

An anti-CXCL9 antibody or CXCR3 antibody of the invention can also be provided as a conjugated form. In one aspect, a method of the invention comprises administering CXCL9 siRNA. For example, CXCL9 siRNA can comprise a sequence complementary to 18 to 30 consecutive nucleotides of SEQ ID NO:10 or CXCR3 siRNA can comprise a sequence complementary to 18 to 30 consecutive nucleotides of SEQ ID NO:11. In another aspect of the invention, a method of treating a subject having a bone marrow disorder characterized by a reduction in bone marrow cells is provided. The method comprises administering an effective amount of an agent selected from an anti-CXCL9 antibody, a CXCL9 siRNA, a CXCL9 antisense nucleic acid, a CXCR3 antibody, a CXCR3 antisense nucleic acid, a CXCR3 siRNA and combinations thereof to said subject. Preferably, the effective amount of the agent increases bone marrow cell density for the subject.

For a method of the invention, a bone marrow disorder to be treated is selected from the group consisting of pancytopenia, aplastic anemia, thrombocytopenia, leucopenia, neutropenia, and myelofibrosis. The agent administered according to a method of the invention can be administered in daily doses for, but not limited to, two or more days. Similarly, the method can comprise administering the agent for at least 10 days. In one aspect, an anti-CXCL9 antibody or CXCR3 antibody is a polyclonal antibody or a monoclonal antibody. As described herein, an anti-CXCL9 antibody or CXCR3 antibody can be a Fab fragment, a scFv antibody or a single domain antibody.

The invention also provides for the use of CXCL9 or a CXCR3 agonist in the preparation of a medicament for the prevention of bone marrow cell damage. In one aspect, the invention provides for the use of CXCL9 or a CXCR3 agonist in the preparation of a medicament for increasing the level of peripheral white blood cells. In another aspect, the invention provides for the use of CXCL9 or a CXCR3 agonist in the preparation of a medicament for treating cancer. In yet another aspect, the invention provides for the use of an anti-CXCL9 antibody, a CXCR9 siRNA, a CXCL9 antisense nucleic acid, a CXCR3 antibody, a CXCR3 siRNA, a CXCR3 antisense nucleic acid, a CXCR3 antagonist or combination thereof in the preparation of a medicament for the prevention of bone marrow cell damage. The invention further provides for the use of an anti-CXCL9 antibody, a CXCR9 siRNA, a CXCL9 antisense nucleic acid, a CXCR3 antibody, a CXCR3 siRNA, a CXCR3 antisense nucleic acid, or a CXCR3 antagonist in the preparation of a medicament for increasing the level of peripheral white blood cells.

In one aspect, the invention provides for the use of an anti-CXCL9 antibody, a CXCR9 siRNA, a CXCL9 antisense nucleic acid, a CXCR3 antibody, a CXCR3 siRNA, a CXCR3 antisense nucleic acid, or a CXCR3 antagonist in the preparation of a medicament for treating cancer. In another aspect, the invention provides for the use of an anti-CXCL9 antibody, a CXCR9 siRNA, a CXCL9 antisense nucleic acid, a CXCR3 antibody, a CXCR3 siRNA, a CXCR3 antisense nucleic acid, or a CXCR3 antagonist in the preparation of a medicament for treating a bone marrow disorder. The invention also provides compositions comprising a therapeutically effective amount of CXCL9 and a pharmaceutically acceptable carrier. The composition can comprise CXCL9 present in an amount effective to prevent bone marrow cell damage resulting from chemotherapy or radiotherapy.

In one aspect, a composition of the invention comprises CXCL9 present in an amount effective to increase the level of peripheral white blood cells following chemotherapy or radiotherapy. In another aspect, a composition of the invention comprises CXCL9 present in an amount effective to treat cancer. The invention also provides a composition comprising a therapeutically effective amount of a CXCR3 agonist and a pharmaceutically acceptable carrier. For example, the CXCR3 agonist can be present in an amount effective to prevent bone marrow cell damage resulting from chemotherapy or radiotherapy.

The invention also provides a composition comprising a CXCR3 agonist present in an amount effective to increase the level of peripheral white blood cells following chemotherapy or radiotherapy. In one aspect, the composition comprises a CXCR3 agonist present in an amount effective to treat cancer. In yet another aspect, the composition can comprise a therapeutically effective amount of an anti-CXCL9 antibody and a pharmaceutically acceptable carrier. Preferably, the anti-CXCL9 antibody can be present in an amount effective to prevent bone marrow cell damage resulting from chemotherapy or radiotherapy. An exemplary composition of the invention can comprise an anti-CXCL9 antibody present in an amount effective to increase the level of peripheral white blood cells following chemotherapy or radiotherapy.

The invention also provides a composition in which the anti-CXCL9 antibody can be present in an amount effective to treat cancer. In one aspect, a composition of the invention comprises a therapeutically effective amount of a CXCL9 siRNA and a pharmaceutically acceptable carrier. For example, CXCL9 siRNA of a composition of the invention can be present in an amount effective to prevent bone marrow cell damage resulting from chemotherapy or radiotherapy. Moreover, the invention provides a composition in which said CXCL9 siRNA can be present in an amount effective to increase the level of peripheral white blood cells following chemotherapy or radiotherapy. Preferably, the composition can comprise CXCL9 siRNA present in an amount effective to treat cancer. In another aspect, a composition of the invention can comprise a therapeutically effective amount of a CXCR3 antibody and a pharmaceutically acceptable carrier.

In one aspect, the composition of said CXCR3 antibody can be present in an amount effective to prevent bone marrow cell damage resulting from chemotherapy or radiotherapy. A composition of the invention can comprise a CXCR3 antibody present in an amount effective to increase the level of peripheral white blood cells following chemotherapy or radiotherapy. An exemplary composition of the invention can comprise said CXCR3 antibody present in an amount effective to treat cancer. The invention also provides a composition comprising a therapeutically effective amount of a CXCR3 siRNA and a pharmaceutically acceptable carrier.

In another aspect, a composition of the invention can comprise CXCR3 siRNA present in an amount effective to prevent bone marrow cell damage resulting from chemotherapy or radiotherapy. The invention also provides CXCR3 siRNA present in an amount effective to increase the level of peripheral white blood cells following chemotherapy or radiotherapy. In yet another aspect, the invention provides a composition in which CXCR3 siRNA is present in an amount effective to treat cancer. The invention further provides a composition comprising a therapeutically effective amount of a CXCR3 antagonist and a pharmaceutically acceptable carrier.

In one aspect, a composition of the invention comprises a CXCR3 agonist in an amount effective to prevent bone marrow cell damage resulting from chemotherapy or radiotherapy. In yet another aspect of the invention, a CXCR3 agonist can be present in an amount effective to increase the level of peripheral white blood cells following chemotherapy or radiotherapy. A composition of the invention can comprise a CXCR3 agonist present in an amount effective to treat cancer.

The invention also provides a composition in which a CXCL9 expression vector can be present in an amount effective to increase the level of peripheral white blood cells following chemotherapy or radiotherapy. Moreover, a composition of the invention can comprise a CXCL9 expression vector present in an amount effective to treat cancer. For example, a composition of the invention can comprise a therapeutically effective amount of a CXCL9 eukaryotic expression vector. For example, a CXCL9 expression vector can be present in an amount effective for a composition of the invention to prevent bone marrow cell damage resulting from chemotherapy or radiotherapy.

A further aspect of the invention is a method of purifying a mammalian CXCL9 protein, such as a human or mouse CXCL9 protein. The method comprises binding CXCL9 to a cation exchanger at a pH below the pI of the CXCL9, washing the cation exchanger to remove other proteins, and contacting the cation exchanger with an elution buffer having a gradient of increasing ionic strength, wherein purified CXCL9 protein is eluted from the cation exchanger.

Still another aspect of the invention is combination therapy to prevent damage to bone marrow, or to increase peripheral white blood cells following chemotherapy or radiotherapy, or to treat cancer or a bone marrow disorder. In some embodiments, a myeolosuppressive agent, such as CCL3, is administered prior to chemotherapy or radiotherapy in addition to the administration of CXCL9 or a CXCR3 agonist prior to chemotherapy or radiotherapy, or in addition to a CXCR3 antagonist (including a CXCL9 antibody, a CXCL9 siRNA, a CXCL9 antisense nucleic acid, a CXCR3 antibody, a CXCR3 siRNA, a CXCR3 antisense nucleic acid, or a small molecule CXCR3 antagonist) following chemotherapy or radiotherapy. In other embodiments, a hematopoietic growth factor, such as GM-CSF or G-CSF, is administered following chemotherapy or radiotherapy in addition to the administration of CXCL9 or a CXCR3 agonist prior to chemotherapy or radiotherapy, or in addition to a CXCR3 antagonist (including a CXCL9 antibody, a CXCL9 siRNA, a CXCL9 antisense nucleic acid, a CXCR3 antibody, a CXCR3 siRNA, a CXCR3 antisense nucleic acid, or a small molecule CXCR3 antagonist) following chemotherapy or radiotherapy.

Any of the methods of the invention can comprise a subject that is a mammal and, preferably, a human. In another aspect of the invention, a method of enhancing the effectiveness of chemotherapy or radiotherapy to treat cancer is provided. Preferably, the method comprises administering to a subject with cancer an effective amount of CXCL9 or a CXCR3 agonist and administering chemotherapy or radiotherapy at a higher dose than would be administered in the absence of the administration of CXCL9 or a CXCR3 agonist. For the method of the invention, the effectiveness of the chemotherapy or radiotherapy can be enhanced by administering CXCL9 or a CXCR3 agonist to a subject. The invention also provides for a composition comprising a therapeutically effective amount of an anti-CXCL9 antibody, a CXCL9 siRNA, a CXCL9 antisense nucleic acid, a CXCR3 antibody, a CXCR3 antisense nucleic acid, a CXCR3 siRNA or combinations thereof and a pharmaceutically acceptable carrier.

For example, the invention provides a composition comprising an anti-CXCL9 antibody, a CXCL9 siRNA, a CXCL9 antisense nucleic acid, a CXCR3 antibody, a CXCR3 antisense nucleic acid, a CXCR3 siRNA or combinations thereof in an amount effective to prevent bone marrow cell damage resulting from chemotherapy or radiotherapy. In yet another aspect of the invention, an anti-CXCL9 antibody, a CXCL9 siRNA, a CXCL9 antisense nucleic acid, a CXCR3 antibody, a CXCR3 antisense nucleic acid, a CXCR3 siRNA or combinations thereof is present in a composition of the invention in an amount effective to increase the level of peripheral white blood cells following chemotherapy or radiotherapy. A composition of the invention can also comprise an anti-CXCL9 antibody, a CXCL9 siRNA, a CXCL9 antisense nucleic acid, a CXCR3 antibody, a CXCR3 antisense nucleic acid, a CXCR3 siRNA or combinations thereof present in an amount effective to treat cancer.

DESCRIPTION OF THE DRAWINGS

Lane 4: pellet fraction of E. coli lysate after sonication of induced E. coli.

FIG. 15 shows the cDNA sequence of MuCXCL9 (SEQ ID NO:9).

FIG. 16 shows the cDNA sequence of HuCXCL9 (SEQ ID NO:10).

FIG. 17 shows the cDNA sequence of HuCXCR3 (SEQ ID NO:11).

DETAILED DESCRIPTION OF THE INVENTION

Figure 1A:
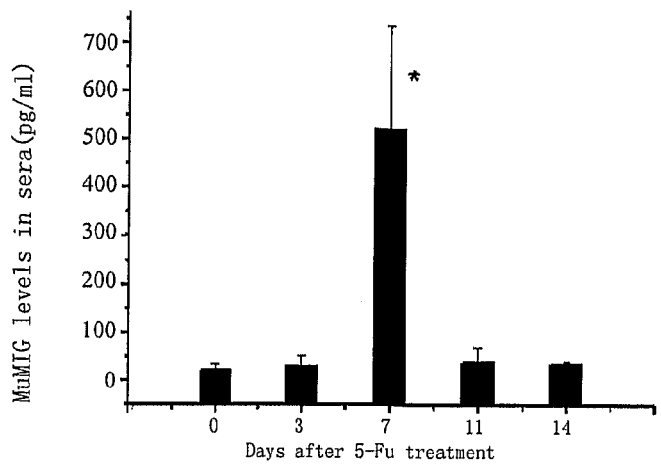
FIG. 1A shows the results of an ELISA of CXCL9 levels in mouse serum after 5-FU treatment.

CXCL9 promotes bone marrow regeneration, increases peripheral white blood cells, and increases survival if administered prior to treatment of a subject with chemotherapeutic drugs such as 5-FU or radiotherapy. Similar effects are obtained by administering an anti-CXCL9 antibody following chemotherapy or radiotherapy. Compositions and methods are presented for the treatment of cancer and bone marrow diseases.

The invention relates to novel properties of the chemokine CXCL9, which was previously thought to function merely as a monokine involved in macrophage responses to interferon gamma. According to the present invention, however, CXCL9 surprisingly plays a central role in the regeneration of bone marrow after injury. The inventors have discovered novel compositions and methods involving CXCL9 that are useful for preventing the loss of bone marrow cells in response to damaging environmental factors, including chemotherapeutic agents and radiation, on the one hand and useful for regenerating already damaged bone marrow on the other. The compositions and methods of the invention can be used to reduce the serious, sometimes fatal loss of bone marrow function associated with chemotherapy or radiation therapy and are especially useful as an adjunct therapy in the treatment of cancer. They also can be used to remedy the loss of bone marrow cells associated with bone marrow disorders such as aplastic anemia and leukemia.

CXCL9 has a potent antimyelogenic effect, limiting the proliferation of bone marrow progenitor cells and resulting in a reduction in bone marrow cell number. Without intending to limit the invention to any particular mechanism, it appears that this antimyelogenic property leads to the protective effect of CXCL9 on bone marrow cells that are subsequently challenged with damaging agents such as chemotherapeutic drugs or radiation. By inducing a quiescent, nonproliferating state, CXCL9 administration prevents destruction of critical progenitor cells or stem cells in bone marrow during chemotherapy or radiotherapy, resulting in vastly improved recovery subsequent to such therapy. This effect can be utilized by the physician to either improve the safety and tolerability of chemotherapy or radiation therapy, or to increase the therapeutic efficacy by raising the dose of the chemotherapeutic agent or radiation to a level that would not be tolerated without CXCL9 treatment. Therefore, through the use of the invention, the safety and effectiveness of common cancer therapies can be enhanced.

Furthermore, the inventors have discovered that the effects of CXCL9 continue to play a role subsequent to bone marrow injury. The present inventors unexpectedly found that CXCL9 gene expression in bone marrow increases dramatically by several fold after treatment with a common chemotherapeutic drug, 5-fluorouracil (5-FU). Thus, during the critical recovery period, the antiproliferative activity of CXCL9 becomes stronger, serving as an impediment to bone marrow recovery. According to the invention, the administration of an antagonist of CXCL9 activity during the period following chemotherapy or radiation therapy will lead to improved recovery of bone marrow cells (i.e., faster increase in cell number, and/or higher eventual cell number). Again, without limiting the invention to any particular mechanism, the administration of any agent that antagonizes the activity of CXCL9 appears to reduce the harmful effect caused by the increase in CXCL9 expression after exposure to a bone marrow damaging agent.

Accordingly, one embodiment of the invention is a method for preventing bone marrow cell damage resulting from chemotherapy or radiotherapy, or exposure to a myelotoxic agent. The method includes administering an effective amount of CXCL9, or a CXCR3 agonist, to a subject who is about to receive either chemotherapy or radiation therapy. The outcome of performing this method is that the cell density, or total cell number per unit volume of bone marrow, is greater after chemotherapy or radiotherapy than if the method had not been performed. Various types of damage to bone marrow can be prevented by this method. Chemotherapeutic agents as well as radiation cause damage to DNA of cells in the bone marrow, and if that damage is severe enough, apoptosis is induced and the cell dies. This is the underlying mechanism of cancer treatment with these therapies. However, damage leading to apoptosis of any of a variety of bone marrow progenitor cells or stem cells will reduce the number of bone marrow cells and the number of circulating leukocytes, as well as weaken the entire immune system, within a few days after the chemical agent or radiation is administered. Thus, administering CXCL9 or an agonist of its receptor CXCR3 prior to chemotherapy or radiotherapy preserves stem cells and progenitor cells by reducing the damaging effects on these cells, resulting in quicker recovery of bone marrow and immune function after the treatment, and improving the selectivity of chemotherapy or radiation therapy for cancer cells compared to normal cells.

Administration of CXCL9 refers to administering a CXCL9 polypeptide, including sequence variants such as insertions, deletions, and conservative amino acid substitutions, or related forms such as mutations or CXCL9 polypeptides of related species having a high degree of sequence similarity. In general, a CXCL9 for administration according to the invention is one which is functionally active as determined by its antimyelogenic effect, or as determined by its ability to prevent loss of bone marrow cells following 5-FU treatment or treatment with another chemotherapeutic agent or radiation that causes a significant loss of bone marrow cells within a few days after administration. A CXCL9 for administration according to the invention is preferably a CXCL9 having the same amino acid sequence as the CXCL9 of the species to which it is administered, so as to avoid any immune response against the administered CXCL9. For example, if the subject is human, then the administered CXCL9 is preferably human CXCL9, e.g., recombinant human CXCL9 (rHuCXCL9). Alternatively, a CXCL9 having a different but closely related amino acid sequence can be administered, for example an amino acid sequence which is at least 70%, 90%, 95%, 97%, 98%, or 99% identical according to a sequence alignment performed using a BLAST algorithm. An antagonist of CXCR3 can also be administered, either instead of CXCL9 or in combination with a CXCL9. Such antagonists are known in the art, and include other chemokines or derivatives of such chemokines that bind CXCR3 without demonstrating intrinsic activity, and molecules that competitively inhibit the binding of CXCL9 to CXCR3. Antagonistic antibodies to either CXCL9 or CXCR3, meaning antibodies which bind the respective antigen and prevent the activation of the normal signal transduction mechanism of CXCR3 within the cell, for example by sterically inhibiting the binding of CXCL9 to CXCR3 are also contemplated by the invention. Yet another form of administering CXCL9 is a eukaryotic expression vector that encodes and expresses CXCL9 of the subject's species. Such an expression vector can produce a transiently heightened expression level for CXCL9 over the desired time window, e.g., for several days prior to administering the chemotherapy or radiotherapy. Such vectors can also be targeted if desired. For example, a preferred method is to perform ex vivo transfection of bone marrow cells using such a vector, and then to return the cells to the patient, e.g., by intravenous injection. Since CXCL9 is a secreted protein, the locus of expression within the body is not a critical factor.

The administration of CXCL9 or a CXCR3 agonist should precede a chemotherapeutic or radiotherapeutic intervention in order to have a beneficial effect. Preferably, CXCL9 or a CXCR3 antagonist is administered for 2 or more days prior to the bone marrow damaging treatment. More preferably, the CXCL9 or CXCR3 is administered for at least 3, at least 5, at least 7, or at least 10 days prior to treatment. Administration can be, for example, by one or more doses per day during the window of time immediately preceding treatment. An additional dose can be administered on the same day as chemotherapy or radiotherapy treatment, or alternatively the final administration can take place one day, two days, or three days or more before the treatment. Long-lasting conjugates, or albumin fusion proteins, of CXCL9 or a CXCR3 agonist also may be administered to improve the effectiveness or reduce the number of doses required. Administration can be by any suitable means. For polypeptides, the preferred means of administration is by intravenous injection; however, other routes can be used as well, including topical formulations, nasal sprays, pills, tablets, caplets, or suppositories. Generally, the administration of CXCL9 or a CXCR3 agonist will terminate when the chemotherapy or radiotherapy is given to the subject; continued administration after such therapy can be harmful, because it can extend the impact on bone marrow cells and impede recovery.

The subject who receives the CXCL9 or CXCR3 agonist therapy is generally one who is scheduled for either chemotherapy or radiotherapy, or can also be a person who is about to be exposed to, or who is at risk for exposure to, a significant amount of bone marrow damaging radiation or chemicals. For example, the subject can be a human patient or an animal who has been diagnosed with a cancer for which chemotherapy or radiation therapy is considered to be an advantageous treatment. Most types of cancer can be treated with either chemotherapy or radiation therapy. Preferred are cancers that have metastasized, or are suspected of having metastasized, and cannot be entirely removed from the body by surgery. A variety of animal models for such cancers are known, which can be used to explore the effectiveness of various agents of the invention, as well as administration and dosing protocols. The subject could also be a person who is about to enter an area characterized by high radiation exposure or chemical exposure, such as associated with space flight or clean-up activities resulting from a radiation spill, nuclear accident, an explosive device or a chemical spill.

The administration of an effective amount of CXCL9 or CXCR3 agonist is accompanied by an improvement of bone marrow condition following the chemotherapy, radiotherapy, or other damaging agent exposure. Bone marrow condition for a subject has improved if one or more of the following occurs: the density of bone marrow cells is greater than if no administration of CXCL9 or CXCR3 agonist was made; the density of progenitor cells or stem cells in bone marrow is greater than if no administration was made; the mass of bone marrow tissue is greater than if no administration was made; or the rate of bone marrow cell proliferation is greater than if no administration was made. The determination of effectiveness can be made at any time following therapy with a chemical or radiation agent. For example, the determination of effectiveness can be made at 1, 2, 3, 4, 5, 6, 7, 8, 9, 10 or more days after the agent (e.g., chemotherapeutic agent) is delivered to the subject. A bone marrow sample can be obtained from any portion of bone marrow in the subject's body for this analysis. In order to compare the result to the expected result if no administration was made, data can be collected from one or more control individuals, preferably from several individuals, who receive the same or similar chemotherapy or radiation therapy, but who do not receive a CXCL9 or CXCR3 agonist. Preferably, the control population is being treated for the same condition, e.g., for the same type of cancer. An amount is an effective amount (e.g., therapeutically effective amount) if any benefit whatsoever is produced compared to the control population. For example, if the treated individual or group has a bone marrow condition parameter, (e.g., proliferation rate of a given progenitor cell type) whose value, or mean value, is closer to the normal value (e.g., higher than) the value or mean value from a control individual or control group, then the bone marrow condition of the treated individual or group is improved. Statistical methods optionally can be applied to this analysis as appropriate. In different embodiments, an effective amount can be an amount that improves bone marrow condition by at least 5%, at least 10%, at least 15%, at least 20%, at least 25%, at least 30%, at least 40%, at least 50% or more.

Another embodiment in accordance with the invention involves the administration of CXCL9 or a CXCR3 agonist as described for the previous embodiment, but with a different measurable outcome. In this embodiment, an effective amount of the CXCL9 or CXCR3 agonist is an increase in peripheral white blood cells. The density (number per unit volume of blood) of white blood cells can be measured by cell counting or by automated methods for determining the number of white blood cells in a sample of whole blood. A blood sample can also be processed to first isolate the white cells prior to counting, or the white cells can be detected using, e.g., labeled antibodies. An effective amount (e.g., therapeutically effective amount) is an amount that produces any increase above a control level either for the total white blood cell population or for any subpopulation thereof.

Yet another embodiment of the invention is a method of treating cancer. For example, the method includes the same administration of CXCL9 or a CXCR3 agonist as discussed above together with the step of subsequently administering either chemotherapy or radiation therapy to the subject. In this embodiment, an effective amount (e.g., therapeutically effective amount) is any amount that treats cancer, meaning that either the safety or effectiveness of the cancer treatment, i.e., the chemotherapy or radiation therapy, is improved compared to the same therapy without CXCL9 or CXCR3 agonist administration.

In a further embodiment, preventive administration of CXCL9 or a CXCR3 agonist before chemotherapy or radiotherapy is supplemented with an effective amount of the post-chemotherapy or post-radiotherapy administration of an agent that is antagonistic to CXCL9 activity. Such agents include, but are not limited to, an antagonistic antibody to CXCL9, an siRNA or antisense nucleic acid specific for CXCL9 expression, an antagonistic antibody to CXCR3 (the natural receptor for the CXCL9 ligand), an siRNA or antisense nucleic acid specific for CXCR3 expression, and an antagonist of CXCR3 function (e.g., a small molecule antagonist). Any of these antagonists of CXCL9 or combinations thereof can be used according to the invention. For human subjects, administration of a fully human antibody to human CXCL9 is especially preferred.

The time course of administration can vary, but it is generally beneficial to adjust it to coincide with the time course of the increased expression of CXCL9 following chemotherapy or radiotherapy. That is, for example, if the subject's CXCL9 expression is expected to peak at about 7 days following chemotherapy, then a CXCL9 antagonistic agent can be administered so as to be present in a therapeutically effective amount by day 7, and optionally for one or more days before and after day 7. The CXCL9 antagonistic agent can be delivered in a single dose or in multiple doses, e.g., in daily doses. The agent can be administered, e.g., only on day 0 (the day of chemotherapy or radiotherapy, or exposure to a bone marrow damaging agent), or on one or more subsequent days, such as on days 0, 1, 2, 3, 4, 5, 6, 7, 8, 9, 10, and later, or on any combination of those days. The agent can also be administered every other day, or can be administered as a long acting conjugate, such as a PEGylated antibody.

In variants of this embodiment, different endpoints can be used to determine an effective dose. As for earlier embodiments, one possible endpoint is an increase in bone marrow cell density compared to a control group who does not receive the CXCL9 antagonistic agent. Another possible endpoint is an increase in peripheral white blood cells. A third endpoint is efficacy in treating cancer, wherein an improvement in either safety or effectiveness of the accompanying cancer therapy, i.e., chemotherapy or radiation therapy, is observed compared to a control group.

In yet other embodiments in accordance with the invention, no CXCL9 or CXCR3 agonist is administered prior to the treatment with a chemotherapy agent or radiation, but after the therapy is performed, an effective amount of a CXCL9 antagonistic agent is administered to the subject. The same factors apply as for the previous embodiments with respect to the type of subject, the time course of administering the agent, the type of agent (i.e., an antagonistic antibody to CXCL9, an siRNA or antisense nucleic acid specific for CXCL9, an antagonistic antibody to CXCR3, an siRNA or antisense nucleic acid specific for CXCR3, or an antagonist of CXCR3), and the type of endpoint for determining an effective amount.

Related to the embodiments described in the previous paragraph are methods of treating a bone marrow disorder characterized by a reduction in bone marrow cells. Such disorders include aplastic anemia, pancytopenia, thrombocytopenia, leucopenia, neutropenia, and myelofibrosis. Each of these diseases exhibits a reduction if one or more types of bone marrow cells. The cause is often exposure to a damaging agent, such as a chemical agent or toxin, radiation, or a virus. The administration of an effective amount of an agent that is antagonistic to CXCL9 relieves the antimyeologenic effect of CXCL9, and leads to an increase in bone marrow cells, which treats the disease. For these methods, an amount of such agent administered that causes any increase in the number or density of bone marrow cells, in bone marrow tissue found anywhere in the body, is an effective amount. In different embodiments, an effective amount can be an amount that increases the number or density of bone marrow cells by at least 5%, at least 10%, at least 15%, at least 20%, at least 25%, at least 30%, at least 40%, at least 50% or more. The schedule of administration can be selected so as to enhance effectiveness, but generally can be a once daily administration, or more or less frequent administration, for a period of 1, 2, 3, 4, 5, 6, 7, 8, 9, 10 or more days, or until an increase in bone marrow cells or a subset of bone marrow cells is observed. Agents that can be administered with these methods include an antagonistic antibody to CXCL9, an siRNA or antisense nucleic acid specific for CXCL9, an antagonistic antibody to CXCR3, an siRNA or antisense nucleic acid specific for CXCR3, or an antagonist of CXCR3.

Further embodiments in accordance with the invention are compositions that can be used in carrying out the methods outlined above. These compositions include one or more agents for administration either prior to or following chemotherapy or radiotherapy, or exposure to a bone marrow damaging agent. The compositions for administration prior to chemotherapy or radiotherapy can contain, for example, a therapeutically effective amount of a CXCL9, a CXCR3 agonist, or an expression vector that expresses a CXCL9, and also a pharmaceutically acceptable carrier. The compositions for administration subsequent to chemotherapy or radiotherapy can contain, for example, a therapeutically effective amount of a CXCL9 antibody, a CXCL9 siRNA or antisense nucleic acid or antisense nucleic acid, a CXCR3 antibody, a CXCR3 siRNA or antisense nucleic acid, or an antagonist of CXCR3, and also a pharmaceutically acceptable carrier. In addition, some embodiments include a kit or pharmaceutical pack containing a therapeutically effective amount of one or more agents for administration prior to chemotherapy or radiotherapy and a therapeutically effective amount of one or more agents for administration following chemotherapy or radiotherapy.

"Isolated," "purified," or "biologically pure" can refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from some open reading frames that naturally flank the gene and encode proteins other than protein encoded by the gene. The term "purified" in some aspects denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other aspects means removing at least one contaminant from the composition to be purified. In this sense, purification does not require that the purified compound be homogenous, e.g., 100% pure.

"Polypeptide," "peptide" and "protein" are used interchangeably herein and can refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

Similarly, "amino acid" can refer to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" or "conservative substitutions" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservative amino acid substitutions" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typical conservative substitutions include any substitution of one member of one of the following groups for another member of the same group: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Recombinant" when used with reference to, e.g., to a cell, or nucleic acid, protein, or vector, can indicate that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operable linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

CXCL9

As used herein, "CXCL9" refers to any mammalian CXCL9 polypeptide, including fragments, mutants, and modifications of a naturally occurring polypeptide, which binds to and activates CXCR3, and includes mature as well as full-length forms. Preferred CXCL9 polypeptides for use in the invention include a human CXCL9 having an amino acid sequence encoded by nucleotides 106 to 417 of SEQ ID NO:10 and a mouse CXCL9 having an amino acid sequence encoded by nucleotides 121 to 438 of SEQ ID NO:9. Modifications of a naturally occurring CXCL9 include conservative amino acid substitutions, insertions, deletions, or truncations resulting in a polypeptide that binds CXCR3 and elicits a CXCR3-mediated response in a target cell.

Expression and Purification of Murine and Human CXCL9

In one aspect the invention provides methods for the expression, refolding, and purification of a mammalian CXCL9 protein. A mammalian CXCL9 can be expressed from prokaryotic cells using an expression vector. One suitable vector for expression in E. coli cells is pET28a (see FIGS. 7 and 12). A nucleotide sequence encoding a mammalian CXCL9, including mouse or human CXCL9, can be inserted into the vector between restriction sites. For example, suitable restriction enzyme sites include NcoI, XhoI, and BamHI. An inducer such as IPTG can be used to induce a high level of expression, leading to the formation of inclusion bodies containing CXCL9 polypeptide. The inclusion bodies can be denatured using urea and refolded by urea removal, e.g., by dilution into urea-free buffer.

The invention further provides a novel one-step purification method for CXCL9. The method can be applied, for example, to recombinant CXCL9 expressed in E. coli and refolded from inclusion bodies. In one aspect the method involves separation of solubilized, refolded CXCL9 inclusion body proteins using cation exchange chromatography. Solubilized, refolded CXCL9 inclusion body proteins are bound to an S Sepharose column at a pH below the pI of the CXCL9, allowing other proteins to wash through the column, and the ionic strength is increased to elute the purified CXCL9 protein. Optionally, the purity of the eluted, purified CXCL9 can be ascertained by a method selected from SDS-PAGE, Western blot, and capillary electrophoresis. Further details of preferred purification CXCL9 methods according to the invention are found in Examples 11 and 12.

Compared with previous methods for purification of rMuCXCL9 (e.g., Zhang et al. [12]), the present methods have the advantages of cost effectiveness, a high purity of >99%, requiring only one chromatography step, and no use of toxic components such as dithiothreitol (DTT). Although DTT stabilizes proteins that possess free sulfhydryl groups during the refolding of recombinant proteins, it may interfere with the redox system. Addition of DTT in the refolding buffer of rMUCXCL9 led to protein aggregation. On the other hand, the purified rMuCXCL9 in the storage buffer without DTT was stable, and its chemoattractant activity was retained for over 3 months at 4° C., even in the present of high salt (NaCl, 0.7-1M).

In some embodiments the amino acid Asp can be added before the mature rMuCXCL9 protein to fit the NcoI site in the vector. Asp is a strongly acidic amino acid and reduces the pI of the protein to 10.52 from 10.62. According to the N-end rule, the in vivo half-life of a protein is related to its N-terminal residue. Thus, a CXCL9 protein with an N-terminal Asp has a half-life of greater than 10 h in E. coli at 36° C., but only 3 min in S. cerevisiae at 30° C. (see Tobias et al. and Varshavsky [19,20]).

CXCR3

CXCR3 is a shared receptor for several natural ligands, including CXC chemokines like IP-10, Mig, I-TAC and BCA-1. CXCR3 is a G-protein coupled receptor. CXCR3 is expressed, for example, on the surfaces of monocytes and Th1 cells.

The term "CXCR3 agonist" is used herein to refer to substances that bind to CXCR3 and promote the activity of CXCR3, in particular the activity produced in a cell when CXCL9 binds to and activates CXCR3. CXCR3 agonists include natural ligands for CXCR3 such as IP-10, Mig, I-TAC, and BCA-1 (as well as biologically active fragments and modifications thereof), and also includes both known and novel compounds that possess agonist activity with respect to CXCR3. Preferably, a CXCR3 agonist is selected from the group consisting of IP-10, Mig, I-TAC, BCA-1, modifications and prodrugs thereof. Exemplary agonists of CXCR3 are generally described in U.S. Pat. No. 6,184,358, International Publication No. WO 2005/113597, WO 2004/083394 and U.S. Publication No. 2005/0119174.

The term "CXCR3 antagonist" includes substances that bind to CXCR3 but do not promote the activity of CXCR3 in a cell, and may block or inhibit the activity of CXCR3, either acting alone or in the presence of a natural ligand or agonist of CXCR3, and also includes substances that bind to a natural ligand of CXCR3 and prevent it from binding to CXCR3 or activating CXCR3. CXCR3 antagonists can be neutral antagonists, for example, which block the activity of CXCR3 by inhibiting the binding of physiological ligands to CXCR3, or inverse agonists, which shift the equilibrium of the active form and inactive form of CXCR3 toward the more inactive form. CXCR3 antagonists encompass both known and novel compounds that possess any one of the above-described properties. Examples of CXCR3 antagonists include degradation products of physiological ligands for CXCR3 such as IP-10, Mig, I-TAC, and BCA-1; certain kinds of CC chemokines that possess affinity for CXCR3, such as eotaxin (J. Biol. Chem., 273(29): 18288-18291 (1998)). Further exemplary antagonists of CXCR3, including small molecule agonists, are generally described in International Publication Nos. WO 2006/088920, WO 2006/088837, WO 2006/091428, WO 2006/088921, WO 2006/088919, WO 2006/088836, WO 2007/002742, WO 2007/002701, WO 2006/137934, WO 2006/129679, WO 2005/113597, WO 2002/085861, U.S. Publication Nos. 2006/0240437, 2006/0204498, 2006/0276480, 2006/0276479, 2006/0276448, 2006/0276457, 2006/0217392, 2007/0021611, 2007/0015773, 2005/0119174, 2004/0242498, 2003/0077247, 2002/0018776, 2002/0169159 and European Publication Nos. EP 1603896, EP 1723970.

The amino acid sequences of IP-10, Mig, I-TAC and BCA-1, which are physiological ligands for CXCR3, and the nucleotide sequences of their genes are known. For example, the human cDNA sequences of these ligands have been registered with GenBank under accession numbers NM 001565, NM 002416, NM 005409, and NM 006419, respectively. In the present invention, "IP-10", "Mig", "I-TAC", and "BCA-1" encompass, in addition to the corresponding naturally occurring chemokine proteins derived from humans and other mammals, recombinant proteins produced from recombinant cells containing DNAs that encode them.

CXCR3 agonists or antagonists can also be used in the form of a prodrug that is metabolized in the body of a recipient animal and results in a substance that exhibits the respective agonist or antagonist activity with respect to CXCR3. When the CXCR3 agonist or antagonist is a peptide substance such as IP-10, Mig, I-TAC or BCA-1, "prodrugs" thereof also encompass an expression vector containing a nucleic acid sequence that encodes the peptide, and a host cell transfected with such an expression vector. In the expression vector, a DNA that encodes a physiological ligand possessing agonist or antagonist activity against CXCR3, such as IP-10, Mig, I-TAC or BCA-1, or a modification thereof, is operably linked to a promoter capable of exhibiting promoter activity in the cells of the recipient mammal.

Antibodies

An antibody of the invention includes an immunoglobulin molecule immunologically reactive with a particular antigen, and includes both polyclonal and monoclonal antibodies. An antibody of the invention also includes genetically engineered forms such as chimeric antibodies (e.g., humanized murine antibodies) and heteroconjugate antibodies (e.g., bispecific antibodies). Antibodies also include antigen-binding forms of antibodies, including fragments with antigen-binding capability (e.g., Fab', F(ab')$_2$, Fab, Fv and rIgG. See also, Pierce Catalog and Handbook, 1994-1995 (Pierce Chemical Co., Rockford, Ill.). See also, e.g., Kuby, J., Immunology, 3rd Ed., W. H. Freeman & Co., New York (1998). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) J. Immunol. 148:1547, Pack and Pluckthun (1992) Biochemistry 31:1579, Hollinger et al., 1993, supra, Gruber et al. (1994) J. Immunol.: 5368, Zhu et al., (1997) Protein Sci. 6:781, Hu et al., (1996) Cancer Res. 56:3055, Adams et al., (1993) Cancer Res. 53:4026, and McCartney et al., (1995) Protein Eng. 8:301.

An antibody immunologically reactive with a particular antigen can be generated by recombinant methods such as selection of libraries of recombinant antibodies in phage or similar vectors, see, e.g., Huse et al., Science 246:1275-1281 (1989); Ward et al., Nature 341:544-546 (1989); and Vaughan et al., Nature Biotech. 14:309-314 (1996), or by immunizing an animal with the antigen or with DNA encoding the antigen.

Typically, an immunoglobulin has a heavy and light chain. Each heavy and light chain contains a constant region and a variable region, (the regions are also known as "domains"). Light and heavy chain variable regions contain four "framework" regions interrupted by three hypervariable regions, also called "complementarity-determining regions" or "CDRs." The extent of the framework regions and CDRs have been defined. The sequences of the framework regions of different light or heavy chains are relatively conserved within a species. The framework regions of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or a "$V_H$" refer to the variable region of an immunoglobulin heavy chain of an antibody, including the heavy chain of an Fv, scFv, dsFv (disulfide-stabilized Fv) or Fab. References to "$V_L$" or a "$V_L$" refer to the variable region of an immunoglobulin light chain, including the light chain of an Fv, scFv, dsFv or Fab.

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active antigen binding site.

In one aspect, an antibody of the invention can be a "chimeric antibody". For example, a chimeric antibody is an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one aspect, an antibody of the invention can be a "humanized antibody." For example, a humanized antibody is an immunoglobulin molecule which contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al., Nature 321:522-525 (1986); Riechmann et al., Nature 332:323-329 (1988); and Presta, Curr. Op. Struct. Biol. 2:593-596 (1992)). Humanization can be essentially performed following the method of Winter and co-workers (Jones et al., Nature 321:522-525 (1986); Riechmann et al., Nature 332:323-327 (1988); Verhoeyen et al., Science 239:1534-1536 (1988)), by substituting rodent CDRs or CDR sequences for the corresponding sequences of a human antibody. Accordingly, such humanized antibodies are chimeric antibodies (U.S. Pat. No. 4,816, 567), wherein substantially less than an intact human variable domain has been substituted by the corresponding sequence from a non-human species.

In one aspect, an antibody of the invention can be a "human antibody" or "fully human antibody," which can refer to an immunoglobulin comprising human variable regions in addition to human framework and constant regions. Such antibodies can be produced using various techniques known in the art. For example in vitro methods involve use of recombinant libraries of human antibody fragments displayed on bacteriophage (e.g., McCafferty et al., 1990, Nature 348:552-554; Hoogenboom & Winter, J. Mol. Biol. 227:381 (1991); and Marks et al., J. Mol. Biol. 222:581 (1991)), yeast cells (Boder and Wittrup, 1997, Nat. Biotechnol. 15:553-557), or ribosomes (Hanes and Pluckthun, 1997, Proc. Natl. Acad. Sci. USA 94:4937-4942). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 6,150,584, 5,545,807; 5,545,806; 5,569,825; 5,625,126; 5,633,425; 5,661,016, and in the following scientific publications: (e.g., Jakobavits, Adv. Drug. Deliv. Rev. 31:33-42 (1998), Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); Lonberg & Huszar, Intern. Rev. Immunol. 13:65-93 (1995).

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, at least 6, or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

Antigen or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen.". Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

An antibody of the invention can be bound (or linked, or conjugated), either covalently, through a linker or a chemical bond, or noncovalently, through ionic, van der Waals, electrostatic, or hydrogen bonds, to an effector molecule. The effector molecule can be a variety of molecules including, e.g., detection moieties including radioactive compounds, fluorescent compounds, an enzyme or substrate, tags such as epitope tags, a toxin; activatable moieties, a chemotherapeutic agent; a lipase; an antibiotic; or a radioisotope emitting "hard" e.g., beta radiation.

For example, an antibody of the invention can be conjugated to a "label" or a "detectable moiety". Generally, a label or detectable moiety can be a composition detectable by spectroscopic, photochemical, biochemical, immunochemical, chemical, or other physical means. For example, useful labels include fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The radioisotope may be, for example, $^3H$, $^{14}C$, $^{32}P$, $^{35}S$, or $^{125}I$. In some cases, particularly using antibodies against the proteins of the invention, the radioisotopes are used as toxic moieties, as described below. The labels may be incorporated into the nucleic acids, proteins and antibodies at any position. Any method known in the art for conjugating the antibody to the label may be employed, including those methods described by Hunter et al., Nature, 144:945 (1962); David et al., Biochemistry, 13:1014 (1974); Pain et al., J. Immunol. Meth., 40:219 (1981); and Nygren, J. Histochem. and Cytochem., 30:407 (1982). The lifetime of radiolabeled peptides or radiolabeled antibody compositions may extended by the addition of substances that stabilize the radiolabeled peptide or antibody and protect it from degradation. Any substance or combination of substances that stabilize the radiolabeled peptide or antibody may be used including those substances disclosed in U.S. Pat. No. 5,961,955.

The phrase "specifically (or selectively) binds" to an antibody or antigen, such as a protein, preferably a CXCL9 protein or "specifically (or selectively) immunoreactive with," when referring to a protein or peptide or antibody, can refer to a binding reaction that is determinative of the presence of the protein in a heterogeneous population of proteins and other biologics. Thus, under designated immunoassay conditions, the specified antibodies bind to a particular protein at least two times the background and more typically more than 10 to 100 times background.

Antibodies that are immunoreactive with CXCL9 proteins and not with other proteins can be prepared, for example, by subtracting out antibodies that cross-react with other molecules. A variety of immunoassay formats may be used to select antibodies specifically immunoreactive with a particular protein. For example, solid-phase ELISA immunoassays are routinely used to select antibodies immunoreactive only with a particular protein (see, e.g., Harlow & Lane, Antibodies, A Laboratory Manual (1988) for a description of immunoassay formats and conditions that can be used to determine specific immunoreactivity).

Dosage and frequency of the administration of antibodies vary depending on the half-life of the antibody in the patient. The half-life of a CXCL9 or CXCR3 antibody can also be prolonged via fusion to a stable polypeptide or moiety, e.g., albumin or PEG. The methods and techniques for producing fusion antibodies are well known in the art and can be used in conjunction with an antibody of the invention. Examples of method and techniques for producing a fusion protein or antibody are generally described by U.S. Pat. Nos. 7,081,354, 6,972,322, 7,041,478 and 6,987,006.

In general, humanized antibodies show the longest half-life, followed by chimeric antibodies and nonhuman antibodies. In one aspect, the antibody, or antigen-binding fragments, variants, or derivatives thereof of the invention can be administered in unconjugated form. In another aspect, the antibody, or antigen-binding fragments, variants, or derivatives thereof of the invention can be administered multiple times in conjugated form. In still another aspect, the antibodies, or antigen-binding fragments, variants, or derivatives thereof of the invention can be administered in unconjugated form, then in conjugated form, or vice versa.

Generation of Recombinant Antibodies

Using the nucleic acids of the invention, anti CXCL9 monoclonal antibodies can be produced recombinantly. In a preferred aspect, a chimeric or humanized anti-CXCL9 monoclonal antibody is produced recombinantly. Recombinant DNA technology may be employed wherein a nucleotide sequence that encodes an anti-CXCL9 monoclonal antibody or a fragment thereof, such as one or more CDR sequences, is inserted into an expression vector, transformed or transfected into an appropriate host cell and cultivated under conditions suitable for expression. These procedures are generally known in the art, as described generally in Sambrook et al., Molecular Cloning, A Laboratory Manual, Cold Spring Harbor Press, Cold Spring Harbor, N.Y. (1982). "Vector" can refer to any type of genetic construct containing a nucleic acid capable of being transcribed in a cell. Vectors used for the amplification of nucleotide sequences (both coding and non-coding) are also encompassed by the definition. In addition to the coding sequence, vectors will generally include restriction enzyme cleavage sites and the other initial, terminal and intermediate DNA sequences that are usually employed in vectors to facilitate their construction and use. The expression vector can be part of a plasmid, virus, or nucleic acid fragment.

Coding sequences for the anti-CXCL9 monoclonal antibodies of the present invention or fragments and CDR sequences thereof may be synthesized by chemical techniques, for example, the phosphotriester method of Matteucci et al. (J. Am. Chem. Soc. 1981, 103:3185). The term "coding sequence", in relation to nucleic acid sequences, refers to a plurality of contiguous sets of three nucleotides, termed codons, each codon corresponding to an amino acid as translated by biochemical factors according to the universal genetic code, the entire sequence coding for an expressed protein, or an antisense strand that inhibits expression of a protein. A "genetic coding sequence" is a coding sequence where the contiguous codons are intermittently interrupted by non-coding intervening sequences, or "introns." During mRNA processing intron sequences are removed, restoring the contiguous codon sequence encoding the protein.

Any modification within a DNA or RNA sequence can be made simply by substituting the appropriate bases for those encoding the desired amino acid sequence. The coding sequence can then be provided with appropriate linkers and ligated into expression vectors commonly available in the art, and the vectors used to transform suitable hosts to produce the immunostimulating peptide or protein. A number of such vectors and suitable host systems are commercially available. For expression, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Of course, yeast or mammalian cell hosts may also be used, employing suitable vectors and control sequences as known to the skilled artisan.

Derivatized Antibodies

An antibody for use in the invention can be, in addition to a natural immunoglobulin, any antigen-binding fragment of an immunoglobulin or a modified immunoglobulin or antigen-binding fragment. Antibodies can be modified, for example, by the covalent attachment of an organic moiety. Such modification can produce an antibody with improved pharmacokinetic properties (e.g., increased in vivo plasma half-life). The organic moiety can be a linear or branched hydrophilic polymeric group, fatty acid group, or fatty acid ester group. In particular embodiments, the hydrophilic polymeric group can have a molecular weight of about 800 to about 120,000 daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

An antibody for use in the invention can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. A fatty acid can be a mono-carboxylic acid or a di-carboxylic acid. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody has a molecular weight of about 800 to about 150,000 Daltons as a separate molecular entity. For example PEG5000 and PEG20,000 wherein the subscript is the average molecular weight of the polymer in daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for antibodies of the invention can be saturated or can contain one or more units of unsaturation. Fatty acids that are suitable for modifying antibodies of the invention include, for example, n-dodecanoate (C12, laurate), n-tetradecanoate (C14, myristate), n-octadecanoate (C18, stearate), n-eicosanoate (C20, arachidate), n-docosanoate (C22, behenate), n-triacontanoate (C30), n-tetracontanoate (C40), cis-.DELTA.9-octadecanoate (C18, oleate), all cis-.DELTA.5,8,11,14-eicosatetraenoate (C20, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The antibodies can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., Bioconjugate Techniques, Academic Press: San Diego, Calif. (1996)). An activating group can be bonded directly to the organic group (e.g., hydrophilic polymer, fatty acid, fatty acid ester), or through a linker moiety, for example a divalent C1-C12 group wherein one or more carbon atoms can be replaced by a heteroatom such as oxygen, nitrogen or sulfur. Suitable linker moieties include, for example, tetraethylene glycol, —(CH$_2$)$_3$—, —NH—(CH$_2$)$_6$—NH—, —(CH$_2$)$_2$—NH— and —CH$_2$—O—CH$_2$—CH$_2$—O—CH$_2$—CH$_2$—O—CH—NH—.

Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference.)

Conjugated antibodies of the invention can be produced by reacting a antibody or antigen-binding fragment with a modifying agent. For example, the organic moieties can be bonded to the antibody in a non-site specific manner by employing an amine-reactive modifying agent, for example, an NHS ester of PEG. Conjugated antibodies or antigen-binding fragments can also be prepared by reducing disulfide bonds (e.g., intrachain disulfide bonds) of an antibody or antigen-binding fragment. The reduced antibody or antigen-binding fragment can then be reacted with a thiol-reactive modifying agent to produce the modified antibody of the invention. Conjugated antibodies and antigen-binding fragments comprising an organic moiety that is bonded to specific sites of an antibody of the present invention can be prepared using suitable methods, such as reverse proteolysis (Fisch et al., Bioconjugate Chem., 3:147-153 (1992); Werlen et al., Bioconjugate Chem., 5:411-417 (1994); Kumaran et al., Protein Sci. 6(10):2233-2241 (1997); Itoh et al., Bioorg. Chem., 24(1): 59-8 (1996); Capellas et al., Biotechnol. Bioeng., 56(4):456-463 (1997)), and the methods described in Hermanson, G. T., Bioconjugate Techniques, Academic Press: San Diego, Calif. (1996). Other methods and techniques for conjugating antibodies that can be performed with the antibodies of the invention are generally described by U.S. Pat. Nos. 6,426,086, 6,071,533, 6,214,388, 4,429,008 and European Patent No. EP172435.

Binding Affinity of Antibodies

Binding affinity for a target antigen is typically measured or determined by standard antibody-antigen assays, such as Biacore competitive assays, saturation assays, or immunoassays such as ELISA or RIA.

Such assays can be used to determine the dissociation constant of the antibody. The phrase "dissociation constant" refers to the affinity of an antibody for an antigen. Specificity of binding between an antibody and an antigen exists if the dissociation constant ($K_D$=1/K, where K is the affinity constant) of the antibody is <1 µM, preferably <100 nM, and most preferably <0.1 nM. Antibody molecules will typically have a $K_D$ in the lower ranges. $K_D$=[Ab–Ag]/[Ab][Ag] where [Ab] is the concentration at equilibrium of the antibody, [Ag] is the concentration at equilibrium of the antigen and [Ab–Ag] is the concentration at equilibrium of the antibody-antigen complex. Typically, the binding interactions between antigen and antibody include reversible noncovalent associations such as electrostatic attraction, Van der Waals forces and hydrogen bonds.

The antibodies of the invention specifically bind to CXCL9 proteins. By "specifically bind" herein is meant that the antibodies bind to the CXCL9 protein with a $K_D$ of at least about 0.1 mM, more usually at least about 1 µM, preferably at least about 0.1 µM or better, and most preferably, 0.01 µM or better.

Small Interfering RNA (siRNA)

A small interfering RNA (siRNA) is an RNA molecule comprising a set of nucleotides that is targeted to a gene or polynucleotide of interest. As used herein, the term "siRNA" encompasses all forms of siRNA including, but not limited to (i) a double stranded RNA polynucleotide, (ii) a single stranded polynucleotide, and (iii) a polynucleotide of either (i) or (ii) wherein such a polynucleotide, has one, two, three, four or more nucleotide alterations or substitutions therein.

An siRNA in the form of a double stranded polynucleotide comprises about 18 base pairs, about 19 base pairs, about 20 base pairs, about 21 base pairs, about 22 base pairs, about 23 base pairs, about 24 base pairs, about 25 base pairs, about 26 base pairs, about 27 base pairs, about 28 base pairs, about 29 base pairs or about 30 base pairs in length. The double stranded siRNA is capable of interfering with the expression and/or the activity of a CXCL9.

A single stranded siRNA comprises a portion of an RNA polynucleotide sequence that is targeted to a gene or polynucleotide of interest. A single stranded siRNA comprises a polynucleotide of about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides or about 30 nucleotides in length. The single stranded siRNA is capable of interfering with expression and/or activity of a target polynucleotide or a variant thereof. The single strand siRNA is also capable of annealing to a complementary sequence to result in a dsRNA that is capable of interfering with the expression and/or the activity of a CXCL9.

In yet another aspect, the siRNA comprises a polynucleotide comprising either a double stranded or a single stranded polynucleotide, wherein the siRNA has one, two, three, four or more nucleotide alterations or substitutions therein.

An siRNA polynucleotide is an RNA nucleic acid molecule that interferes with RNA activity that is generally considered to occur via a post-transcriptional gene silencing mechanism. An siRNA polynucleotide preferably comprises a double-stranded RNA (dsRNA) but is not intended to be so limited and may comprise a single-stranded RNA (see, e.g., Martinez et al., 2002 Cell 110:563-74). The siRNA polynucleotide included in the invention may comprise other naturally occurring, recombinant, or synthetic single-stranded or double-stranded polymers of nucleotides (ribonucleotides or deoxyribonucleotides or a combination of both) and/or nucleotide analogues as provided herein (e.g., an oligonucleotide or polynucleotide or the like, typically in 5' to 3' phosphodiester linkage). Accordingly it will be appreciated that exemplary sequences disclosed as DNA sequences capable of directing the transcription of the siRNA polynucleotides are also intended to describe the corresponding RNA sequences and their complements, given the well established principles of complementary nucleotide base-pairing.

An siRNA may be transcribed using as a template a DNA (genomic, cDNA, or synthetic) that contains a promoter for an RNA polymerase promoter. For example, the promoter can be the U6 promoter or the H1 RNA polymerase III promoter. Alternatively, the siRNA may be a synthetically derived RNA molecule. In certain aspects, the siRNA polynucleotide may have blunt ends. In certain other aspects, at least one strand of the siRNA polynucleotide has at least one, and preferably two nucleotides that "overhang" (i.e., that do not base pair with a complementary base in the opposing strand) at the 3' end of either strand of the siRNA polynucleotide. In a preferred aspect of the invention, each strand of the siRNA polynucleotide duplex has a two-nucleotide overhang at the 3' end. The two-nucleotide overhang is preferably a thymidine dinucleotide (TT) but may also comprise other bases, for example, a TC dinucleotide or a TG dinucleotide, or any other dinucleotide. The overhang dinucleotide may also be complementary to the two nucleotides at the 5' end of the sequence of the polynucleotide that is targeted for interference. For a discussion of 3' ends of siRNA polynucleotides see, e.g., International Publication No. WO 01/75164.

Preferred siRNA polynucleotides comprise double-stranded polynucleotides of about 18-30 nucleotide base pairs, preferably about 18, about 19, about 20, about 21, about 22, about 23, about 24, about 25, about 26, or about 27 base pairs, and in other preferred aspects about 19, about 20, about 21, about 22 or about 23 base pairs, or about 27 base pairs, whereby the use of "about" indicates that in certain aspects and under certain conditions the processive cleavage steps that may give rise to functional siRNA polynucleotides that are capable of interfering with expression of a selected polypeptide may not be absolutely efficient. Hence, siRNA polynucleotides, may include one or more siRNA polynucleotide molecules that may differ (e.g., by nucleotide insertion or deletion) in length by one, two, three, four or more base pairs as a consequence of the variability in processing, in biosynthesis, or in artificial synthesis of the siRNA. The siRNA polynucleotide of the present invention may also comprise a polynucleotide sequence that exhibits variability by differing (e.g., by nucleotide substitution, including transition or transversion) at one, two, three or four nucleotides from a particular sequence. These differences can occur at any of the nucleotide positions of a particular siRNA polynucleotide sequence, depending on the length of the molecule, whether situated in a sense or in an antisense strand of the double-stranded polynucleotide. The nucleotide difference may be found on one strand of a double-stranded polynucleotide, where the complementary nucleotide with which the substitute nucleotide would typically form hydrogen bond base pairing, may not necessarily be correspondingly substituted. In preferred aspects, the siRNA polynucleotides are homogeneous with respect to a specific nucleotide sequence.

Polynucleotides that comprise the siRNA polynucleotides of the present invention may in certain aspects be derived from a single-stranded polynucleotide that comprises a single-stranded oligonucleotide fragment (e.g., of about 18-30 nucleotides) and its reverse complement, typically separated by a spacer sequence. According to certain such aspects, cleavage of the spacer provides the single-stranded oligonucleotide fragment and its reverse complement, such that they may anneal to form, optionally with additional processing steps that may result in addition or removal of one, two, three or more nucleotides from the 3' end and/or the 5' end of either or both strands, the double-stranded siRNA polynucleotide of the present invention. In certain aspects the spacer is of a length that permits the fragment and its reverse complement to anneal and form a double-stranded structure (e.g., like a hairpin polynucleotide) prior to cleavage of the spacer, and optionally, subsequent processing steps that may result in addition or removal of one, two, three, four, or more nucleotides from the 3' end and/or the 5' end of either or both strands. A spacer sequence may therefore be any polynucleotide sequence as provided herein that is situated between two complementary polynucleotide sequence regions which, when annealed into a double-stranded nucleic acid, result in an siRNA polynucleotide. Preferably, the spacer sequence comprises at least 4 nucleotides. In certain aspects, the spacer may comprise 5, 6, 7, 8, 9, 10, 11, 12, 13, 14, 15, 16, 17, 18, 19, 20, 21-25, 26-30, 31-40, 41-50, 51-70, 71-90, 91-110, 111-150, 151-200 or more nucleotides. Examples of siRNA polynucleotides derived from a single nucleotide strand comprising two complementary nucleotide sequences separated by a spacer have been described (e.g., Brummelkamp et al., 2002 Science 296:550; Paddison et al., 2002 Genes Develop. 16:948; Paul et al., 2002 Nat. Biotechnol. 20:505-508; Grabarek et al., 2003 BioTechniques 34:734-44).

Polynucleotide variants may contain one or more substitutions, additions, deletions, and/or insertions such that the activity of the siRNA polynucleotide is not substantially diminished. The effect of any such alterations in nucleotide content on the activity of the siRNA polynucleotide may generally be assessed as described elsewhere herein. Variants preferably exhibit at least about 75%, 78%, 80%, 85%, 87%, 88% or 89% identity and more preferably at least about 90%, 92%, 95%, 96%, or 97% identity to a portion of a polynucleotide sequence that encodes a native CXCL9. The percent identity may be readily determined by comparing sequences of the polynucleotides to the corresponding portion of the target polynucleotide, using any method including using computer algorithms well known to those having ordinary skill in the art. These include the Align or the BLAST algorithm (Altschul, 1991 J. Mol. Biol. 219:555-565; Henikoff and Henikoff, 1992, Proc. Natl. Acad. Sci. USA 89:10915-10919).

Certain siRNA polynucleotide variants can be substantially homologous to a portion of a polynucleotide encoding a target polypeptide. Single-stranded polynucleotides derived from these polynucleotide variants are capable of hybridizing under moderately stringent conditions to a naturally occurring DNA or RNA sequence encoding the target polypeptide. An siRNA polynucleotide that detectably hybridizes to the polynucleotide sequence encoding the target polypeptide under moderately stringent conditions may have a nucleotide sequence that includes at least 10 consecutive nucleotides, more preferably 11, 12, 13, 14, 15, 16, 17, 18, 19, 20, 21, 22, 23, 24, 25, 26, 27, 28, 29 or 30 consecutive nucleotides that are complementary to a particular target polynucleotide. In certain preferred aspects, such an siRNA sequence (or its complement) will be unique to a single particular polynucleotide encoding the target polypeptide for which interference with expression is desired. In certain other aspects, the sequence (or its complement) may be shared by two or more related polynucleotides encoding the target polypeptide for which interference with polypeptide expression is desired.

Suitable moderate stringent conditions include, for example, pre-washing the polynucleotide in a solution of 5×SSC, 0.5% SDS, 1.0 mM EDTA (pH 8.0); hybridizing the polynucleotide at 50° C.-70° C., 5×SSC for 1-16 hours (e.g., overnight); followed by washing the polynucleotide once or twice at 22-65° C. for 20-40 minutes with one or more each of 2×, 0.5× and 0.2×SSC containing 0.05-0.1% SDS. For additional stringency, hybridization conditions may include an additional wash in 0.1×SSC and 0.1% SDS at 50-60° C. for 15-40 minutes. Those of ordinary skill in the art will understand that, variations in stringency of hybridization conditions may be achieved by altering the time, temperature, and/or concentration of the solutions used for the pre-hybridization, hybridization, and wash steps. Suitable conditions may also depend in part on the particular nucleotide sequences of the probe used, and of the blotted, proband nucleic acid sample. Accordingly, it will be appreciated that suitably stringent conditions can be readily selected, without undue experimentation, when a desired selectivity of the polynucleotide is identified, based on its ability to hybridize to one or more certain proband sequences while not hybridizing to certain other proband sequences.

Sequence specific siRNA polynucleotides of the present invention may be designed using one or more of several criteria. For example, to design an siRNA polynucleotide that has about 21 consecutive nucleotides identical to a sequence encoding a polypeptide of interest, the open reading frame of the polynucleotide sequence may be scanned for about 21-base sequences length that have one or more of the following characteristics: (1) an A+T/G+C ratio of approximately 1:1 but no greater than 2:1 or 1:2; (2) an AA dinucleotide or a CA dinucleotide at the 5' end; (3) an internal hairpin loop melting temperature less than 55° C.; (4) a homodimer melting temperature of less than 37° C. (melting temperature calculations as described in (3) and (4) can be determined using computer software known to those skilled in the art); (5) a sequence of at least 16 consecutive nucleotides not identified as being present in any other known polynucleotide sequence. Alternatively, an siRNA polynucleotide sequence may be designed and chosen using a computer software available commercially from various vendors, e.g., OligoEngine™ (Seattle, Wash.); Dharmacon, Inc. (Lafayette, Colo.); Ambion Inc. (Austin, Tex.); and QIAGEN, Inc. (Valencia, Calif.)). See also Elbashir et al., 2000 Genes & Development 15:188-200; Elbashir et al., 2001 Nature 411:494-98. The siRNA polynucleotide may then be tested for the ability to interfere with the expression of the target polypeptide according to methods known in the art and described elsewherein herein. The determination of the effectiveness of an siRNA polynucleotide includes not only consideration of its ability to interfere with the expression of the target polypeptide, but also whether the siRNA polynucleotide is toxic to the host cell. For example, a desirable siRNA would exhibit an RNA interference activity and would also not exhibit an unwanted biological consequence. An example of an unwanted biological consequence is apoptosis of a cell for which cell death is not a desired as a result of the introduction of the siRNA into the host cell.

Based on the present disclosure, it should be appreciated that the siRNAs of the present invention may effect silencing of the target polypeptide expression to different degrees. The siRNAs thus must first be tested for their effectiveness. Selection of siRNAs are made therefrom based on the ability of a given siRNA to interfere with or modulate the expression of the target polypeptide. Accordingly, identification of specific siRNA polynucleotide sequences that are capable of interfering with expression of a desired target polypeptide requires production and testing of each siRNA. The methods for testing each siRNA and selection of suitable siRNAs for use in the present invention are fully set forth herein the Examples. Since not all siRNAs that interfere with protein expression will have a physiologically important effect, the present disclosure also sets forth various physiologically relevant assays for determining whether the levels of interference with target protein expression using the siRNAs of the invention have clinically relevant significance.

Polynucleotides of the siRNA may be prepared using any of a variety of techniques, which are useful for the preparation of specifically desired siRNA polynucleotides. For example, a polynucleotide may be amplified from a cDNA prepared from a suitable cell or tissue type. Such a polynucleotide may be amplified via polymerase chain reaction (PCR). Using this approach, sequence-specific primers are designed based on the sequences provided herein, and may be purchased or synthesized directly. An amplified portion of the primer may be used to isolate a full-length gene, or a desired portion thereof, from a suitable DNA library using well known techniques. A library (cDNA or genomic) is screened using one or more polynucleotide probes or primers suitable for amplification. Preferably, the library is size-selected to include larger polynucleotide sequences. Random primed libraries may also be preferred in order to identify 5' and other upstream regions of the genes. Genomic libraries are preferred for obtaining introns and extending 5' sequences. The siRNA polynucleotide contemplated by the present invention may also be selected from a library of siRNA polynucleotide sequences.

For hybridization techniques, a partial polynucleotide sequence may be labeled (e.g., by nick-translation or end-labeling with $^{32}P$) using well known techniques. A bacterial or bacteriophage library may then be screened by hybridization to filters containing denatured bacterial colonies (or lawns containing phage plaques) with the labeled probe (see, e.g., Sambrook et al., Molecular Cloning: A Laboratory Manual, Cold Spring Harbor Laboratories, Cold Spring Harbor, N.Y., 2001). Hybridizing colonies or plaques are selected and expanded, and the DNA is isolated for further analysis.

Alternatively, numerous amplification techniques are known in the art for obtaining a full-length coding sequence from a partial cDNA sequence. Within such techniques, amplification is generally performed via PCR. One such technique is known as "rapid amplification of cDNA ends" or RACE (see, e.g., Sambrook et al., Molecular Cloning: A Laboratory Manual, Cold Spring Harbor Laboratories, Cold Spring Harbor, N.Y., 2001).

A number of specific siRNA polynucleotide sequences useful for interfering with target polypeptide expression are presented in the Examples, the Drawings, and in the Sequence Listing included herein. siRNA polynucleotides may generally be prepared by any method known in the art, including, for example, solid phase chemical synthesis. Modifications in a polynucleotide sequence may also be introduced using standard mutagenesis techniques, such as oligonucleotide-directed site-specific mutagenesis. Further, siRNAs may be chemically modified or conjugated with other molecules to improve their stability and/or delivery properties. Included as one aspect of the invention are siRNAs as described herein, wherein one or more ribose sugars has been removed therefrom.

Alternatively, siRNA polynucleotide molecules may be generated by in vitro or in vivo transcription of suitable DNA sequences (e.g., polynucleotide sequences encoding a target polypeptide, or a desired portion thereof), provided that the DNA is incorporated into a vector with a suitable RNA polymerase promoter (such as for example, T7, U6, H1, or SP6 although other promoters may be equally useful). In addition, an siRNA polynucleotide may be administered to a mammal, as may be a DNA sequence (e.g., a recombinant nucleic acid construct as provided herein) that supports transcription (and optionally appropriate processing steps) such that a desired siRNA is generated in vivo.

In one aspect, an siRNA polynucleotide, wherein the siRNA polynucleotide is capable of interfering with expression of a target polypeptide can be used to generate a silenced cell. Any siRNA polynucleotide that, when contacted with a biological source for a period of time, results in a significant decrease in the expression of the target polypeptide is included in the invention. Preferably the decrease is greater than about 10%, more preferably greater than about 20%, more preferably greater than about 30%, more preferably greater than about 40%, about 50%, about 60%, about 70%, about 75%, about 80%, about 85%, about 90%, about 95% or about 98% relative to the expression level of the target polypeptide detected in the absence of the siRNA. Preferably, the presence of the siRNA polynucleotide in a cell does not result in or cause any undesired toxic effects, for example, apoptosis or death of a cell in which apoptosis is not a desired effect of RNA interference.

In another aspect, the siRNA polynucleotide that, when contacted with a biological source for a period of time, results in a significant decrease in the expression of the target polypeptide. Preferably the decrease is about 10%-20%, more preferably about 20%-30%, more preferably about 30%-40%, more preferably about 40%-50%, more preferably about 50%-60%, more preferably about 60%-70%, more preferably about 70%-80%, more preferably about 80%-90%, more preferably about 90%-95%, more preferably about 95%-98% relative to the expression level of the target polypeptide detected in the absence of the siRNA. Preferably, the presence of the siRNA polynucleotide in a cell does not result in or cause any undesired toxic effects.

In yet another aspect, the siRNA polynucleotide that, when contacted with a biological source for a period of time, results in a significant decrease in the expression of the target polypeptide. Preferably the decrease is about 10% or more, more preferably about 20% or more, more preferably about 30% or more, more preferably about 40% or more, more preferably about 50% or more, more preferably about 60% or more, more preferably about 70% or more, more preferably about 80% or more, more preferably about 90% or more, more preferably about 95% or more, more preferably about 98% or more relative to the expression level of the target polypeptide detected in the absence of the siRNA. Preferably, the presence of the siRNA polynucleotide in a cell does not result in or cause any undesired toxic effects.

Following the generation of the siRNA polynucleotide of the present invention, a skilled artisan will understand that the siRNA polynucleotide will have certain characteristics that can be modified to improve the siRNA as a therapeutic compound. Therefore, the siRNA polynucleotide may be further designed to resist degradation by modifying it to include phosphorothioate, or other linkages, methylphosphonate, sulfone, sulfate, ketyl, phosphorodithioate, phosphoramidate, phosphate esters, and the like (see, e.g., Agrwal et al., 1987 Tetrahedron Lett. 28:3539-3542; Stec et al., 1985 Tetrahedron Lett. 26:2191-2194; Moody et al., 1989 Nucleic Acids Res. 12:4769-4782; Eckstein, 1989 Trends Biol. Sci. 14:97-100; Stein, In: Oligodeoxynucleotides. Antisense Inhibitors of Gene Expression, Cohen, ed., Macmillan Press, London, pp. 97-117 (1989)).

Any polynucleotide of the invention may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl- methyl-, thio- and other modified forms of adenine, cytidine, guanine, thymine, and uridine.

Antisense Nucleic Acids

In one aspect, the invention provides for use of antisense. Antisense generally refers particularly to the nucleic acid sequence of the non-coding strand of a double stranded DNA molecule encoding a polypeptide, or to a sequence which is substantially homologous to the non-coding strand. An antisense sequence is complementary to at least a portion of the sequence of a double stranded DNA molecule encoding a polypeptide. It is not necessary that the antisense sequence be complementary solely to the coding portion of the coding strand of the DNA molecule. The antisense sequence may be complementary to regulatory sequences specified on the coding strand of a DNA molecule encoding a polypeptide, which regulatory sequences control expression of the coding sequences.

Gene Therapy

For a review of gene therapy procedures, see Anderson, Science (1992)256:808-813; Nabel and Feigner (1993) TIBTECH 11: 211-217; Mitani and Caskey (1993) TIBTECH 11: 162-166; Mulligan (1993) Science 926-932; Dillon (1993) TIBTECH 11: 167-175; Miller (1992) Nature 357: 455-460; Van Brunt (1988) Biotechnology 6(10): 1149-1154; Vigne (1995) Restorative Neurology and Neuroscience 8: 35-36; Kremer and Perricaudet (1995) British Medical Bulletin 51(1) 3144; Haddada et al., (1995) in CURRENT TOPICS IN MICROBIOLOGY AND IMMUNOLOGY Doerfler and Boehm (eds.) Springer-Verlag, Heidelberg Germany; and Yu et al., GENE THERAPY (1994) 1:13-26.

Delivery of the gene or genetic material into the cell is the first critical step in gene therapy treatment of disease. A large number of delivery methods are well known to those of skill in the art. Such methods include, for example liposome-based gene delivery (Debs and Zhu (1993) WO 93/24640; Mannino and Gould-Fogerite (1988) BioTechniques 6(7): 682-691; Rose U.S. Pat. No. 5,279,833; Brigham (1991) WO 91/06309; and Felgner et al. (1987) Proc. Natl. Acad. Sci. USA 84: 7413-7414), and replication-defective retroviral vectors harboring a therapeutic polynucleotide sequence as part of the retroviral genome (see, e.g., Miller et al. (1990) Mol. Cell. Biol. 10:4239 (1990); Kolberg (1992) J. NIH Res. 4:43, and Cornetta et al. Hum. Gene Ther. 2:215 (1991)). Widely used retroviral vectors include those based upon murine leukemia virus (MuLV), gibbon ape leukemia virus (GaLV), Simian Immuno deficiency virus (SIV), human immuno deficiency virus (HIV), and combinations thereof. See, e.g., Buchscher et al. (1992) J. Virol. 66(5) 2731-2739; Johann et al. (1992) J. Virol. 66 (5):1635-1640 (1992); Sommerfelt et al., (1990) Virol. 176:58-59; Wilson et al. (1989) J. Virol. 63:2374-2378; Miller et al., J. Virol. 65:2220-2224 (1991); Wong-Staal et al., PCT/US94/05700, and Rosenburg and Fauci (1993) in Fundamental Immunology, Third Edition Paul (ed.) Raven Press, Ltd., New York and the references therein, and Y et al., GENE THERAPY (1994), supra).

AAV-based vectors are also used to transduce cells with target nucleic acids, e.g., in the in vitro production of nucleic acids and peptides, and in in vivo and ex vivo gene therapy procedures. See, West et al. (1987) Virology 160:3847; Carter et al. (1989) U.S. Pat. No. 4,797,368; Carter et al. WO 93/24641 (1993); Kotin (1994) Human Gene Therapy 5:793-801; Muzyczka (1994) J. Clin. Invest. 94:1351 and Samulski (supra) for an overview of AAV vectors. Construction of recombinant AAV vectors are described in a number of publications, including Lebkowski, U.S. Pat. No. 5,173,414; Tratschin et al. (1985) Mol. Cell. Biol. 5(11):3251-3260; Tratschin, et al. (1984) Mol. Cell. Biol., 4:2072-2081; Hermonat and Muzyczka (1984) Proc. Natl. Acad. Sci. USA, 81:6466-6470; McLaughlin et al. (1988) and Samulski et al. (1989) J. Virol., 63:03822-3828. Cell lines that can be transformed by rAAV include those described in Lebkowski et al. (1988) Mol. Cell. Biol., 8:3988-3996.

Gene therapy methodologies can be described by delivery site. Fundamental ways to deliver genes include ex vivo gene transfer, in vivo gene transfer, and in vitro gene transfer. In ex vivo gene transfer, cells are taken from the patient and grown in cell culture. The DNA is transfected into the cells, and the transfected cells are expanded in number and then reimplanted in the patient. For in vitro gene transfer, the method is the same, but the transfected cells are cells growing in culture, such as tissue culture cells, and not cells from the individual patient. In vivo gene transfer involves introducing the DNA into the cells of the patient when the cells are within the patient. Methods include using virally mediated gene transfer using a noninfectious virus to deliver the gene in the patient or injecting naked DNA into a site in the patient and the DNA is taken up by a percentage of cells in which the gene product protein is expressed.

Additionally, the other methods described herein, such as use mechanical or chemical methods may be used for in vivo insertion of the nucleic acids of the invention.

Mechanical methods of DNA delivery include direct injection of DNA, such as microinjection of DNA into germ or somatic cells, pneumatically delivered DNA-coated particles, such as the gold particles used in a "gene gun," and inorganic chemical approaches such as calcium phosphate transfection. Another method, ligand-mediated gene therapy, involves complexing the DNA with specific ligands to form ligand-DNA conjugates, to direct the DNA to a specific cell or tissue.

Chemical methods of gene therapy may involve a chemical to bind to the cell and/or ferry the DNA across the cell membrane, such as fusogenic lipid vesicles such as liposomes or other vesicles for membrane fusion, lipid particles of DNA incorporating cationic lipid such as lipofectin, or polylysine mediated transfer of DNA. Lipofectins or cytofectins, lipid-based positive ions that bind to negatively charged DNA, make a complex that can cross the cell membrane and provide the DNA into the interior of the cell. Another chemical method uses receptor-based endocytosis, which involves binding a specific ligand to a cell surface receptor and enveloping and transporting it across the cell membrane. The ligand binds to the DNA and the whole complex is transported into the cell. The ligand gene complex is injected into the blood stream and then target cells that have the receptor will specifically bind the ligand and transport the ligand-DNA complex into the cell.

Many gene therapy methodologies employ viral vectors to insert genes into cells and can be engineered to comprise the alternative splicing vector of; the present invention. For example, altered retrovirus vectors have been used in ex vivo methods to introduce genes into peripheral and tumor-infiltrating lymphocytes, hepatocytes, epidermal cells, myocytes, or other somatic cells. These altered cells are then introduced into the patient to provide the gene product from the inserted DNA.

Viral vectors have also been used to insert genes into cells using in vivo protocols (see e.g., Eck, S. L. and J. M. Wilson, "Gene Based Therapy", Goodman & Gilmer's The Pharmacological Basis of Therapeutics, 8th ea., pp. 77-101, McGraw-Hill, New York (1996)). To direct tissue-specific expression of foreign genes, cis-acting regulatory elements or promoters that are known to be tissue specific can be used. Alternatively, this can be achieved using in situ delivery of DNA or viral vectors to specific anatomical sites in vivo. For example, gene transfer to blood vessels in vivo was achieved by implanting in vitro transduced endothelial cells in chosen sites on arterial walls. The virus infected surrounding cells which also expressed the gene product. A viral vector can be delivered directly to the in vivo site, by a catheter for example, thus allowing only certain areas to be infected by the virus, and providing long-term, site-specific gene expression. In vivo gene transfer using retrovirus vectors has also been demonstrated in mammary tissue and hepatic tissue by injection of the altered virus into blood vessels leading to the organs.

Viral vectors that have been used for gene therapy protocols include, but are not limited to, retroviruses, other RNA viruses such as poliovirus or Sindbis virus, adenovirus, adeno-associated virus, herpes viruses, SV 40, vaccinia and other DNA viruses. Replication-defective murine retroviral vectors and adenoviral vectors are the most widely utilized gene transfer vectors. Murine leukemia retroviruses are composed of a single strand RNA complexed with a nuclear core protein and polymerase (pot) enzymes, encased by a protein core (gag) and surrounded by a glycoprotein envelope (env) that determines host range. The genomic structure of retroviruses include the gag, pot, and env genes enclosed at by the 5' and 3' long terminal repeats (LT11).

Retroviral vector systems exploit the fact that a minimal vector containing the 5' and 3' LTRs and the packaging signal are sufficient to allow vector packaging, infection and integration into target cells providing that the viral structural proteins are supplied in the packaging cell line. Fundamental advantages of retroviral vectors for gene transfer include efficient infection and gene expression in most cell types, precise single copy vector integration into target cell chromosomal DNA, and ease of manipulation of the retroviral genome.

The adenovirus is composed of linear, double stranded DNA complexed with core proteins and surrounded with capsid proteins. Advances in molecular virology have led to the ability to exploit the biology of these organisms to create vectors capable of transducing novel genetic sequences into target cells in vivo. Adenoviral-based vectors will express gene product peptides at high levels. Adenoviral vectors have high efficiencies of infectivity, even with low titers of virus. Additionally, the virus is fully infective as a cell free virion so injection of producer cell lines are not necessary. Another potential advantage to adenoviral vectors is the ability to achieve long-term expression of heterologous genes in vivo in some cell types.

Adenoviral vectors are derived from replication incompetent adenoviruses, which are typically contain a deletion in the E1 gene. Such vectors are transfected into cells, such as the 293 human embryonic kidney I cell line, which allow replication of E1 deleted adenoviruses. After transfection, the adenoviral vector is allowed to replicate in these specialized helper cells and form infectious particles, which are collected and purified.

Plasmids for transfection of mammalian cells for in vivo gene therapy include, for example, pRSVCAT, construction of this plasmid is described in Gorman et al., (1982) Proc. Nat. Acad. Sciences (USA) 79:6777-6781; p5'PRL3-CAT, construction of this plasmid is described in Sakai et al., (1988) Genes and Development 2:1144-1154; pSIS-CAT: construction of this plasmid is described in Huang and Gorman, Nucleic Acids Research, (1990) 18:937-948; pSVL; pMSG (Pharmacia, Uppsala, Sweden); pSV2dhfr (ATCC 37146); pBC12MI (ATCC 67109); pCMVSport 2.0; and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

In one aspect, a therapeutic of the present invention can be used to treat bone marrow cells ex vivo. Such treatment is routinely contemplated in the treatment of a variety of disease states, including in individuals who require bone marrow transplants (e.g., patients with aplastic anemia, acute leukemias, recurrent lymphomas, or solid tumors).

Ex vivo cell transfection for diagnostics, research, or for gene therapy (e.g., via re-infusion of the transfected cells into the host organism) is well known to those of skill in the art. For example, the cells are isolated from the subject organism, transfected with a gene or cDNA, and re-infused back into the subject organism (e.g., patient). Various cell types suitable for ex vivo transfection are well known to those of skill in the art (see, e.g., Freshney et al., Culture of Animal Cells, a Manual of Basic Technique, third edition Wiley-Liss, New York (1994)) and the references cited therein for a discussion of how to isolate and culture cells from patients). In humans, bone marrow aspirations from iliac crests are performed e.g., under general anesthesia in the operating room. Following transfection of the bone marrow cells ex vivo, they are injected intravenously back into the patient.

Expression Vectors

The present invention provides vectors which include polynucleotides of the present invention, host cells which are genetically engineered with vectors of the present invention and the production of polypeptides of the present invention by recombinant techniques. Such methods comprise culturing the host cells under conditions suitable for the expression of a CXCL9 polynucleotide and recovering the polypeptide produced therefrom from the cell culture.

In one aspect, the present invention provides host cells containing a recombinant construct as described below. The host cell can be a higher eukaryotic cell, such as a mammalian cell, or a lower eukaryotic cell, such as a yeast cell, or a prokaryotic cell, such as a bacterial cell. Representative examples of appropriate hosts include bacterial cells, such as *E. coli, Bacillus subtilis, Salmonella typhimurium*; and various species within the genera *Pseudomonas, Streptomyces*, and *Staphylococcus*, although others may also be employed as a routine matter of choice; fungal cells, such as yeast; insect cells such as *Drosophila* and Sf9; animal cells such as CHO, COS or Bowes melanoma; plant cells, etc. The selection of an appropriate host is deemed to be within the scope of those skilled in the art from the teachings provided herein.

Host cells are genetically engineered (transduced or transformed or transfected) with the vectors of this invention which may be a cloning vector or an expression vector. The engineered host cells can be cultured in conventional nutrient media modified as appropriate for activating promoters, selecting transformants or amplifying a CXCL9 gene. The culture conditions, such as temperature, pH and the like, are those previously used with the host cell selected for expression, and will be apparent to the ordinarily skilled artisan.

The present invention also includes recombinant constructs comprising one or more of the sequences as broadly described above. The constructs comprise a vector, such as a plasmid or viral vector, into which a sequence of the invention has been inserted, in a forward or reverse orientation. Such vectors include chromosomal, non-chromosomal and synthetic DNA sequences, e.g., derivatives of SV40; bacterial plasmids; phage DNA; yeast plasmids; vectors derived from combinations of plasmids and phage DNA, and viral DNA such as vaccinia, adenovirus, fowl pox virus, and pseudorabies. In a preferred aspect, a construct comprises an expression vector (as described below). Large numbers of suitable plasmids and vectors are known to those of skill in the art, and are commercially available. The following vectors are provided by way of example: (a) Bacterial: pBR322 (ATCC 37017); pGEM1 (Promega Biotec, Madison, Wis.), pUC, pSPORTI and pProExl (Life Technologies, Gaithersburg, Md.); pQE70, pQE60, pQE-9 (Qiagen); pBs, phagescript, psiX174, pBluescript SK, pBsKS, pNH8a, pNH16a, pNH18a, pNH46a (Stratagene); pTrc99A, pKK223-3, pKK233-3, pDR540, pRIT5, and pGEX4T (Pharmacia Fine Chemicals, Uppsala, Sweden); and (b) Eukaryotic: pWLneo, pSV2cat, pOG44, pXT1, pSG (Stratagene); pSVK3, pBPV, pMSG, pSVL (Pharmacia); pcDNA3.1 (Invitrogen). Other appropriate cloning and expression vectors. for use with prokaryotic and eukaryotic hosts are described by Sambrook et al., supra.

Generally however, any plasmid or vector may be used as long as it is replicable and viable in a host. For example, plasmids and vectors can include pIRESbleo3, pCMV-SPORT6, pUMCV3, pORF, pORF9, pcDNA3.1/GS, pCEP4, pIRESpuro3, pIRESpuro4, pcDNA3.1/Hygro(+), pcDNA3.1/Hygro(−), pEF6/V5-His, XLGold, ultracompetent cell (Stratagene), XL-Blue, DH5c, DH1OB, pIRESbleo3, pCMV-SPORT6, pUMCV3, pORF, pORF9, pcDNA3.1/GS, pCEP4, pIRESpuro3, pIRESpuro4, pcDNA3.1/Hygro(+), pcDNA3.1/Hygro(−), pEF6/V5-.

In one aspect, the construct is an expression vector which also comprises regulatory sequences operably linked to the sequence of interest, to direct mRNA synthesis and polypeptide production. Regulatory sequences known to operate in prokaryotic and/or eukaryotic cells include inducible and non-inducible promoters for regulating mRNA transcription, ribosome binding sites for translation initiation, stop codons for translation termination and transcription terminators and/or polyadenylation signals. In addition, an expression vector may include appropriate sequences for amplifying expression (such as a dihydrofolate reductase gene).

Promoter regions may be selected from any desired gene but preferably from one which is highly expressed. Particular named bacterial promoters include lacZ, gpt, lambda P sub R, P sub L and trp. Eukaryotic promoters include cytomegalovirus (CMV) immediate early, herpes simplex virus (HSV) thymidine kinase, early and late SV40, LTRs from retroviruses, mouse metallothionein-1, prion protein and neuronal specific enolase (NSE). Selection of the appropriate promoter is well within the level of ordinary skill in the art. In addition, a recombinant expression vector will include an origin of replication and selectable marker (such as a gene conferring resistance to an antibiotic (e.g., neomycin, chloramphenicol or ampicillin) or a reporter gene (e.g., luciferase)) which permit selection of stably transformed or transfected host cells.

In a preferred prokaryotic or yeast expression vector, a heterologous structural sequence (i.e., a polynucleotide of the present invention) is assembled in appropriate phase with translation initiation and termination sequences, and preferably, a leader sequence capable of directing secretion of translated protein into the periplasmic space or extracellular medium.

Optionally, the heterologous sequence will encode a fusion protein including an N-terminal identification peptide imparting desired characteristics, e.g., stabilization or simplified purification of expressed recombinant product.

Preferred eukaryotic expression vectors will also comprise an origin of replication, a suitable promoter operably linked to a sequence of interest and also any necessary translation enhancing sequence, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Such vectors may also include an enhancer sequence to increase transcription of a gene.

Enhancers are cis-acting elements of DNA, usually about from 10 to 300 bp, that act on a promoter to increase its transcription rate. Examples include the SV40 enhancer on the late side of the replication origin (bp 100 to 270), a cytomegalovirus early promoter enhancer, a polyoma enhancer on the late side of the replication origin, and adenovirus enhancers.

The appropriate DNA sequence may be inserted into a vector by a variety of procedures. Generally, site-specific DNA cleavage is performed by treating the DNA with suitable restriction enzymes under conditions which are generally specified by the manufacturer of these commercially available enzymes. Usually, about 1 microgram (Ig) of plasmid or DNA sequence is cleaved by 1 unit of enzyme in about 20 microliters (tL) of buffer solution by incubation at 37° C.

for 1 to 2 hours. After incubation with the restriction enzyme, protein is removed by phenol/chloroform extraction and the DNA recovered by precipitation with ethanol. The cleaved fragments may be separated using polyacrylamide or agarose gel electrophoresis, according to methods known by the routine practitioner. (See Sambrook et al., supra).

Ligations are performed using standard buffer and temperature conditions and with a ligase (such as T4 DNA ligase) and ATP. Sticky end ligations require less ATP and less ligase than blunt end ligations. When vector fragments are used as part of a ligation mixture, the vector fragment often is treated with bacterial alkaline phosphatase (BAP) or calf intestinal alkaline phosphatase (CIAP) to remove the 5'-phosphate and thus prevent religation of the vector. Alternatively, restriction enzyme digestion of unwanted fragments can be used to prevent ligation. Ligation mixtures are transformed into suitable cloning hosts such as E. coli and successful transformants selected by methods including antibiotic resistance, and then screened for the correct construct.

Transformation or transfection of an appropriate host with a construct of the invention, such that the host produces recombinant polypeptides, may also be performed in a variety of ways. For example, a construct may be introduced into a host cell by calcium chloride transformation, lithium chloride or calcium phosphate transfection, DEAE-Dextran mediated transfection, or electroporation. These and other methods for transforming/transfecting host cells are well known to routine practitioners (see L. Davis et al., "Basic Methods in Molecular Biology", 2nd edition, Appleton and Lang, Paramount Publishing, East Norwalk, Conn. (1994)).

Recovery of Expressed Proteins from Recombinant Host Cells Following transformation or transfection of a suitable host strain and growth of the host strain to an appropriate cell density, the selected promoter is derepressed by appropriate means (e.g., temperature shift or chemical induction), and cells are cultured for an additional period.

Cells are typically harvested by centrifugation, disrupted by physical or chemical means (to release intracellular protein) and the resulting crude extract retained for further purification. Microbial cells employed in expression of proteins can be disrupted by any convenient method, including freeze-thaw cycling, sonication, mechanical disruption, or use of cell lysing agents; such methods are well-known to the ordinary artisan. When the expressed protein has been secreted, it can be purified directly from the supernatant of harvested cells.

CXCL9 polypeptide is recovered and purified from the supernatant or crude extract by known methods including ammonium sulfate or ethanol precipitation, acid extraction, affinity chromatography, anion or cation exchange chromatography, phosphocellulose chromatography, hydrophobic interaction chromatography, hydroxyapatite chromatography or lectin chromatography. It is preferred to have low concentrations (approximately 0.1-5 mM) of calcium ion present during purification (Price, et al., J. Biol. Chem. 244:917 (1969)). Protein refolding steps can be used, as necessary, in completing configuration of the protein. Finally, high performance liquid chromatography (HPLC) can be employed for final purification steps.

An alternative method for the production of large amounts of secreted protein involves the transformation of mammalian embryos and the recovery of the recombinant protein from milk produced by transgenic cows, goats, sheep, etc. Polypeptides and closely related molecules may be expressed recombinantly in such a way as to facilitate protein purification. One approach involves expression of a chimeric protein which includes one or more additional polypeptide domains not naturally present on human polypeptides. Such purification-facilitating domains include, but are not limited to, metal-chelating peptides such as histidine-tryptophan domains that allow purification on immobilized metals, protein A domains that allow purification on immobilized immunoglobulin, and the domain utilized in the FLAGS extension/affinity purification system (Immunex Corp, Seattle, Wash.). The inclusion of a cleavable linker sequence such as Factor XA or enterokinase from Invitrogen (San Diego, Calif.) between the polypeptide sequence and the purification domain may be useful for recovering the polypeptide.

Gene Therapy Administration

One skilled in the art recognizes that different methods of delivery may be utilized to administer a vector into a cell. Examples include: (1) methods utilizing physical means, such as electroporation (electricity), a gene gun (physical force) or applying large volumes of a liquid (pressure); and (2) methods wherein said vector is complexed to another entity, such as a liposome, aggregated protein or transporter molecule.

Furthermore, the actual dose and schedule can vary depending on whether the compositions are administered in combination with other pharmaceutical compositions, or depending on interindividual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

These methods described herein are by no means all-inclusive, and further methods to suit the specific application will be apparent to the ordinary skilled artisan. Moreover, the effective amount of the compositions can be further approximated through analogy to compounds known to exert the desired effect.

Chemotherapeutic Agents

Chemotherapeutic agents include alkylating agents, antimetabolites, natural products such as plant alkaloids and biologics. Alkylating agents bind covalently to DNA to inhibit DNA synthesis and stop cell growth. Suitable alkylating agents include, but are not limited to, nitrogen mustards such as chlorambucil, cyclphosphamide, estramustine, ifosfamide, mechlorethamine and melphalan, aziridine derivatives such as thiotepa, alkyl sulfonates such as busulfan and nitrosoureas, such as carmustine.

Antimetabolites are agents that block the biosynthesis or use of normal cellular metabolites. Similar to alkylating agents, antimetabolites inhibit DNA synthesis. However, antimetabolites are more effective against slower growing tumors than alkylating agents. Suitable antimetabolites include, but are not limited to, folate analogs such as methotrexate, purine analogs such as fludarabine, mercaptopurine and thioguanine, adenosine analogs such as cladribine and pentostatin and pyrimidine analogs such as capecitabine, cytarabine, depocyt, floxuridine and fluorouracil.

The third class of chemotherapeutic agents are natural products such as antitumor antibiotics. Suitable antitumor antibiotics include, but are not limited to, bleomycin, dactinomycin, daunorubicin, doxorubicin, doxil, epirubicin, idarubicin, ritomycin and mitoxantrone.

Other natural products include the vinca alkaloids which arrest cell division by preventing the formation of the mitotic spindle through disaggregation of microtubules. Suitable vinca alkaloids include, but are not limited to, vincristine, vinblastine, vinorelbine and vindesine. Taxanes are another type of natural product chemotherapeutic agent. Taxanes include, but are not limited to paclitaxel and docetaxel. The taxanes stabilize microtubules to inhibit mitotic spindle assembly to prevent cell division.

Biologics are yet another class of chemotherapeutic agents, and encompass monoclonal antibodies, soluble receptors, protein-chemotherapeutic conjugates, antisense oligonucleotides, and the like. Example of such agents include, Avastin® (bevacizumab), Campath® (alemtuzumab), Erbitux® (cetuximab), Herceptin® (trastuzumab), Rituxan (rituximab), Zevalin™ (ibritumomab tiuxetan), BEXXAR® (Tositumomab and I-131 tositumomab; monoclonal antibody targeting the CD20 antigen and radiolabeled version of the antibody), Mylotarg™ (gemtuzumab ozogamicin).

The chemotherapeutic agents described above can be either cell cycle dependent or cell cycle independent. An agent is cell cycle dependent it its effectiveness depends on which stage of the cell cycle the target (cancer) and non-target (normal) cells are in when the agent is administered. For example, alkylating agents are generally cell cycle dependent, because they are selectively toxic for cells during the S-phase. Cell cycle independent chemotherapeutic agents have approximately equal toxicity at all stages of the cell cycle. An antibody to a tumor antigen, especially if labeled with a toxin or a radioisotope, is likely to be cell cycle independent.

Radiation Therapy

Radiation therapy (radiotherapy) can be used to treat almost every type of solid tumor, including brain, breast, cervix, larynx, lung, pancreas, prostate, skin, spine, stomach, uterus cancers, or soft tissue sarcomas. The appropriate dosage of radiation depends on a number of factors, including the type of cancer, type of radiation treatment, as well as proximity of radiation therapy to tissues and organs nearby that may be damaged by radiation, and tolerances of those tissues and organs to radiation. For example, radiation doses range from a low of 65 Gy to a high of 81 Gy for the treatment of prostate cancer, while for the treatment of solid epithelial tumors, the dosage can range between 50 Gy and 70 Gy. In contrast, lymphomas typically receive lower doses, ranging between 20 to 40 Gy in daily doses.

Radiation therapies which are suitable for use in the combination treatments described herein, include the use of a) external beam radiation; and b) a radiopharmaceutical agent which comprises a radiation-emitting radioisotope.

External beam radiation therapy for the treatment of cancer uses a radiation source that is external to the patient, typically either a radioisotope, such as $^{60}$Co, $^{137}$CS or a high energy x-ray source, such as a linear accelerator. The external source produces a collimated beam directed into the patient to the tumor site. External-source radiation therapy avoids some of the problems of internal-source radiation therapy, but it undesirably and necessarily irradiates a significant volume of non-tumorous or healthy tissue in the path of the radiation beam along with the tumorous tissue.

The adverse effect of irradiating of healthy tissue can be reduced, while maintaining a given dose of radiation in the tumorous tissue, by projecting the external radiation beam into the patient at a variety of "gantry" angles with the beams converging on the tumor site. The particular volume elements of healthy tissue, along the path of the radiation beam, change, reducing the total dose to each such element of healthy tissue during the entire treatment.

The irradiation of healthy tissue also can be reduced by tightly collimating the radiation beam to the general cross section of the tumor taken perpendicular to the axis of the radiation beam. Numerous systems exist for producing such a circumferential collimation, some of which use multiple sliding shutters which, piecewise, can generate a radio-opaque mask of arbitrary outline.

A new method of external radiotherapy, called conformal radiotherapy or three-dimensional conformal radiotherapy, can also be used to treat tumors that, in the past, were considered too close to a vital organ or tissue to permit effective radiotherapy. The complex process of conformal radiotherapy begins with the creation of a three-dimensional reconstruction of a patient's tumors and normal adjacent anatomy. The 3-D computer images thus developed are used to deliver highly focused, or "conformed" radiotherapy to the tumor while sparing normal adjacent tissue, resulting in overall higher dosage of radiation than previously permitted, while causing less harm to proximal tissues and organs.

A "radiopharmaceutical agent", as defined herein, refers to a pharmaceutical agent which contains at least one radiation-emitting radioisotope. Radiopharmaceutical agents are routinely used in nuclear medicine for the diagnosis and/or therapy of various diseases. The radiolabeled pharmaceutical agent, for example, a radiolabeled antibody, contains a radioisotope (RI) which serves as the radiation source. As contemplated herein, the term "radioisotope" includes metallic and non-metallic radioisotopes. The radioisotope is chosen based on the medical application of the radiolabeled pharmaceutical agents. When the radioisotope is a metallic radioisotope, a chelator is typically employed to bind the metallic radioisotope to the rest of the molecule. When the radioisotope is a non-metallic radioisotope, the non-metallic radioisotope is typically linked directly, or via a linker, to the rest of the molecule.

As used herein, a "metallic radioisotope" is any suitable metallic radioisotope useful in a therapeutic or diagnostic procedure in vivo or in vitro. Suitable metallic radioisotopes include, but are not limited to: Actinium-225, Antimony-124, Antimony-125, Arsenic-74, Barium-103, Barium-140, Beryllium-7, Bismuth-206, Bismuth-207, Bismuth212, Bismuth213, Cadmium-109, Cadmium-15m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-60, Copper-62, Copper-64, Copper-67, Erbium-169, Europium-152, Gallium-64, Gallium-67, Gallium-68, Gadolinium153, Gadolinium-157 Gold-195, Gold-199, Hafnium-175, Hafnium-175-181, Holmium-166, Indium-110, Indium-111, Iridium-192, Iron 55, Iron-59, Krypton85, Lead-203, Lead-210, Lutetium-177, Manganese-54, Mercury-197, Mercury203, Molybdenum-99, Neodymium-147, Neptunium-237, Nickel-63, Niobium95, Osmium-185+191, Palladium-103, Palladium-109, Platinum-195m, Praseodymium-143, Promethium-147, Promethium-149, Protactinium-233, Radium-226, Rhenium-186, Rhenium-188, Rubidium-86, Ruthenium-97, Ruthenium-103, Ruthenium-105, Ruthenium-106, Samarium-153, Scandium-44, Scandium-46, Scandium-47, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, Zirconium-89, and Zirconium-95.

As used herein, a "non-metallic radioisotope" is any suitable nonmetallic radioisotope (non-metallic radioisotope) useful in a therapeutic or diagnostic procedure in vivo or in vitro. Suitable non-metallic radioisotopes include, but are not limited to: Iodine-131, Iodine-125, Iodine-123, Phosphorus-32, Astatine-211, Fluorine-18, Carbon-11, Oxygen-15, Bromine-76, and Nitrogen-13.

Identifying the most appropriate isotope for radiotherapy requires weighing a variety of factors. These include tumor uptake and retention, blood clearance, rate of radiation delivery, half-life and specific activity of the radioisotope, and the feasibility of large-scale production of the radioisotope in an economical fashion. The key point for a therapeutic radiopharmaceutical is to deliver the requisite amount of radiation dose to the tumor cells and to achieve a cytotoxic or tumoricidal effect while not causing unmanageable side-effects.

It is preferred that the physical half-life of the therapeutic radioisotope be similar to the biological half-life of the radiopharmaceutical at the tumor site. For example, if the half-life of the radioisotope is too short, much of the decay will have occurred before the radiopharmaceutical has reached maximum target/background ratio. On the other hand, too long a half-life would cause unnecessary radiation dose to normal tissues. Ideally, the radioisotope should have a long enough half-life to attain a minimum dose rate and to irradiate all the cells during the most radiation sensitive phases of the cell cycle. In addition, the half-life of a radioisotope has to be long enough to allow adequate time for manufacturing, release, and transportation.

Other practical considerations in selecting a radioisotope for a given application in tumor therapy are availability and quality. The purity has to be sufficient and reproducible, as trace amounts of impurities can affect the radiolabeling and radiochemical purity of the radiopharmaceutical.

The target receptor sites in tumors are typically limited in number. As such it is preferred that the radioisotope have high specific activity. The specific activity depends primarily on the production method. Trace metal contaminants must be minimized as they often compete with the radioisotope for the chelator and their metal complexes compete for receptor binding with the radiolabeled chelated agent.

The type of radiation that is suitable for use in the methods of the present invention can vary. For example, radiation can be electromagnetic or particulate in nature. Electromagnetic radiation useful in the practice of this invention includes, but is not limited to, x-rays and gamma rays. Particulate radiation useful in the practice of this invention includes, but is not limited to, electron beams (beta particles), protons beams, neutron beams, alpha particles, and negative pi mesons. The radiation can be delivered using conventional radiological treatment apparatus and methods, and by intraoperative and stereotactic methods. Additional discussion regarding radiation treatments suitable for use in the practice of this invention can be found throughout Steven A. Leibel et al., Textbook of Radiation Oncology (1998) (publ. W. B. Saunders Company), and particularly in Chapters 13 and 14. Radiation can also be delivered by other methods such as targeted delivery, for example by radioactive "seeds," or by systemic delivery of targeted radioactive conjugates. J. Padawer et al., Combined Treatment with Radioestradiol Iucanthone in Mouse C3HBA Mammary Adenocarcinoma and with Estradiol Iucanthone in an Estrogen Bioassay, Int. J. Radiat. Oncol. Biol. Phys. 7:347-357 (1981). Other radiation delivery methods can be used in the practice of this invention.

For tumor therapy, both α and β-particle emitters have been investigated. Alpha particles are particularly good cytotoxic agents because they dissipate a large amount of energy within one or two cell diameters. The β-particle emitters have relatively long penetration range (2-12 mm in the tissue) depending on the energy level. The long-range penetration is particularly important for solid tumors that have heterogeneous blood flow and/or receptor expression. The β-particle emitters yield a more homogeneous dose distribution even when they are heterogeneously distributed within the target tissue.

Co-Therapy with Additional Myeolosuppressive Agents

The compositions and methods of the invention can be combined with administration of one or more additional myelosuppressive agents to further prevent damage to bone marrow, or to increase peripheral white blood cells following subsequent chemotherapy or radiotherapy, or to treat cancer or a bone marrow disorder. One such myeolosuppressive agent is CCL3, also known as macrophage inflammatory protein-1α. It is understood that in addition to a natural form of CCL3, variants such as fragments, mutants, or chemically modified versions of CCL3 can be used as well, provided that they have a myelosuppressive effect. Agents such as CCL3 block the entry of hematopoietic stem cells into the S-phase of the cell cycle. See, e.g., Clemons et al., Blood 92:1532 (1998). In some embodiments, an effective dose of CCL3 or another myelosuppressive agent is administered prior to chemotherapy or radiotherapy in addition to the administration of, e.g., CXCL9 or a CXCR3 agonist. In other embodiments, an effective dose of CCL3 or another myeolosuppressive agent is administered prior to chemotherapy or radiotherapy, and following chemotherapy or radiotherapy a CXCR3 antagonist antagonist of the invention is administered, such as a CXCL9 antibody, a CXCL9 siRNA, a CXCL9 antisense nucleic acid, a CXCR3 antibody, a CXCR3 siRNA, a CXCR3 antisense nucleic acid, or a small molecule CXCR3 antagonist.

Co-Therapy with Hematopoietic Growth Factors

The compositions and methods of the invention can also be administered together with the administration of a hematopoietic growth factor, such as GM-CSF or G-CSF following chemotherapy or radiotherapy. The hematopoietic growth factor can be a naturally occurring molecule or a fragment, mutant, or chemical modification thereof, provided that the growth factor is effective in either stimulating the proliferation of one or more types of bone marrow stem cell or progenitor cell or promoting the differentiation and development of a stem cell or progenitor cell leading to myelogenesis or hematopoiesis. In some embodiments, prior to chemotherapy or radiotherapy and the administration of a hematopoietic growth factor, CXCL9 or a CXCR3 agonist is administered. In other embodiments, the administration of a hematopoietic growth factor is accompanied by administration of a CXCR3 antagonist (including a CXCL9 antibody, a CXCL9 siRNA, a CXCL9 antisense nucleic acid, a CXCR3 antibody, a CXCR3 siRNA, a CXCR3 antisense nucleic acid, or a small molecule CXCR3 antagonist) following chemotherapy or radiotherapy.

Treating a Disease

Agents of the present invention, such as the anti-CXCL9 antibodies and siRNAs of the invention may find use in a variety of ways. In a preferred aspect, a method comprises the step of administering to a subject, preferably to a subject in need of such treatment, an amount of an agent that inhibits CXCL9 signaling effective to treat the disease. Preferably, the subject is a human. Agents for use in this method, such as anti-CXCL9 antibodies or siRNAs are disclosed herein.

In a preferred aspect the disease is a cancer. Agents of the present invention are useful for treating a cancer selected from the group consisting of breast, ovarian, colorectal, gastric, lung, kidney, bladder, prostate, uterine, thyroid, pancreatic, cervical, esophageal, mesothelioma, head and neck, hepatocellular, melanoma, brain, vulval, testicular, sarcoma, intestine, skin, leukemia, and lymphoma cancer. A preferred cancer is breast cancer, melanoma, lung cancer, mesothelioma, thyroid cancer, colon cancer or liver cancer.

As used herein, the terms "treat", "treating", and "treatment" include: (1) preventing a disease, such as cancer, i.e., causing the clinical symptoms of the disease not to develop in a subject that may be predisposed to the disease but does not yet experience any symptoms of the disease; (2) inhibiting the disease, i.e., arresting or reducing the development of the disease or its clinical symptoms; or (3) relieving the disease, i.e., causing regression of the disease or its clinical symptoms. Preferably, the subject in need of such treatment is a mammal, more preferable a human.

The compositions containing inhibitors and agents of the invention (e.g., antibodies) can be administered for therapeutic or prophylactic treatments. In therapeutic applications, compositions are administered to a patient suffering from a disease (e.g., breast cancer) in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the agents of this invention to effectively treat the patient. An amount of an inhibitor that is capable of preventing or slowing the development of cancer in a patient is referred to as a "prophylactically effective dose." The particular dose required for a prophylactic treatment will depend upon the medical condition and history of the patient, the particular cancer being prevented, as well as other factors such as age, weight, gender, administration route, efficiency, etc. Such prophylactic treatments may be used, e.g., in a patient who has previously had cancer to prevent a recurrence of the cancer, or in a patient who is suspected of having a significant likelihood of developing cancer.

As used herein, a "therapeutically effective amount" is the amount of a therapeutic composition sufficient to provide a beneficial effect to a mammal to which the composition is administered. These methods described herein are by no means all-inclusive, and further methods to suit the specific application will be apparent to the ordinary skilled artisan. Moreover, the effective amount of the compositions can be further approximated through analogy to compounds known to exert the desired effect.

Experimental Animal Models

The methods and compositions of the invention have beneficial effects on myelogenesis. Various models exist, both in vivo (in animals and humans) and in vitro, that allow certain aspects of the process of myelogenesis to be investigated. Such models can be used to study the effectiveness of the compositions and methods of the invention, and, for example, to select a dosage or administration protocol. For example, the level or proliferative activity of bone marrow stem cells or bone marrow progenitor cells can be determined either in bone marrow or in circulating blood. Progenitor cells such as CFU-GM, CFU-GEMM, BFU-E, or CFU-S can be isolated from mice or humans, their numbers counted, and the cells cultured to ascertain the effectiveness of a composition or method of the invention in stimulating bone marrow regeneration of the progenitor cell donor. Alternatively, a competitive regeneration assay can be performed, in which the repopulating ability of a test marrow specimen is evaluated in lethally irradiated mice. In vitro colony assays, such as the CFU-GM, BFU-E, CFU-GEMM, and CFu-Blast assays, also can be employed to measure the number of healthy stem cells in a sample from a treated animal or human. Further examples of such assays can be found in Mauch et al., Int. J. Radiation 31:1319-1339 (1995).

One aspect of the invention is a method for treating cancer. One such method includes administering to a cancer patient a CXCL9 agonist or a CXCR3 agonist prior to administering chemotherapy or radiation therapy. Another such method includes administering a CXCL9 antagonist or a CXCR3 antagonist after administering chemotherapy or radiation therapy. A number of animal models of cancer are known which can be used to select an appropriate dose or administration protocol for carrying out a method or using a composition of the invention.

Colon adenocarcinoma in rodents induced by the procarcinogen 1,2-dimethylhydrazine and its metabolite azoxymethane (AOM) is a well-characterized carcinogen-induced tumor because of its morphological similarity to human colon cancer, high reproducibility and relatively short latency period (Shamsuddin, (1986) Human Path. 17:451-453). This rodent tumor model is similar to human colon adenocarcinoma not only in its morphology (Shamsuddin & Trump, (1981) J. Natl. Cancer Inst. 66:389-401) but also in the genes that are involved in tumorigenesis (Shivapurkar et al., (1995) Cancer Lett. 96:63-70; Takahashi et al., (2000) Carcinogenesis 21:1117-1120).

In addition to chemical carcinogen-induced models of colon cancer in rodents, gene disruption of the catalytic subunits of phosphoinositide-3-OH kinase (PI3-Kγ) (Sasaki et al., (2000) Nature 406:897-902) or the guanosine-binding protein Gαi2 (Rudolph et al., (1995) Nat. Genet. 10: 143-50) causes spontaneous colon cancer in rodents. These studies indicate that potential causes other than alterations in the prototypical tumor suppressor genes and oncogenes could be involved in the etiology of human colon cancer.

A number of animal models for oral squamous cell carcinoma have been developed, including rat, mouse and hamster models. A hamster cheek pouch tumor model induced by the carcinogen 7,12-dimethylbenzanthracene remains one of the most common models (Baker (1986) Malignant neoplasms of the oral cavity. In: Otolaryngology-Head and Neck Surgery, Cummings et al. (eds.) pp. 1281-1343. St. Louis, Mo.: CV Mosby), but exhibits a number of differences from human oral cavity tumorigenesis. A recent mouse model using the carcinogen 4-nitroquinoline 1-oxide (4-NQO) has been developed which more closely simulates many aspects of human oral cavity and esophageal carcinogenesis (Tang et al. (2004) Clin. Cancer Res. 10: 301-313).

An animal model for multiple myeloma has been described (Garrett et al. (1997) Bone 20: 515-520), which uses a murine myeloma cell line 5TGM1 that causes lesions characteristic of human myeloma when injected into mice. Such lesions include severe osteolysis and the involvement of non-bone organs including liver and kidney. Mice inoculated with cultured 5TGM1 cells predictably and reproducibly develop disease, symptoms of which include the formation of a monoclonal gammopathy and radiologic bone lesions.

A number of animal models for the study of glioma exist, including an intracerebral rat glioma model (Sandstrom et al. (2004) Br. J. Cancer, 91: 1174-1180), and a murine model using injection of dog-derived J3T1 glioma cells (U.S. Pat. No. 6,677,155).

Animal models for the study of non-small cell lung cancer have been previously described, for example, by xenografting human tumors by subcutaneous transplantation of LC-6 human non-small cell lung cancer into BALB/C-nu/nu mice (Tashiro et al. (1989) Cancer Chemother. Pharmacol. 24, 187).

An animal model for the study of stomach cancer has been described which uses AZ521 human stomach cancer xenografts in nude mice (Fukushima et. al. (2000) Biochem. Pharmacol. 59, 1227-1236).

Numerous animal models of AML have been previously described, including in rats (Blatt, J et al. (1991) Leuk. Res. 15:391-394), and SCID mice (Vey, N. et al. (2000) Clin. Cancer Res., 6:731-736).

A number of animal models used for the study of HCC have been described (Chisari et al., (1985) Science 230: 1157-1160; Babinet et al. (1985) Science 230: 1160-11; U.S. Publication No. 2004/0016011). These references disclose the generation of transgenic mouse models of HCC by incorporating the HBV virus into the genome.

Animal models with experimental metastasis pattern resembling those frequently observed in human patients (Engebraaten & Fodstad, (1999) Int. J. Cancer. 82:219-25), which use MA-11 and MT-1, two estrogen and progesterone receptor-negative human breast cancer cell lines. Other models for breast cancer include U.S. Publication No. 2003/0215861 (herein incorporated by reference). Alternatively, the ability of the compounds of the present invention to function as anti-breast cancer agents, either alone or in combination with other agents, can be demonstrated in vivo in carcinogen induced mammary tumors in wild type Sprague-Dawley Rats (Thompson H. J et al, Carcinogenesis, (1992) 13:1535-1539).

A number of animal models for ovarian cancer are known in the art. For example, Connolly et al. ((2003) Cancer Research, 63, 1389-1397), discloses methods of developing epithelial ovarian cancer in mice by chimeric expression of the SV40 Tag under control of the MISIIR promoter. In another example, Liu et al. (Cancer Research 64, 1655-1663 (2004)) have introduced human HRAS or KRAS oncogenes into immortalized human ovarian surface epithelial cells, which form subcutaneous tumors after injection into immunocompromised mice.

Numerous animal models for the study of prostate cancer are available. One murine model, using prostate cancer xenografts introduced into SCID mice, is disclosed in U.S. Pat. No. 6,756,036. Alternatively, an orthotopic mouse model of metastatic prostate cancer can be used, as disclosed in U.S. Publication No. 2004/0009508.

Dosing and Administration

Subject, as used herein, refers to animals such as mammals, including, but not limited to, primates (e.g., humans), cows, sheep, goats, horses, pigs, dogs, cats, rabbits, guinea pigs, rats, mice or other bovine, ovine, equine, canine, feline, rodent or murine species. In a preferred aspect, the mammal is a human.

As used herein, treating and treatment refer to partially or totally inhibiting formation of, or otherwise treating (e.g., reversing or inhibiting the further development of) cancer such as tumors, neoplasms, carcinomas, sarcomas, leukemias, lymphomas and the like.

As used herein, therapeutically effective amount refers to an amount sufficient to elicit the desired biological response. In the present invention, the desired biological response is partially or totally inhibiting formation of, or otherwise treating (e.g., reversing or inhibiting the further development of) cancer such as tumors, neoplasms, carcinomas, sarcomas, leukemias, lymphomas and the like.

A therapeutically effective amount can be achieved in the method or pharmaceutical composition of the invention employing a first amount of a CXCL9 and a second amount of a suitable chemotherapy or radiotherapy agent. In one aspect, the CXCL9 and the suitable chemotherapy or radiotherapy agent are each administered in a therapeutically effective amount (i.e., each in an amount which would be therapeutically effective if administered alone). In another aspect, the CXCL9 and the suitable chemotherapy or radiotherapy agent are each administered in an amount which alone does not provide a therapeutic effect (a sub-therapeutic dose). In yet another aspect, the CXCL9 can be administered in a therapeutically effective amount, while the suitable chemotherapy or radiotherapy agent is administered in a sub-therapeutic dose. In still another aspect, the CXCL9 can be administered in a sub-therapeutic dose, while the suitable chemotherapy or radiotherapy agent is administered in a therapeutically effective amount. It is understood that the method of coadministration of a first amount of a CXCL9 and a second amount of a suitable chemotherapy or radiotherapy agent can result in an enhanced or synergistic therapeutic effect, wherein the combined effect is greater than the additive effect that would result from separate administration of the first amount of the CXCL9 and the second amount of the suitable chemotherapy or radiotherapy agent. A synergistic effect can be, for example, an increase of 3-fold, 10-fold, 100-fold or greater therapeutic effect than the sum of the therapeutic effects expected from administering each agent separately. The greater therapeutic effect can be manifested in a variety of ways, for example, greater reduction in tumor size, more rapid reduction in tumor size, reduced morbidity or mortality, or longer time until recurrence of the tumor.

The presence of a synergistic effect can be determined using suitable methods for assessing drug interaction. Suitable methods include, for example, the Sigmoid-Emax equation (Holford, N. H. G. and Scheiner, L. B., Clin. Pharmacokinet. 6: 429-453 (1981)), the equation of Loewe additivity (Loewe, S, and Muischnek, H., Arch. Exp. Pathol. Pharmacol. 114: 313-326 (1926)) and the median-effect equation (Chou, T. C. and Talalay, P., Adv. Enzyme Regul. 22: 27-55 (1984)). Each equation referred to above can be applied with experimental data to generate a corresponding graph to aid in assessing the effects of the drug combination. The corresponding graphs associated with the equations referred to above are the concentration-effect curve, isobologram curve and combination index curve, respectively.

Pharmaceutically acceptable carrier, includes pharmaceutical diluents, excipients or carriers suitably selected with respect to the intended form of administration, and consistent with conventional pharmaceutical practices. For example, solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof.

Pharmaceutically acceptable carriers can be aqueous or non-aqueous solvents. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media.

The compounds for use in the method of the invention can be formulated for administration by any suitable route, such as for oral or parenteral, for example, transdermal, transmucosal (e.g., sublingual, lingual, (trans)buccal), vaginal (e.g., trans- and perivaginally), (intra)nasal and (trans)rectal), subcutaneous, intramuscular, intradermal, intra-arterial, intravenous, inhalation, and topical administration.

Suitable compositions and dosage forms include tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays, dry powders or aerosolized formulations.

It is preferred that the compounds are orally administered. Suitable oral dosage forms include, for example, tablets, capsules or caplets prepared by conventional means with pharmaceutically acceptable excipients such as binding agents (e.g., polyvinylpyrrolidone or hydroxypropylmethylcellulose); fillers (e.g., lactose, microcrystalline cellulose or calcium phosphate); lubricants (e.g., magnesium stearate, talc or silica); disintegrates (e.g., sodium starch glycollate); or wetting agents (e.g., sodium lauryl sulphate). If desired, the tablets can be coated, e.g., to provide for ease of swallowing or to provide a delayed release of active, using suitable methods. Liquid preparation for oral administration can be in the form of solutions, syrups or suspensions. Liquid preparations (e.g., solutions, suspensions and syrups) are also suitable for oral administration and can be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

As used herein, the term "pharmaceutically acceptable salt" refers to a salt of a compound to be administered prepared from pharmaceutically acceptable non-toxic acids including inorganic acids, organic acids, solvates, hydrates, or clathrates thereof. Examples of such inorganic acids are hydrochloric, hydrobromic, hydroiodic, nitric, sulfuric, and phosphoric. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like.

It is understood that CXCL9 compounds can be identified, for example, by screening libraries or collections of molecules using suitable methods. Another source for the compounds of interest are combinatorial libraries which can comprise many structurally distinct molecular species. Combinatorial libraries can be used to identify lead compounds or to optimize a previously identified lead. Such libraries can be manufactured by well-known methods of combinatorial chemistry and screened by suitable methods.

As used herein, continuous dosing refers to the chronic administration of a selected active agent.

As used herein, as-needed dosing, also known as "pro re nata" "prn" dosing, and "on demand" dosing or administration is meant the administration of a therapeutically effective dose of the compound(s) at some time prior to commencement of an activity wherein suppression of a lower urinary tract disorder would be desirable.

Administration can be immediately prior to such an activity, including about 0 minutes, about 10 minutes, about 20 minutes, about 30 minutes, about 1 hour, about 2 hours, about 3 hours, about 4 hours, about 5 hours, about 6 hours, about 7 hours, about 8 hours, about 9 hours, or about 10 hours prior to such an activity, depending on the formulation.

In a particular aspect, drug administration or dosing is on an as-needed basis, and does not involve chronic drug administration. With an immediate release dosage form, as-needed administration can involve drug administration immediately prior to commencement of an activity wherein suppression of the symptoms of overactive bladder would be desirable, but will generally be in the range of from about 0 minutes to about 10 hours prior to such an activity, preferably in the range of from about 0 minutes to about 5 hours prior to such an activity, most preferably in the range of from about 0 minutes to about 3 hours prior to such an activity.

Suitable dosing ranges for CXCL9 can be, for example, from about 100 micrograms to about 2 g per day, for example, from about 200 micrograms to about 1 g per day, such as from about 300 micrograms to about 750 mg per day, or for example, from about 400 micrograms to about 600 mg per day.

The compounds for use in the method of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

In practicing the methods of the invention, coadministration refers to administration of a first amount of the CXCL9 and a second amount of a suitable chemotherapy or radiotherapy agent, wherein the first and second amounts together comprise a therapeutically effective amount to treat cancer in a subject in need of treatment. Coadministration encompasses administration of the first and second amounts of the compounds of the coadministration in an essentially simultaneous manner, such as in a single pharmaceutical composition, for example, capsule or tablet having a fixed ratio of first and second amounts, or in multiple, separate capsules or tablets for each. In addition, such coadministration also encompasses use of each compound in a sequential manner in either order. When coadministration involves the separate administration of the first amount of the CXCL9 and the second amount of the suitable chemotherapy or radiotherapy agent the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, the CXCL9 and the suitable chemotherapy or radiotherapy agent can be administered in any order within about 24 hours of each other, within about 16 hours of each other, within about 8 hours of each other, within about 4 hours of each other, within about 1 hour of each other or within about 30 minutes of each other.

The therapeutically effective amount of a first amount of the CXCL9 and a second amount of a suitable chemotherapy or radiotherapy agent in combination will depend on the age, sex and weight of the patient, the current medical condition of the patient and the nature of the cancer being treated. The skilled artisan will be able to determine appropriate dosages depending on these and other factors. The ratio of CXCL9 to any single chemotherapy or radiotherapy agent can be, for example, in the range of about 1:1000, 1:100, 1:50, 1:10, 1:1, 10:1, 50:1, 100:1, or 1000:1 on a weight basis.

Formulation

One or more suitable unit dosage forms having a therapeutic agent of the invention, which, as discussed below, may optionally be formulated for sustained release (for example using microencapsulation, International Publication No. WO 94/07529, and U.S. Pat. No. 4,962,091), can be administered by a variety of routes including parenteral, including by intravenous and intramuscular routes, as well as by direct injection into the diseased tissue. For example, the therapeutic agent may be directly injected into the tumor. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampoules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

The expression vectors, transduced cells, polynucleotides and polypeptides (active ingredients) of this invention can be formulated and administered to treat a variety of disease states by any means that produces contact of the active ingredient with the agent's site of action in the body of the organism. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium Ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

The active ingredients of the invention may be formulated to be suspended in a pharmaceutically acceptable composition suitable for use in mammals and in particular, in humans. Such formulations include the use of adjuvants such as muramyl dipeptide derivatives (MDP) or analogs that are described in U.S. Pat. Nos. 4,082,735; 4,082,736; 4,101,536; 4,185,089; 4,235,771; and 4,406,890. Other adjuvants, which are useful, include alum (Pierce Chemical Co.), lipid A, trehalose dimycolate and dimethyldioctadecylammonium bromide (DDA), Freund's adjuvant, and IL-12. Other components may include a polyoxypropylene-polyoxyethylene block polymer (Pluronic®), a non-ionic surfactant, and a metabolizable oil such as squalene (U.S. Pat. No. 4,606,918).

Additionally, standard pharmaceutical methods can be employed to control the duration of action. These are well known in the art and include control release preparations and can include appropriate macromolecules, for example polymers, polyesters, polyamino acids, polyvinyl, pyrrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Accordingly, the pharmaceutical composition of the present invention may be delivered via various routes and to various sites in an mammal body to achieve a particular effect (see, e.g., Rosenfeld et al., 1991; Rosenfeld et al., 1991a; Jaffe et al., supra; Berkner, supra). One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The active ingredients of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and mammal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

These methods described herein are by no means all-inclusive, and further methods to suit the specific application will be apparent to the ordinary skilled artisan. Moreover, the effective amount of the compositions can be further approximated through analogy to compounds known to exert the desired effect.

Kits for Use in Diagnostic, Research, and Therapeutic Applications

The invention also provides kits that can be used for the detection of the CXCL9 nucleic acids or proteins disclosed here. Further, kits are provide comprising compositions described herein that allow the user to practice the methods of the invention. In diagnostic and research applications such kits may include any or all of the following: assay reagents, buffers, CXCL9-specific antibodies, hybridization probes and/or primers, and the like. A therapeutic product may include sterile saline or another pharmaceutically acceptable emulsion and suspension base.

In a preferred aspect, the kit comprises an agent embracing the specifics as outlined herein, wherein the agent binds CXCL9 protein or CXCL9 nucleic acid, such as mRNA, interferes with CXCL9 signaling, or inhibits binding of CXCL9 protein to other proteins. The kit may further comprise one or more containers for agents and compositions of the present invention and instructions for using the agent to treat a disease, such as a cancer or to practice any of the methods described herein.

In a preferred aspect of the invention, a kit comprises a siRNA, wherein the siRNA binds to CXCL9 mRNA and inhibits translation of CXCL9 mRNA. Optionally, the kit comprises a control siRNA.

As indicated above, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

In one aspect, an antibody of the invention is administered to a patient in an amount or dosage suitable for treatment. Generally, dosing can vary depending on patient considerations. Such considerations include, for example, age, condition, sex, extent of disease, contraindications, concomitant therapies and the like. An exemplary unit dosage based on these considerations can also be adjusted or modified by a physician skilled in the art. Administration of an antibody of the invention to a subject may be local or systemic and accomplished intravenously, intraarterially, intrathecally (via the spinal fluid) or the like. Administration may also be intradermal or intracavitary, depending upon the body site under examination.

The examples herein are provided to illustrate advantages of the present invention that have not been previously described and to further assist a person of ordinary skill in the art with preparing or using the compounds of the invention or salts, pharmaceutical compositions, derivatives, prodrugs, racemic mixtures or tautomeric forms thereof. The examples can include or incorporate any of the variations or aspects of the invention described above. The aspects described above may also further each include or incorporate the variations of any or all other aspects of the invention.

EXAMPLES

Example 1

Construction of Eukaryotic Mouse CXCL9 Expression Plasmid

The backbone vector pcDNA3.1 (−) and its host strain *E. coli* DH5α were provided by Prof. Liu of Shanghai University. RT-PCR kits and KOD plus were purchased from Toyoba (Japan). Restriction enzymes and T4 DNA ligase were purchased from Fermentas (USA). The endofree plasmid preparation kit was purchased from BioDev (Beijing, China).

The mouse CXCL9 cDNA was retro-transcribed from total RNA isolated from C57BL/6B mice bone marrow cells. The coding sequence of the gene is from base 58 to base 438 (GB: NM_008599) without the signal peptide coding sequence. PCR primers were designed according to the coding sequence and synthesized by Sangon (China). The forward primer contained an engineered XhoI site (underlined) and KOZAC sequence 'CCACC': 5'-CCG CTCGAG CCACC ATGAAGTCCGCTGTTCTTTCC-3' (SEQ ID NO:1), and the reverse primer contained an engineered EcoRI site (underlined): 5'-CG GAATTC T TGTAGTCTTCCTTGAAC-GAC-3, (SEQ. ID. NO.2). To fit the His-tag frame into the vector, an extra T was added between the coding sequence and the EcoRI site in the reverse primer. It uses the stop codon in the vector.

After denaturation of DNA for 2 min at 94° C., PCR was performed as follows: 35 cycles of melting at 94° C. for 20 sec, annealing at 56° C. for 30 sec, and extension at 68° C. for 45 sec. The purified PCR product and vector were digested with XhoI and EcoRI, gel-purified, and ligated together. Then the recombinant plasmid was transformed into *E. coli* DH5α component cells, which were cultured at 37° C. on LB agar with Ampicillin (100 μg/ml) for selection. The recombinant plasmid was further analyzed by restriction enzyme cleavage pattern and finally confirmed by DNA sequencing (Invitrogen, China). The sequence-verified plasmid was multiplied in *E. coli* DH5α and purified for use.

Example 2

In Vivo Electroporation of DNA Encoding CXCL9

Intramuscular injection of plasmid DNA followed by electroporation (DNA+EP) was performed according to a commonly used protocol. Briefly, the mice were anesthetized by intraperitoneal injection of chloral hydrate at a dose of 10 μl/g of body weight. After complete sedation, each mouse received 25 μg DNA in 50 μl of pH 7.4 PBS in the right tibialis anterior (TA) muscles using a microsyringe. Immediately after the injection, electroporation with eight electric pulses was applied by a BTX800 electroporation device (Harvard Apparatus, USA) through a pair of silver electrodes spaced 5 mm apart and covering the intramuscular injection site. The electric pulses were 20 ms in duration and 1 s apart, and had a total voltage of 100 V (200 V/cm).

Female 6- to 8-week old C57BL/6 mice and SD rats (100-150 g body weight) were purchased from SLAC Laboratory Animal Co. (Shanghai, China). All animal experiment protocols used in this study were designed and performed abiding by the regulations of SJTU and the Chinese government.

Example 3

Production of Anti-rMuCXCL9 Polyclonal Antibodies

Anti-MuCXCL9 polyclonal antibodies were raised in Wistar rats (SLAC) using purified rMuCXCL9. Briefly, 300 μg of rMuCXCL9 was mixed with equal volume of Freund's complete adjuvant and injected subcutaneously into the rats. From the 21st day after the first injection, rats were boosted by injection of the proteins mixed with equal volume of Freund's incomplete adjuvant every week for 3 weeks. Antibodies were collected from the animals two weeks after the last booster.

Example 4

Peripheral Blood Cell and Bone Marrow Cell Counting

Blood was collected from the jugular vein of anesthetized mice and peripheral blood cells were counted using a MEK6300 cell counter (Japan) according to the user's manual. Then the mice were sacrificed and the right femur and tibia of each mouse were washed with pH 7.4 PBS for bone marrow cell harvesting. After centrifugation at 1500 rpm for 10 min, the cell pellet was resuspended in 1 ml PBS, and the cells were counted using the MEK 6300 counter (Japan).

Example 5

CXCL9 Expression in 5-FU Treated Mice

Figure 1B:
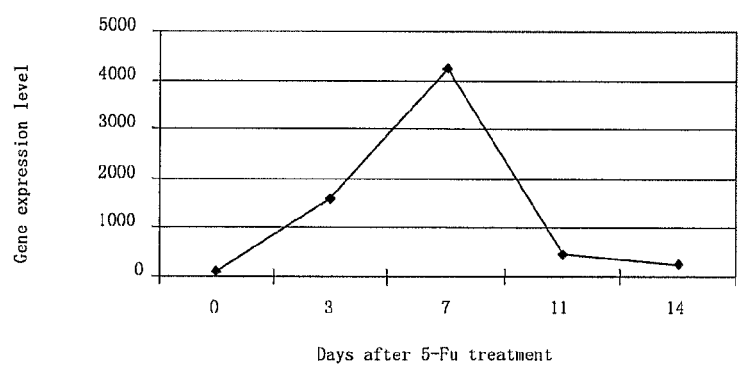
FIG. 1B shows the expression level of CXCL9 gene in mice after 5-FU treatment.

Mice of 7-8 weeks age were injected with 5-fluorouracil (5-FU) at a dose of 250 mg/kg via the tail vein. The sera of mice were analyzed at days 0, 3, 7, 11, 14 post injection using a mouse CXCL9 ELISA kit. The ELISA kit for mouse CXCL9 was purchased from R&D. The levels of CXCL9 found in the sera are shown in FIG. 1 (A). CXCL9 expression was greatly up-regulated at day 7 post 5-FU treatment, achieving a level about 10-fold higher than normal ($P^*<0.001$ according to one-way ANOVA). However, the expression of CXCL9 dropped off rapidly after day 7. At day 11 post 5-FU treatment, there was already no difference in the CXCL9 level in sera between normal mice and 5-FU treated mice.

Analysis of CXCL9 gene expression using an Affymetrix Gene Chip showed a similar peak at day 7 (FIG. 1 (B)). Five total RNA samples were extracted from bone marrow cells collected at days 0, 3, 7, 11, 14 days post-5-FU treatment. Bone marrow cells from 5-20 mice were used for each time point to collect enough cells for RNA extraction. Equal amounts of poly(A) RNA from each sample were used to synthesize double-stranded cDNA. Five cRNA probes were prepared by in vitro transcription using equal amount of cDNAs of five samples. Equal amount of probes were used for hybridization to mouse genome expression oligonucleotide arrays (GeneChip mouse expression set 430, Affymetrix, Santa Clara, Calif.) containing 34,323 well substantiated mouse genes. The hybridization intensity information was gathered using a GeneChip scanner 3000 and analyzed with Affymetrix microarray suite version 5.1 (Affymetrix, Santa Clara, Calif.). The global scaling strategy was used for all arrays that set the average signal intensity of the array to a target signal of 500. Comparison analyses for expression data at each time point were calculated by using day 0-array as baseline.

Example 6

CXCL9 Expressed In Vivo Inhibits Proliferation of Hematopoietic Cells of Normal Mice A vector capable of expressing CXCL9 in eukaryotic cells was constructed using a pcDNA3.1 (−) plasmid. See Example 1 for the construction of the expression vector. The plasmid was administered to the tibial muscle of the right legs of mice, followed by electroporation. See Example 2 for details of the electroporation procedure. Peripheral white blood cells and bone marrow cells were counted at days 0, 5, 10, 17, and 27 post transfection as described in Example 4, and the results are presented in FIG. 2.

Figure 2A:
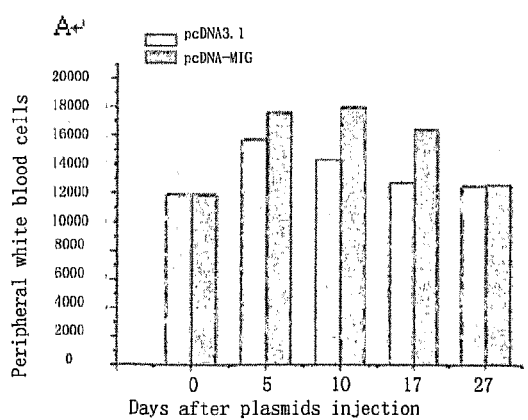
FIG. 2A shows peripheral white blood cell counts after transfection with pcDNA3.1 and pcDNA3.1-CXCL9.

There was no significant difference between the CXCL9 and control groups in peripheral white blood cell counts (FIG. 2(A)). The cells from 1 μl of peripheral blood were counted.

Figure 2B:
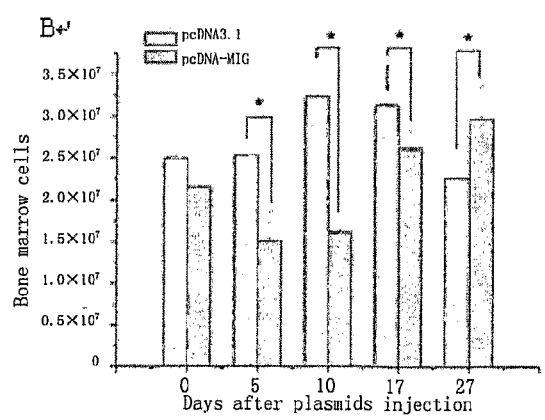
FIG. 2B shows bone marrow cell counts of mice after transfection with pcDNA3.1 and pcDNA3.1-CXCL9. At day 5, the CXCL9 group showed fewer cells than the control group and that pattern continued to day 17. Significance of difference between the two groups was calculated by one-way ANOVA and $p^*<0.01$.

Counts of total bone marrow cells were taken from one femur and one tibia (FIG. 2(B)). At day 5, the CXCL9 group showed fewer cells than the control group, and that pattern continued through day 17. At day 27, the two groups had recovered from the effect of the electroporation, and the CXCL9 group had more cells than the control. The statistical significance of differences between the two groups was calculated using one-way ANOVA and $p^*<0.01$.

Figure 2C:
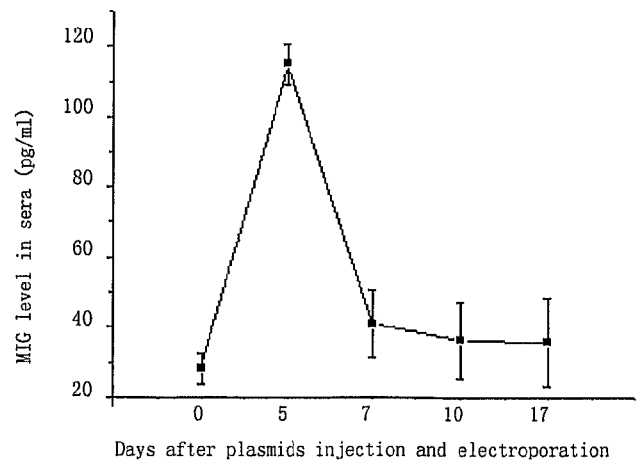
FIG. 2C shows the serum expression levels of CXCL9 after transfection with pcDNA3.1-CXCL9 as determined by ELISA.

The expression of CXCL9 cDNA from pcDNA3.1(−) is shown in FIG. 2C. At day 0, 25 μg/50 μl plasmid in pH 7.4 PBS was injected to the skeletal muscle immediately followed by electroporation. At days 5, 7, 10 and 17, mice were sacrificed and the CXCL9 level in serum tested by ELISA. The expression of CXCL9 increased to a peak at day 5, but it went down quickly at day 7.

Example 7

Enhancement of Bone Marrow Recovery from 5-FU Treatment Using a CXCL9 Expression Vector Mice (female, 8 weeks old) were transfected with CXCL9 expression vector as described in Example 2 at day 7 following 5-FU treatment at a dose of 200 mg/kg via injection into the tail vein. Peripheral blood cells and bone marrow cells were counted at days 0, 3, 7, 11 and 14 following 5-FU injection to evaluate bone marrow suppression and recovery.

Figure 3:
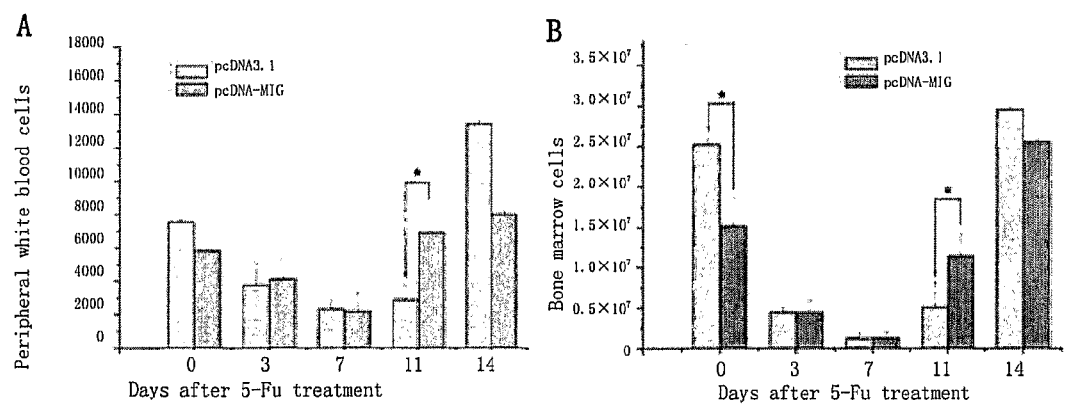
FIG. 3A shows peripheral white blood cell counts after treatment of mice with 5-FU. The mice were transfected with either pcDNA3.1 or pcDNA3.1-CXCL9 as indicated.
FIG. 3B shows bone marrow cell counts from the same groups of mice as shown in FIG. 3A.

FIG. 3 (A) shows the results of peripheral white blood cell counts. The data show the number of cells from 1 μl of peripheral blood. There was no significant difference between the two groups except at day 11. At day 11 the white blood cells of the CXCL9 group had recovered better than the pcDNA3.1 control group.

FIG. 3 (B) shows the results of bone marrow cell counts. The counts were total bone marrow cells from one femur and one tibia. At day 0, the CXCL9 group showed fewer cells than the control group, and that pattern is consistent with FIG. 2B. There was no significant difference between the two groups at days 3, 7, and 14. However, at day 11, bone marrow cells of the CXCL9 group had recovered significantly better than the control group. Significance of the differences was calculated by one-way ANOVA and p*<0.01.

In control mice, at day 7 after 5-FU treatment both peripheral blood cells and bone marrow cells were maximally suppressed. However, both peripheral blood cell and bone marrow counts recovered nearly to normal levels at day 14. At day 11, the CXCL9 group showed better recovery than the control group (FIG. 3). Apparently, in the CXCL9 group more progenitor hematopoietic cells survived 5-FU toxicity, thus allowing a more rapid recovery.

Example 8

Myelosuppressive Function of Recombinant CXCL9 in Normal Mice

Recombinant mouse CXCL9 (rMuCXCL9) was expressed in E. coli BL21 and purified. The purified rMuCXCL9 protein was tested by a chemotaxis assay and was found to be bioactive. rMuCXCL9 was administered to C57 female mice (7-8 weeks old) by injection into the tail vein. Three doses were evaluated: 3 ng, 30 ng and 300 ng to each mouse; the mice each weighed about 18 g. Equal volumes of PBS were injected into control mice. The rMuCXCL9 was administrated consecutively for 5 days, one time each day. The peripheral white blood cells and bone marrow cells were counted at days 0, 5, 10, 15 and 20.

Figure 4:
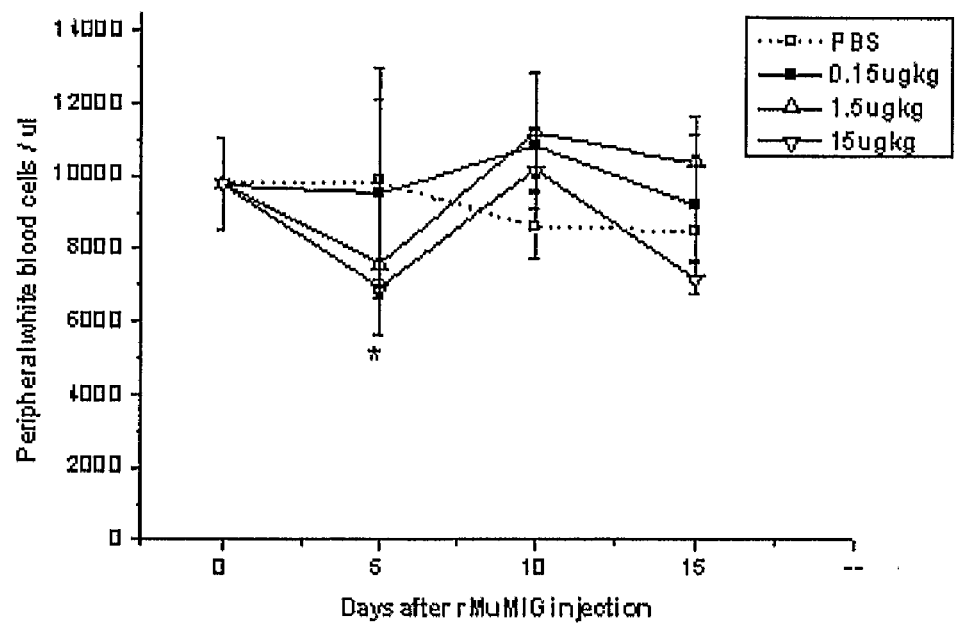
FIG. 4A shows peripheral white blood cell counts as a function of time after treatment of mice with the indicated amounts of rMuCXCL9 or with PBS as control.
FIG. 4B shows bone marrow cell counts from the same groups of mice as in FIG. 4A.
Figure 4:
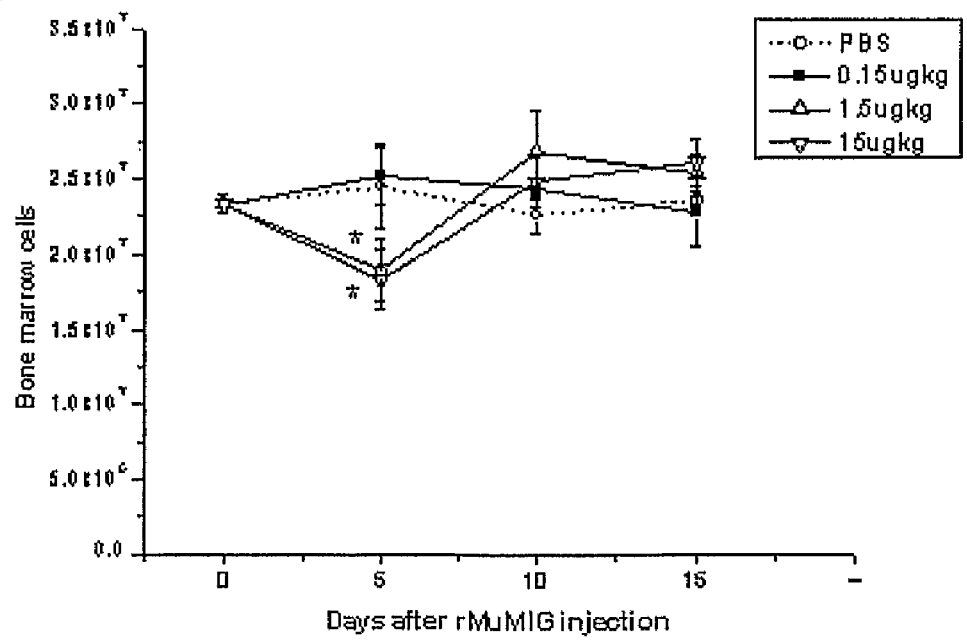

FIG. 4A shows the white blood cell counts from 1 μl of peripheral blood. There was no significant difference between the rMuCXCL9 groups and the control group at days 0 and 5. Differences appeared between the two higher-dose rMuCXCL9 groups and the control group, as indicated by *.

FIG. 4B shows the counts of total bone marrow cells from one femur and one tibia. At day 5, the rMuCXCL9 groups receiving the two higher doses showed decreased cell counts compared to the control group. Bone marrow counts recovered rapidly at day 10. The bone marrow cell counts suggest that rMuCXCL9 inhibited the proliferation of hematopoietic cells, resulting in the decrease. Significance of differences between the groups was calculated by one-way ANOVA and p*<0.01.

Example 9

Protection of Bone Marrow from High-Dose 5-FU by Recombinant CXCL9

The effect of rMuCXCL9 on survival of mice treated with high-dose 5-FU was investigated. The C57 mice used for the study were female and 7-8 weeks old. rMuCXCL9 was administered at 200 ng per mouse once daily for 5 consecutive days. Subsequently, the mice received 5-FU at 250 mg/kg injected via the tail vein (day 0). Thus rMuCXCL9 administration was at days −5 to −1. Control mice were administered PBS instead of rMuCXCL9, but received the 250 mg/kg dose of 5-FU. The changes in peripheral white blood cells and bone marrow cells were observed at days 0, 3, 7, 11, and 14 (FIGS. 5A and 5B). Because the dose of 250 mg/kg of 5-FU is normally lethal to mice of 7-8 weeks of age, the death of the mice was also recorded (FIG. 5C).

Figure 5:
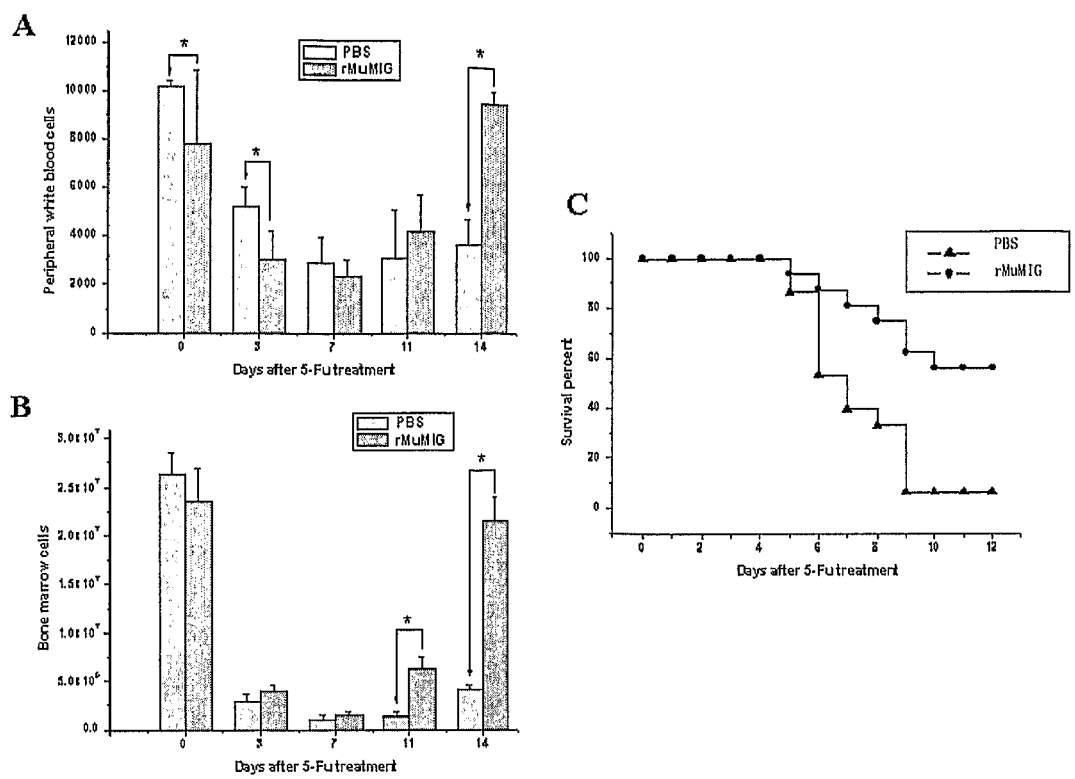
FIG. 5A shows peripheral white blood cell counts as a function of time after treatment of mice with 5-FU at day 0. The mice also received either rMuCXCL9 or PBS as indicated on days −5 to −1.
FIG. 5B shows bone marrow cell counts from the same groups of mice as in FIG. 5A.
FIG. 5C shows survival curves for the same rMuCXCL9 and control mice.

FIG. 5A shows the white blood cell counts from 1 μl of peripheral blood. The rMuCXCL9 group had lower cell counts than the control group, due to the 5-day rMuCXCL9 administration. While at day 14 the control group was still being suppressed, the rMuCXCL9 group had already recovered to the normal level.

FIG. 5B shows the bone marrow cell counts from one femur and one tibia. At days 11 and 14, the rMuCXCL9 group had recovered better than the control group, as indicated by *. Particularly at day 14, the rMuCXCL9 group had already recovered to near normal level. Significance of the differences between groups was calculated by one-way ANOVA and p*<0.01.

FIG. 5C shows the survival data on the two groups. Most mice of the control group didn't survive the toxicity of high-dose 5-FU, and the survival rate was only about 10% until day 12. However, the rMuCXCL9 group had a much higher survival rate of about 60%.

Example 10

Enhancement of Bone Marrow Recovery After High-Dose 5-FU Administration by Anti-CXCL9 Antibody An anti-CXCL9 polyclonal antibody was produced by immunizing rats with rMuCXCL9. Control rats were injected with PBS buffer containing no rMuCXCL9 to produce the control serum. Both sera were analyzed by western blot. Anti-CXCL9 serum was able to specifically bind the rMuCXCL9 protein, while the control serum had no effect.

The anti-CXCL9 and control sera were administered to 5-FU treated mice subcutaneously. The day of 5-FU treatment was considered as day 0, and the sera were administrated consecutively from day 0 to day 10, once per day. Immediately before injection, 1 μl of serum was obtained and diluted with normal saline to 10 μl. As described for the ELISA experiments above, CXCL9 levels are up-regulated after 5-FU treatment and would be as high as 10 times the normal level at day 7 post 5-FU treatment.

Figure 6:
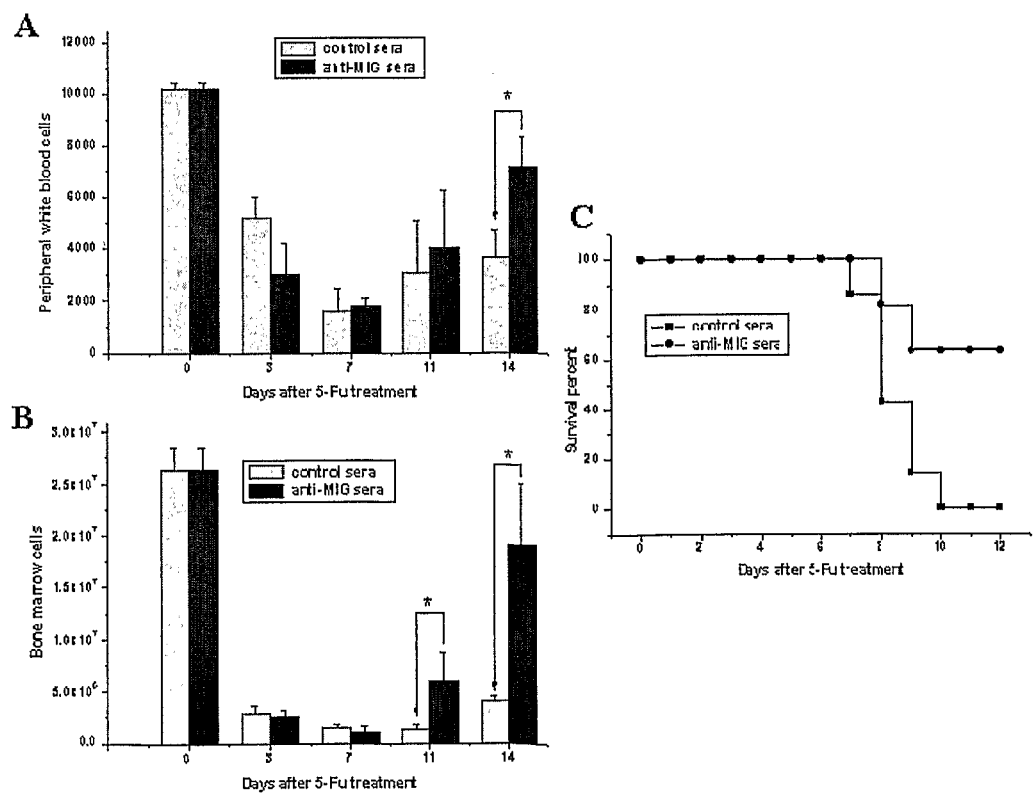
FIG. 6A shows peripheral white blood cell counts as a function of time after treatment of mice with 5-FU at day 0. The mice also received either a polyclonal rat antiserum to MuCXCL9 or a control serum as indicated on days 0 to 10.
FIG. 6B shows bone marrow cell counts from the same groups of mice as in FIG. 6A.
FIG. 6C shows survival curves for the same rMuCXCL9 antiserum and control serum mice.

FIG. 6A shows the white blood cell counts from 1 μl of peripheral blood. There was no significant difference between the control serum and anti-CXCL9 serum groups from day 0 to day 11. At day 11, the mice of the control serum group had died off, so the cell count data for days 11 and 14 for the control group were taken from FIG. 5A. The anti-CXCL9 serum group recovered better than the control group, as indicated by *.

FIG. 6B shows bone marrow cell counts from one femur and one tibia. For the same reason as for FIG. 6A, the control group data at days 11 and 14 were taken from the PBS control group of FIG. 5B. The anti-CXCL9 serum group recovered better than the control PBS group, as indicated by *. Particularly at day 14, the anti-CXCL9 serum group had already recovered to near the normal level. Significance of the differences between groups was calculated by one-way ANOVA and p*<0.01.

FIG. 6C shows the survival information for the two groups. The mice of the control serum group had died off by day 11, while the anti-CXCL9 group had a final survival percent of >60%.

Example 11

Expression and Purification of Recombinant Murine CXCL9

Highly purified (>99%) rMuCXCL9 was obtained from bacterial inclusion bodies using a simple one column purification strategy. The biological activity of the purified protein was demonstrated using a murine spleen cell chemotaxis assay.

Construction of the rMuCXCL9 Expression Vector

Figure 7:
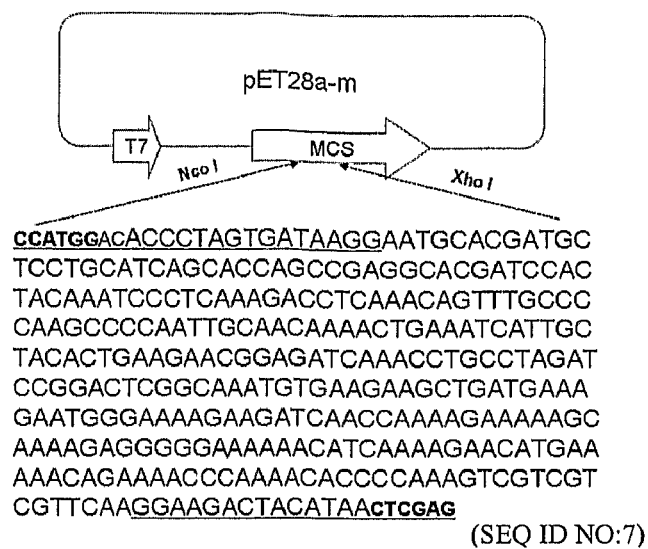
FIG. 7 shows a map of plasmid pET28a-m (SEQ ID NO:7). Underlined letters are primers and the forward primer contains a NcoI site and an extra 'AC' portion. The reverse primer contains a XhoI site and the natural stop codon 'TAA'.

The expression vector pET28a (+) and its host strain E. coli BL21 (DE3) were purchased from Novagen. RT-PCR kits and DNA polymerase (KOD plus) were purchased from Toyoba Company (Japan). The CXCL9 cDNA was reverse transcribed from total RNA isolated from C57BL/6b mouse bone marrow cells. The mature mouse CXCL9 cDNA covers the coding sequences of the gene from bp 121 to 438 of GB:NM_008599 without the signal peptide coding sequences. PCR primers were designed according to that sequences and synthesized by Sangon (China). The forward primer contained an engineered NcoI site (underlined) 5'-CATG CCATGG ACACCCTAGTGATAAGG-3' (SEQ ID NO:3), and the reverse primer was incorporated an engineered XhoI site (underlined) 5'-CCG CTCGAG TTATGTAGTCTTCCT-TGAACG-3' (SEQ ID NO:4). It used the natural stop codon of the gene (FIG. 7). To avoid the His-tag and T7-tag of the vector, the NcoI site was chosen to contain the ATG translation start codon (FIG. 7). To construct the coding sequence of mature MuCXCL9 in frame with the ATG, and to connect to the extra G in the NcoI site, an extra amino acid, Asp (D), was created by addition of AC to the 5' end of the MuCXCL9 coding sequence.

After denaturation for 2 min at 94° C., amplification was performed for 35 cycles consisting of 20 sec at 94° C., 30 sec at 56° C., and 40 sec at 68° C. The purified PCR product and vector were digested with NcoI and XhoI (Fermentas, U.S.), gel-purified, and ligated together. *E. coli* DH5α was chemically transformed with the recombinant vector and cultured at 37° C. in LB agar with kanamycin (100 μg/ml) for selection of recombinants. The recombinant plasmid containing an accurate copy of the MuCXCL9 gene was named pET28a-m (FIG. 7). It was further analyzed by restriction enzyme digestion pattern and finally confirmed by DNA sequencing (Invitrogen, China).

Expression of rMuCXCL9

*E. coli* BL21 (DE3) cells were transformed with the plasmid pET28a-m. A single transformed BL21 colony was inoculated into 3 ml LB medium supplemented with kanamycin (100 μg/ml) grown with 250 rpm shaking overnight at 37° C. 100 μl culture was transferred to 3 ml fresh LB medium in a 10 ml tube. The culture was grown with 250 rpm shaking at 37° C. until the OD600 reached 1.0 and then 3 μl of 500 mM IPTG was added for induction. 1 ml sample was collected at 3 h after induction. The pellet was resuspended in 50 μl of ddH$_2$O, mixed with 2×SDS loading buffer (0.09 M Tris-HCl, pH 6.8; 0.1 M DTT; 2% SDS; 20% glycerol; 0.02% bromophenol blue), and heated at 100° C. for 5 min. The sample was centrifuged at 10,000 g for 5 min and 10 μl supernatant was analyzed by 12% SDS-PAGE and stained with Coomassie brilliant blue R-250 solution.

Figure 8:
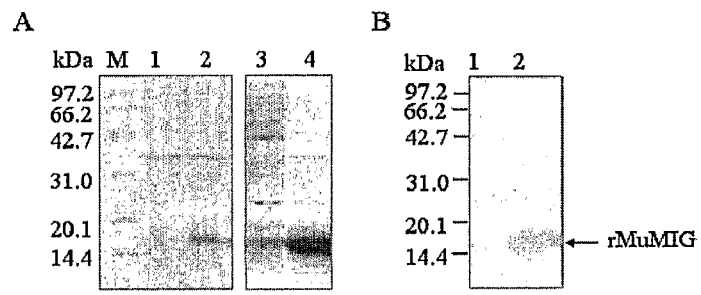
FIG. 8A shows SDS-PAGE profiles of fractions obtained from the expression of rMuCXCL9 in *E. coli* BL21. Lane M: molecular weight markers. Lane 1: uninduced *E. coli* lysate. Lane 2: *E. coli* lysate after IPTG induction. Lane 3: supernantant of *E. coli* lysate after sonication of induced *E. coli*.
FIG. 8B shows a Western blot of E. coli lysate with commercial anti-CXCL9 antibody. Lane 1: uninduced E. coli lysate. Lane 2: IPTG-induced E. coli lysate.

The expression of a 15 kDa protein was induced (FIG. 8A, Lane 2). The identity of the expressed protein was investigated by Western blot using commercial available anti-CXCL9 antibody. The uninduced and induced *E. coli* protein extracts (FIG. 8A, Lanes 1 and 2) were separated by SDS-PAGE and transferred onto a PVDF membrane. Western blot with anti-CXCL9 antibody was performed, one band on the membrane corresponding to the size of rMuCXCL9 was detected only present in the bacteria extract after IPTG induction (FIG. 8B, Lane 2), and not in the uninduced bacteria extract (FIG. 8B, Lane 1). The Western blot result indicated that the observed induced protein is rMuCXCL9.

The predicted molecular weight of the rMuCXCL9 was 12.4 kDa. The rMuCXCL9 showed a mobility of about 15 kDa when analyzed by SDS-PAGE (FIG. 8A).

After IPTG induction, the bacteria containing rMuCXCL9 were sonicated, and the soluble cell lysate (FIG. 8A, Lane 3) and inclusion bodies (FIG. 8A, Lane 4) were analyzed by SDS-PAGE and protein staining. The inclusion bodies were found to contain most of the rMuCXCL9, representing 40% of the total protein in the inclusion bodies measured by densitometry scanning of the stained gel.

Preparation of Inclusion Bodies 800 ml LB medium, supplemented with kanamycin (100 μg/ml), was inoculated with an overnight starter culture (OD600 of <0.1). Cultures were grown at 37° C. with 250 rpm shaking to OD600 of 0.8-1.0 and then induced with 1 mM IPTG (final concentration) for 3 h. Cells were harvested by centrifugation at 10,000 g for 15 min. Cell pellet was resuspended in the lysis buffer (1×PBS, 1 mM EDTA, 0.1 mM PMSF) at a final concentration of 50 mg/ml and sonicated (SANYO soniprep 150, 15 bar; 30 s working and 30 s resting on ice for a cycle, 18 cycles). After centrifugation at 12,000 g for 15 min at 4° C., the undissolved inclusion bodies were collected and washed with the pellet wash buffer (0.5% Triton X-100, 10 mM EDTA, 50 mM NaCl) at 12,000 g for 5 min at 4° C., 5 times. The inclusion bodies were then solubilized in Buffer U (20 mM Na$_2$HPO$_4$, 1 mM EDTA, 50 mM NaCl, pH 9.0) containing 8 M urea at 9 ml Urea/g pellet, shaking slightly at 37° C. for 1 h. The insoluble pellets were removed by centrifugation at 15,000 g for 20 min at 4° C., and the dissolved inclusion bodies were ready for further purification.

Refolding and Purification of rMuCXCL9

The refolding was carried out by drop-wise dilution into defined protein folding buffer. The protein solution was dropped by pumping into 10-fold volume refolding buffer (20 mM NaPO$_4$, 1 mM EDTA, pH 6.0), under vigorous (magnetic stirrer) agitation. pH of the solution was maintained at 6.0. Then an equal volume dilution buffer (20 mM NaPO$_4$, 1 mM EDTA, pH 8.5) was added into the folding buffer. The refolded protein solution was set at 4° C. for about 24 h.

The refolded protein solution was centrifuged at 18,000 g for 30 min. The collected supernatant was loaded onto an S-Sepharose column with a volume of approximately 20 ml. The column was pre-equilibrated with Buffer A (20 mM NaPO$_4$, 1 mM EDTA, pH 7.2). Sample was loaded at speed of 0.5 ml/min and the column was then washed with 2 column volumes of Buffer A. The column bound proteins were eluted using a programmed gradient of Buffer B (20 mM NaPO$_4$, 1 mM EDTA, 1 M NaCl, pH 7.2) at a speed of 3 ml/min.

SDS-PAGE and Western Blotting

SDS-PAGE was performed using a 12% resolution gel on the PowerPac Basic (Bio-Rad). Briefly, the protein samples were loaded on the gel, which was electrophoresed at 120 V for 1 h and then stained with Coomassie brilliant blue R-250.

For the Western blotting experiments, the proteins were transferred to PVDF membranes on a tank-blotting device (Bio-Rad) at 200 mA for 90 min. Horseradish peroxidase-conjugated polyclonal anti-MuCXCL9 antibody (R&D, USA) was diluted at 1:500 in PBS containing 0.05% Tween 20 (TBS). After blotting, the membrane was blocked at 4° C. for 10 h with 5% (w/v) milk powder diluted in TBS. The blot was then incubated at 37° C. for 1 h in the presence of the antibody. The membrane was washed five times for 5 min each with TBS and the blot was stained using the peroxidase substrate tetramethylbenzidine (Tiangen, China).

Capillary Electrophoresis

Capillary electrophoresis (CE), based on separation by charge-mass ratio, is used widely in the analysis of proteins and peptides. CE was performed on the P/ACE MDQ Capillary Electrophoresis System (Beckman Coulter, U.S.A.) equipped with a UV detector. A bare fused-silica capillary of 75 μm I.D. and 20 cm length was used for the separation. Phosphate buffer (40 mM NaPO$_4$, pH 11.0) was used as the electrophoresis buffer.

Figure 9:
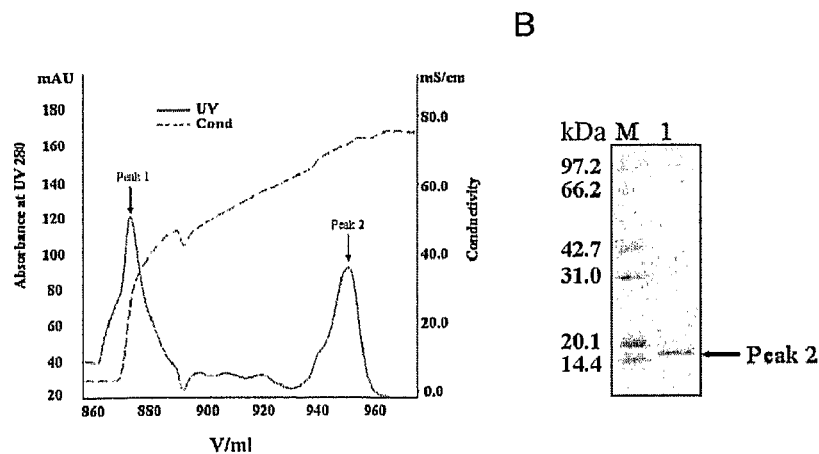
FIG. 9A shows the purification profile of rMuCXCL9 using an S-Sepharose column.
FIG. 9B shows SDS-PAGE analysis of Peak 2 from FIG. 9A. Lane M: molecular weight markers. Lane 1: eluted rMuCXCL9 protein.

Purification of rMuCXCL9 rMuCXCL9 has a basic pI value of 10.52. Cation exchange chromatography was chosen for purification with a buffer pH below 10.52. The protein binding conditions were optimized to be 20 mM NaPO$_4$, 1 mM EDTA, pH7.2 (Buffer A) according to batch absorption/elution experiments. Buffer A was used to equilibrate the column. After loading the refolded protein solution at a speed of 0.5 ml/min, the column was washed with Buffer A until the absorbance at 280 nm returned to baseline indicating removal of unbound proteins. The recombinant protein was then eluted by slowly increasing ionic strength of the buffer from 1M NaCl Buffer B. During the elution there were two protein peaks. The first one appeared when the conductivity reached 30 mS/cm (FIG. 9A, Peak 1), and the second one at conductivity of 75 mS/cm (FIG. 9A, Peak 2). Analyzing the eluted proteins by SDS-PAGE and protein staining, rMuCXCL9 was found to be eluted at Peak 2 (FIG. 9B).

SDS-PAGE and Capillary Electrophoretic Analysis of rMuCXCL9

Figure 10:
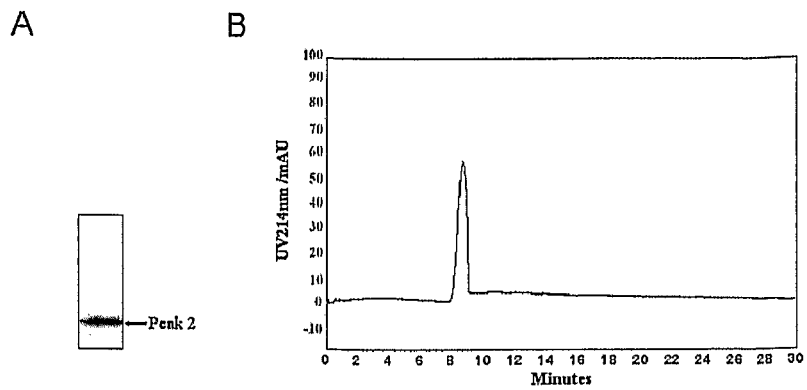
FIG. 10A shows the SDS-PAGE profile for 5 μg of Peak 2 rMuCXCL9.
FIG. 10B shows the capillary electrophoresis profile of Peak 2 rMuCXCL9. The single peak was observed after 9 min and the peak value was 60 mAU. The capillary electrophoresis was run using a bare fused-silica capillary with an effective length of 20 cm and 75 μm ID, with separation performed at 10 kV, detection at 214 nm, and using 40 mM phosphate buffer at pH 11.

To obtain the purity of the purified rMuCXCL9, the combined protein fractions from Peak 2 (FIG. 9A) were analyzed by SDS-PAGE and protein staining. 5 µg Peak 2 elute was loaded onto the gel. Except for the band corresponding to the predicted size of rMuCXCL9, no other bands could be visualized (FIG. 10A). As the protein staining sensitivity was 50 ng, the purity of rMuCXCL9 was estimated as >99%.

To further verify the purity of the purified rMuCXCL9, capillary electrophoresis (CE) was performed. The bare fused-silica capillary had affinity for negatively charged proteins, because the surface of the silica became positively charged when the buffer pH was over 3.0. The running buffer was adjusted to pH 11.0, which was slightly above the predicted pI (10.52) of rMuCXCL9 to make the protein negatively-charged. The purified rMuCXCL9 at 0.3 µg/µl was introduced by applying pressure at 0.5 psi for 5 sec. Electrophoresis was performed at constant voltage of 10 kV. During the CE running period, only one peak appeared at about 9 min with a measured value of 60 mAU (FIG. 110B). No other peaks were observed during the 30 min running period, demonstrating that no contaminant proteins were present in the final preparation of rMuCXCL9 (FIG. 10B).

The protein samples from each step were analyzed by SDS-PAGE and protein staining. The protein bands were scanned using B and Scan 5.0 software. The intensity of each band was recorded and transformed into digital data, and rMuCXCL9 purity from each purification step was calculated using the numbers of the protein signal densities. With increased purity, the rMuCXCL9 yield decreased stepwise along the purification steps. Each purification step contributed to the purification of rMuCXCL9. The final yield of rMuCXCL9 was 5.2% compared to the starting protein (Table 1).

TABLE 1

Purification of recombinant mouse CXCL9 using an *E. coli* expression system*

| Purification step | Total protein (mg) | rMuCXCL9 purity (%) | Total rMuCXCL9 (mg) | Protein yield (%) |
|---|---|---|---|---|
| Cell lysate by sonication | 390 | 40.7 | 158.7 | 100 |
| Denature with 8M urea | 80 | 66.6 | 53.3 | 33.6 |
| Renature by dilution | 40 | 90.0 | 36 | 22.7 |
| S-Sepharose eluate | 8.2 | 99.7 | 8.2 | 5.2 |

*Results are derived from 800 ml cultures of *E. coli* expressing the recombinant proteins.
*Total protein was estimated by the method of Bradford [17].

Biological Activity of rMuCXCL9 By Chemotaxis Assay

Chemotaxis assays were performed using a 24-well transwell chamber (6.5-mm diameter, 3-µm pore size, Costar 3415, Corning Costar), essentially as described by Gosling et al. [16]. Freshly isolated C57BL/6b mice spleen lymphocytes were suspended in IMEM cell culture medium (Invitrogen, USA) and the cell density was adjusted to $3 \times 10^6$ cells/ml. $3 \times 10^5$ cells in 100 µl were added to the top chamber, whereas 600 µl of IMEM with 10 nM-300 nM rMuCXCL9 was added to the bottom well. The chambers were then incubated for 3 h at 37° C. in an atmosphere containing 5% $CO_2$. Cells that passed through the membrane were harvested from the lower well and counted.

Figure 11:
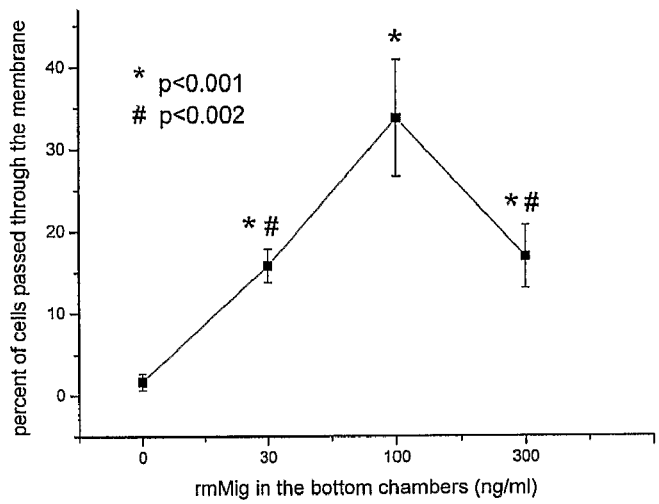
FIG. 11 shows the chemotaxis of rMuCXCL9 for mouse spleen lymphocytes.

Three concentrations of rMuCXCL9 (30 ng/ml, 10 ng/ml, 300 ng/ml) were tested with PBS as a negative control. rMuCXCL9 was added to the bottom chamber of the transwell system and the spleen cells placed in the upper chamber. Three hours after incubation, the cells that transmigrated through the transwell membrane were counted. At all three rMuCXCL9 concentrations, the number of cells that transmigrated through the transwell was significantly higher than that in the PBS control (FIG. 11, p<0.001). rMuCXCL9 at 100 ng/ml had the highest activity, and its calculated $ED_{50}$ was 30 ng/ml. These results demonstrated that the chemoattractant activity of rMuCXCL9 is concentration dependent (p<0.002).

Example 12

Expression and Purification of Recombinant Human CXCL9

A prokaryotic expression system and a one column purification strategy were used to obtain highly purified (>90%) rHuCXCL9.

Construction of the rHuCXCL9 Expression Vector

Figure 12:
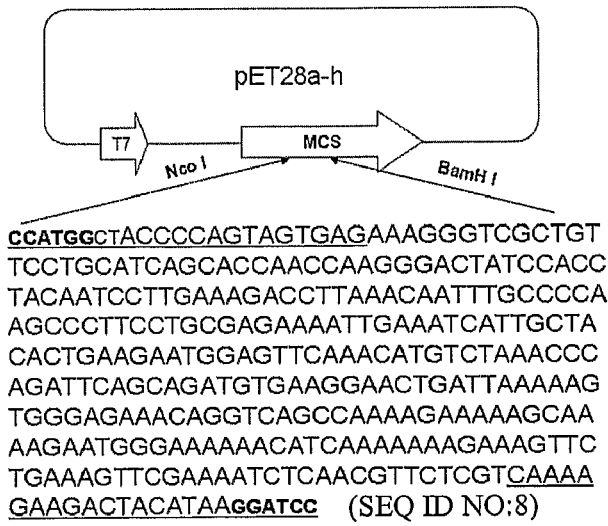
FIG. 12 shows a map of plasmid pET28a-h (SEQ ID NO:8). Underlined letters are primers and the forward primer contains a NcoI site and the extra 'CT' portion. The reverse primer contains a BamH I site and the natural stop codon 'TAA'.

The expression vector pET28a (+) and its host strain *E. coli* BL21 (DE3) were purchased from Novagen. RT-PCR kits and KOD plus were purchased from Toyoba Company (Japan). The CXCL9 cDNA was reverse transcribed from total RNA isolated from C57BL/6b mice bone marrow cells. The mature human CXCL9 cDNA covers the coding sequences of the gene from 106 bp to 417 bp (GB: NM_002416,) without the signal peptide coding sequences. PCR primers were designed according to that sequences and synthesized by Sangon (China). The forward primer contained an engineered NcoI site (underlined) 5'-CATG CCATGG CTACCCCAGTAGT-GAG-3' (SEQ ID NO:5), and the reverse primer was incorporated an engineered BamH I site (underlined) 5'-CGC GGATCC TTATGTAGTCTTCTTTTG-3' (SEQ ID NO:6). It used the natural stop codon of the gene (FIG. 12). To avoid the His-tag and T7-tag of the vector, the NcoI site was chosen to contain ATG translation start codon (FIG. 12). To construct the coding sequence of mature HuCXCL9 in frame with ATG, and connect to the extra G in the NcoI site, an extra amino acid Asp (A) was created by addition of CT to the 5' CXCL9 coding sequence.

After denaturation of DNA for 2 min at 94° C., amplification was performed for 35 cycles consisting of 20 sec at 94° C., 30 sec at 56° C., and 40 sec at 68° C. The purified PCR product and vector were digested with NcoI and BamH I (Fermentas, U.S.), gel-purified, and ligated together. *E. coli* DH5α was chemically transformed with the recombinant vector and cultured at 37° C. in LB agar with Kanamycin (100 μg/ml) for selection of recombinants. The recombinant plasmid containing accurate human CXCL9 gene was named pET28a-h (FIG. 12). It was further analyzed by restriction enzymatic pattern and finally confirmed by DNA sequencing (Invitrogen, China).

Expression of rHuCXCL9

Figure 13:
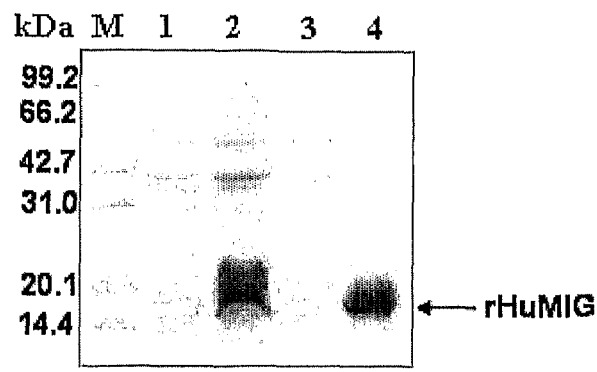
FIG. 13 shows the SDS-PAGE profile for fractions obtained from the expression of rHuCXCL9 in E. coli BL21. Lane M: molecular weight markers. Lane 1: uninduced E. coli cell lysate. Lane 2: IPTG-induced E. coli lysate. Lane 3: supernatant of induced E. coli lysate after sonication. Lane 4: pellet fraction of induced E. coli lysate after sonication.

*E. coli* BL21 (DE3) cells were transformed with the plasmid pET28a-h. A single transformed BL21 colony was inoculated into 3 ml LB medium supplemented with kanamycin (100 μg/ml) grown with 250 rpm shaking overnight at 37° C. 100 μl culture was transferred to 3 ml fresh LB medium in a 10 ml tube. The culture was grown with 250 rpm shaking at 37° C. until the OD600 reached 1.0 and then 3 μl of 500 mM IPTG was added for induction. 1 ml sample was collected at 3 h after induction. The pellet was resuspended in 50 μl of ddH$_2$O, mixed with 2×SDS loading buffer (0.09 M Tris-HCl, pH 6.8; 0.1 M DTT; 2% SDS; 20% glycerol; 0.02% bromphenol blue), and heated at 100° C. for 5 min. The sample was centrifuged at 10,000 g for 5 min and 10 μl supernatant was analyzed by 12% SDS-PAGE and stained with Coomassie brilliant blue R-250 solution. The expression of a protein corresponding to the predicted size of rHuCXCL9 was induced (FIG. 13, Lane 2).

After IPTG induction, the bacteria containing rMuCXCL9 were sonicated, soluble cell lysate (FIG. 13, Lane 4) and inclusion bodies (FIG. 13, Lane 5) were analyzed by SDS-PAGE and protein staining. The inclusion bodies were found to contain most of the rHuCXCL9, which represented 40% of the total proteins in the inclusion bodies measured by densitometry scanning of the stained gel.

Preparation of Inclusion Bodies 800 ml LB medium, supplemented with kanamycin (100 μg/ml), was inoculated with an overnight starter culture (OD600 of <0.1). Cultures were grown at 37° C. with 250 rpm shaking to OD600 of 0.8-1.0 and then induced with 1 mM IPTG (final concentration) for 3 h. Cells were harvested by centrifugation at 10,000 g for 15 min. Cell pellet was re-suspended in the lysis buffer (1×PBS, 1 mM EDTA, 0.1 mM PMSF) at a final concentration of 50 mg/ml and sonicated (SANYO soniprep 150, 15 bar; 30 s working and 30 s resting on ice for a cycle, 18 cycles). After centrifugation at 12,000 g for 15 min at 4° C., the undissolved inclusion bodies were collected and washed with the pellet wash buffer (0.5% Triton X-100, 10 mM EDTA, 50 mM NaCl) at 12,000 g for 5 min at 4° C., 5 times. The inclusion bodies were then solubilized in Buffer U (20 mM Na$_2$HPO$_4$, 1 mM EDTA, 50 mM NaCl, pH 9.0) containing 8 M urea at 9 ml Urea/g pellet, shaking slightly at 37° C. for 1 h. The insoluble pellets were removed by centrifugation at 15,000 g for 20 min at 4° C., and the dissolved inclusion bodies were ready for further purification.

Refolding and Purification of rHuCXCL9

The refolding was performed by dropwise dilution into defined protein folding buffer. The protein solution was dropped by pumping into 10-fold volume of Refolding Buffer (20 mM NaPO$_4$, 1 mM EDTA, pH 6.0), under vigorous (magnetic stirrer) agitation. pH of the solution was maintained at 6.0. Then an equal volume dilution Buffer (20 mM NaPO$_4$, 1 mM EDTA, pH 8.5) was added into the folding buffer. The refolded protein solution was set at 4° C. for about 24 h.

Figure 14:
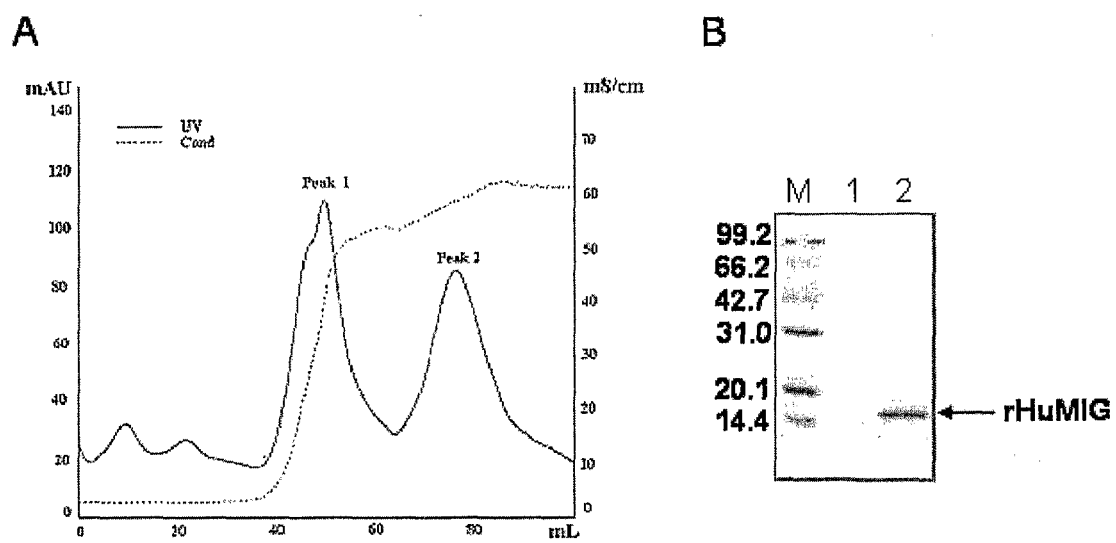
FIG. 14A shows the chromatographic purification of rHuCXCL9 on an S-Sepharose column.
FIG. 14B shows the SDS-PAGE profile of the purified rHuCXCL9 (Peak 2 from FIG. 14A).

The refolded protein solution was centrifuged at 18,000 g for 30 min. The collected supernatant was loaded on an S-Sepharose column with a volume of approximately 20 ml. The column was pre-equilibrated with Buffer A (20 mM NaPO$_4$, 1 mM EDTA, pH 7.2). The sample was loaded at speed of 0.5 ml/min, and the column was then washed with 2 column volumes of Buffer A. The column bound proteins were eluted using a programmed gradient of Buffer B (20 mM NaPO$_4$, 1 mM EDTA, 1 M NaCl, pH 7.2) at a speed of 3 ml/min.

rHuCXCL9 has a basic pI value of 10.33. Cation exchange chromatography was chosen for purification with buffer pH below 10.33. The protein binding conditions were optimized to be 20 mM NaPO$_4$, 1 mM EDTA, pH 7.2 (Buffer A) according to batch absorption/elution experiments. Buffer A was used to equilibrate the column. After loading the refolded protein solution at a speed of 0.5 ml/min, the column was washed with Buffer A until the absorbance at 280 nm returned to baseline indicating removal of unbound proteins. The recombinant protein was then eluted by slowly increasing ionic strength of the buffer from 1M NaCl Buffer B. During the elution there were two protein peaks. The first one appeared when the conductivity reached 45 mS/cm (FIG. 14A, Peak 1), and the second one at conductivity of 60 mS/cm (FIG. 14A, Peak 2). Analyzing the eluted proteins by SDS-PAGE and protein staining, rHuCXCL9 was found to be eluted at Peak 2 (FIG. 14B). From lane 2 of FIG. 14B, the purity of the rHuCXCL9 fraction was above 90%.

REFERENCES

[1]. Farber, J. M. 1990. A macrophage mRNA selectively induced by gamma-interferon encodes a member of the platelet factor 4 family of cytokines. Proc. Natl. Acad. Sci. U.S. 87:5238-5242.

[2]. Rollins, B. J. 1997. Chemokines. Blood 90:909-928.

[3]. Liao, F., R. L. Rabin, J. R. Yannelli, L. G. Koniaris, P. Vanguri, and J. M. Farber. 1995. Human CXCL9 chemokine: biochemical and functional characterization. J Exp Med 182: 1301-1314.

[4]. Gasperini, S., M. Marchi, F. Calzetti, C. Laudanna, L. Vicentini, H. Olsen, M. Murphy, F. Liao, J. Farber, and M. A. Cassatella. 1999. Gene expression and production of the monokine induced by IFN-gamma (CXCL9), IFN-inducible T cell alpha chemoattractant (I-TAC), and IFN-gamma-inducible protein-10 (IP-10) chemokines by human neutrophils. J Immunol 162:4928-4937.

[5]. Broxmeyer, H. E., C. H. Kim, S. H. Cooper, G. Hangoc, R. Hromas, and L. M. Pelus. 1999. Effects of CC, CXC, C, and CX3C chemokines on proliferation of myeloid progenitor cells, and insights into SDF-1-induced chemotaxis of progenitors. Ann. N.Y. Acad. Sci. 872:142-162; discussion 163.

[6]. Loos, T., L. Dekeyzer, S. Struyf, E. Schutyser, K. Gijsbers, M. Gouwy, A. Fraeyman, W. Put, I. Ronsse, B. Grillet, G. Opdenakker, J. V. Damme, and P. Proost. 2006. TLR ligands and cytokines induce CXCR3 ligands in endothelial cells: enhanced CXCL9 in autoimmune arthritis. Lab Invest 86:902-916.

[7]. Yun, J. J., M. P. Fischbein, D. Whiting, Y. Irie, M. C. Fishbein, M. D. Burdick, J. Belperio, R. M. Strieter, H. Laks, J. A. Berliner, and A. Ardehali. 2002. The role of CXCL9/CXCL9 in cardiac allograft vasculopathy. Am. J. Pathol. 161: 1307-1313.

[8]. Zhang, R., L. Tian, L. J. Chen, F. Xiao, J. M. Hou, X. Zhao, G. Li, B. Yao, Y. J. Wen, J. Li, L. Zhang, X. C. Chen, F. Luo, F. Peng, Y. Jiang, and Y. Q. Wei. 2006. Combination of CXCL9 (CXCL9) chemokine gene therapy with low-dose cisplatin improves therapeutic efficacy against murine carcinoma. Gene Ther 13:1263-1271.

[9]. Schwartz, G. N., F. Liao, R. E. Gress, and J. M. Farber. 1997. Suppressive effects of recombinant human monokine induced by IFN-gamma (rHuCXCL9) chemokine on the number of committed and primitive hematopoietic progenitors in liquid cultures of CD34+ human bone marrow cells. J Immunol 159:895-904.

[10]. Ruehlmann, J. M., R. Xiang, A. G. Niethammer, Y. Ba, U. Pertl, C. S. Dolman, S. D. Gillies, and R. A. Reisfeld. 2001. CXCL9 (CXCL9) chemokine gene therapy combines with antibody-cytokine fusion protein to suppress growth and dissemination of murine colon carcinoma. Cancer Res 61:8498-8503.

[11]. Lazzeri, E., and P. Romagnani. 2005. CXCR3-binding chemokines: novel multifunctional therapeutic targets. Curr Drug Targets Immune Endocr. Metabol. Disord. 5:109-118.

[12]. Jinquan, T., S. Quan, H. H. Jacobi, C. Jing, A. Millner, B. Jensen, H. O. Madsen, L. P. Ryder, A. Svejgaard, H. J. Malling, P. S. Skov, and L. K. Poulsen. 2000. CXC chemokine receptor 3 expression on CD34(+) hematopoietic progenitors from human cord blood induced by granulocyte-macrophage colony-stimulating factor: chemotaxis and adhesion induced by its ligands, interferon gamma-inducible protein 10 and monokine induced by interferon gamma. Blood 96:1230-1238.

[13]. Nicolini, A., A. Carpi, and G. Rossi. 2006. Cytokines in breast cancer. Cytokine Growth Factor Rev 17:325-337.

[14]. Gomez Raposo, C., A. Pinto Marin, and M. Gonzalez Baron. 2006. Colony-stimulating factors: clinical evidence for treatment and prophylaxis of chemotherapy-induced febrile neutropenia. Clin. Transl. Oncol. 8:729-734.

[15]. Fernandez-Varon, E., and L. Villamayor. 2006. Granulocyte and granulocyte macrophage colony-stimulating factors as therapy in human and veterinary medicine. Vet J.

[16]. Gosling, J., F. S. Monteclaro, R. E. Atchison, H. Arai, C. L. Tsou, M. A. Goldsmith, and I. F. Charo, Molecular uncoupling of C—C chemokine receptor 5-induced chemotaxis and signal transduction from HIV-1 coreceptor activity, Proc Natl Acad Sci USA 94 (1997) 5061-5066.

[17]. Marion. M, Bradford, A rapid and sensitive method for the quantitation of microgram quantities of protein utilizing the principle of protein-dye binding, Anal. Biochem 72 (1976) 248-254.

[18]. Zhang, D. X., J. Wu, J. H. Yang, and D. M. Fan, Large scale production and purification of murine chemokine monokine induced by IFN-gamma (MIG, CXCL9) in insect cells and its angiostatic effects, Progress in Biochemistry and Biophysics 32 (2005) 975-981.

[19]. Tobias, J. W., T. E. Shrader, G. Rocap, and A. Varshavsky, The N-end rule in bacteria, Science 254 (1991) 1374-1377.

[20]. Varshavsky, A. The N-end rule pathway of protein degradation, Genes Cells 2 (1997) 13-28.

The disclosures of each and every patent, patent application, and publication cited herein are hereby incorporated herein by reference in their entirety. While the invention has been described in connection with specific methods and compositions, those skilled in the art will recognize other equivalents to the specific aspects herein. It is to be understood that the description is by way of example and not as a limitation to the scope of the invention and these equivalents are intended to be encompassed by the claims set forth below.

What is claimed is:

1. A method of preventing bone marrow cell damage resulting from chemotherapy or radiotherapy, the method comprising: administering an effective amount of a CXCR3 agonist, wherein the CXCR3 agonist is selected from the group consisting of CXCL9 (Mig), I-TAC, and IP-10, to a subject prior to administering chemotherapy or radiotherapy to the subject, wherein following chemotherapy or radiotherapy the bone marrow cell density or the level of peripheral white blood cells of the subject is increased compared to a control subject not receiving the CXCR3 agonist.

2. The method of claim 1, wherein the CXCR3 agonist is administered for two or more days prior to administering the chemotherapy or the radiotherapy.

3. The method of claim 1, further comprising administering an additional myelosuppressive agent to the subject prior to the chemotherapy or the radiotherapy.

4. The method of claim 3, wherein the myelosuppressive agent is CCL3.

5. The method of claim 1, further comprising administering to the subject an effective amount of a CXCR3 antagonist following the chemotherapy or radiotherapy, wherein the CXCR3 antagonist is an anti-CXCL9 antibody.

6. The method of claim 5, wherein the CXCR3 antagonist is administered in daily doses for two or more days following the administration of the chemotherapy or the radiotherapy.

7. The method of claim 5, further comprising administering a hematopoietic growth factor to the subject following the chemotherapy or the radiotherapy.

8. The method of claim 7, wherein the growth factor is GM-CSF or G-CSF.

9. The method of claim 1, wherein the chemotherapy is cell cycle specific.

10. The method of claim 9, wherein the cell cycle specific chemotherapy is selected from the group consisting of 5-fluorouracil, Ara-C, vinblastine, and methotrexate.

11. The method of claim 1, wherein the chemotherapy is cell cycle non-specific.

12. The method of claim 11, wherein the cell cycle non-specific chemotherapy is selected from the group consisting of cyclophosphamide, doxorubicin, cisplatin, and busulfan.

13. The method of claim 1, wherein the radiotherapy comprises administering external beam radiation or a radiopharmaceutical agent.

14. The method of claim 1, wherein the subject is human.

15. A method of enhancing the effectiveness of chemotherapy or radiotherapy to treat cancer, the method comprising administering to a subject with cancer an effective amount of a CXCR3 agonist, wherein the CXCR3 agonist is selected from the group consisting of CXCL9 (Mig), I-TAC, and IP-10, prior to administering chemotherapy or radiotherapy at a higher dose than would be administered in the absence of the administration of the CXCR3 agonist, wherein the effectiveness of the chemotherapy or radiotherapy is enhanced.

* * * * *

SEQUENCE LISTING

<160> NUMBER OF SEQ ID NOS: 11

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccgctcgagc caccatgaag tccgctgttc ttttcc                            36

<210> SEQ ID NO 2
<211> LENGTH: 29
<212> TYPE: DNA
<213> ORGANISM: Artificial Sequence
<220> FEATURE:
<223> OTHER INFORMATION: Description of Artifiical Sequence: Synthetic
      primer

<400> SEQUENCE: 2
cggaattctt gtagtcttcc ttgaacgac                                    29

<210> SEQ ID NO 3
<211> LENGTH: 27
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 3
catgccatgg acaccctagt gataagg                                               27

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
ccgctcgagt tatgtagtct tccttgaacg                                            30

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
catgccatgg ctaccccagt agtgag                                                26

<210> SEQ ID NO 6
<211> LENGTH: 27
<212> TYPE: DNA
<213> ORGANISM: Artificial Sequence
<220> FEATURE:
<223> OTHER INFORMATION: Description of Artifiical Sequence: Synthetic
      primer

<400> SEQUENCE: 6
cgcggatcct tatgtagtct tcttttg                                               27

<210> SEQ ID NO 7
<211> LENGTH: 361
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 7
ccatggacac cctagtgata aggaatgcac gatgctcctg catcagcacc agccgaggca           60
cgatccacta caaatccctc aaagacctca aacagtttgc cccaagcccc aattgcaaca         120
aaactgaaat cattgctaca ctgaagaacg gagatcaaat cattgctaca ctgaagaacg         180
gagatcaaac ctgcctagat ccggactcgg caaatgtgaa gaagctgatg aaagaatggg         240
aaaagaagat caaccaaaag aaaaagcaaa agaggggaaa aaaacataaa agaacatgaa         300
aaacagaaaa cccaaaacac cccaaagtcg tcgtcgttca aggaagacta cataactcga         360
g                                                                         361

<210> SEQ ID NO 8
<211> LENGTH: 326
<212> TYPE: DNA
<213> ORGANISM: Artificial Sequence
<220> FEATURE:
<223> OTHER INFORMATION: Description of Artificial Sequence: Synthetic
      construct
```

```
<400> SEQUENCE: 8
ccatggctac cccagtagtg agaaagggtc gctgttcctg catcagcacc aaccaaggga      60
ctatccacct acaatccttg aaagacctta acaatttgc cccaagccct tcctgcgaga      120
aaattgaaat cattgctaca ctgaagaatg gagttcaaac atgtctaaac ccagattcag     180
cagatgtgaa ggaactgatt aaaaagtggg agaaacaggt cagccaaaag aaaaagcaaa     240
agaatgggaa aaacatcaa aaaagaaag ttctgaaagt tcgaaaatct caacgttctc      300
gtcaaaagaa gactacataa ggatcc                                         326

<210> SEQ ID NO 9
<211> LENGTH: 2636
<212> TYPE: DNA
<213> ORGANISM: Mus musculus

<400> SEQUENCE: 9
gaaagacatt ctcggacttc actccaacac agtgactcaa tagaactcag ctctgccatg     60
aagtccgctg ttcttttcct cttgggcatc atcttcctgg agcagtgtgg agttcgagga    120
accctagtga taaggaatgc acgatgctcc tgcatcagca ccagccgagg cacgatccac    180
tacaaatccc tcaaagacct caaacagttt gccccaagcc ccaattgcaa caaaactgaa    240
atcattgcta cactgaagaa cggagatcaa acctgcctag atccggactc ggcaaatgtg    300
aagaagctga tgaaagaatg ggaaaagaag atcagccaaa agaaaaagca aagaggggg    360 aaaaaacatc aaaagaacat gaaaaacaga aacccaaaa caccccaaag tcgtcgtcgt    420
tcaaggaaga ctacataaga gaccattact ttaccaacaa gcaccctgaa tcttaatggg    480
ttttagattg tactgaaaag ccttcctggt cagagcagcc tttaatacat aggcttttaa    540
tacattaact caactacaaa acataaagtg ttaatttgaa attataacta actttaggaa    600
gttaattgca aaactccaat agtaacaatt gctagaggca aaaactctgt gttctacaca    660
gccaacaaaa tttcatcacg cccttgagcc tagtcgtgat aacatcagat ctgggcaagt    720 gtcccttttcc ttcatagcta tccaatgcac aacagctgtc tggcttccag agccacacat    780
ttggcagcct ccgaagactt ctgaggctca cgtcaccaaa tcccaggcct gtctgtttgc    840
tggtgagcta gatagacctc accaagctgg agaggccctc ggccagctgc atttgggtca    900
gcctagagcc cctgcacaca ttgtgtctca gagatggtgc taatggtttt ggggttctac    960
agtggagacc accagagttg gccttcgaa cctcccacgt agctttcgag accatgggat   1020
ttcattatta acttgatccc atcttcagag cttattctaa gtttgcctct tcaataaaac   1080
tctcctagaa ggttgtggct gtagcttagt ggcagaacac ttggtgttgc agggaccagg   1140
tccttcacta acagtgcaaa aacttaacca atttaaagaa catttctgg ctactcaaat   1200 tctcttaaat ttattcctgt ttcacaagta aacacttcgc tgctatctaa ttggatttgt   1260
ttgtttgttt gttttacttt ttccaacgag acgggttttt aagagtaggg accacagact   1320
attcccctaa atcttccaca gtgcctacaa aaacttggtt ttgaataatt tcctaattgt   1380
atgtgtgaga ggtagaaagg ctgttacaca ccaggcattg ccaatcccc ggctgctcca   1440 aattgcctaa ctaacctttg gcctccttgc ttgcttacca ctttttttt ttttttttt   1500 aaagaaagtt ttatatctgg ctgtcctaaa actctcaaag tagacaaggc tggtctcaaa   1560
ttcatacata tctgtattct actgcctcct gaatgctggg gttaaaggtg tgtgctacta   1620
cacctgattg cctgccttcc ttcctttctc cctccctccc ttccttcctt ccttccttcc   1680
ttccttcctt ccttccttcc ttccttcctt ccttaaatta tctagctttc ttattatctt   1740
```

| | |
|---|---:|
| cagacatctt cagcgcacag agccagacag ggtgaaaaag agccttacct tgtgacagga | 1800 |
| ggctcgtgtc tttaacaaac aggaatcaca tgttcaagac atttgcggat atttgggact | 1860 |
| gctcaggaaa aattacacag gccatctaga aacataagct tacatggaag acaggtttga | 1920 |
| ctgattggca aatactagat cttcctcac tcaaaacaaa attcctctaa tatcattctt | 1980 |
| gatcaggaca agctccctag gagtcaacaa aagagctgcc aaatccttta gcaagtttat | 2040 |
| cttaggtgaa tatgaatttc cttgccacct tccctccctc attgcagaaa tcccagtgta | 2100 |
| tgattgtatg gattgccaca tcaggctagg agtggtgaaa tggaaagatc agggctggag | 2160 |
| agggagccag agttccattc ccagcaccca cccccacgtg tgcgtgagcc ttgtggccac | 2220 |
| ctgtgactcc agctccaggg aacccatttc tctcttctgg cctctgcaag cattgcacag | 2280 |
| gtgtacacag gcccccatga catacaccca taatctcaga cggcaaataa aaatctttac | 2340 |
| agagatattt ttaaaggaat taagagctac aggaagcagt aaattctgcg agtggaagtg | 2400 |
| tggacagggc caagttagcc tgtgtgggag ctggaaactg ctctagagag gaggtctgat | 2460 |
| gaattagata gaaaagaatg tctctgggca gaagttccgt cttgagcatg cttttctca | 2520 |
| aatactgcca ttcctggcgc tgcatgcagg tggttttgt gctgctggtg ggactcccat | 2580 |
| ccaaacaaca ttgcacagtc aaaacgttgt ccacctccct tcggtaattt actttg | 2636 |

<210> SEQ ID NO 10
<211> LENGTH: 2545
<212> TYPE: DNA
<213> ORGANISM: Homo sapiens
<400> SEQUENCE: 10

| | |
|---|---:|
| atccaataca ggagtgactt ggaactccat tctatcacta tgaagaaaag tggtgttctt | 60 |
| ttcctcttgg gcatcatctt gctggttctg attggagtgc aaggaacccc agtagtgaga | 120 |
| aagggtcgct gttcctgcat cagcaccaac caagggacta ccacctaca atccttgaaa | 180 |
| gaccttaaac aatttgcccc aagcccttcc tgcgagaaaa ttgaaatcat tgctacactg | 240 |
| aagaatggag ttcaaacatg tctaaaccca gattcagcag atgtgaagga actgattaaa | 300 |
| aagtgggaga acaggtcag ccaaaagaaa aagcaaaaga tgggaaaaa acatcaaaaa | 360 |
| aagaaagttc tgaaagttcg aaaatctcaa cgttctcgtc aaaagaagac tacataagag | 420 |
| accacttcac caataagtat tctgtgttaa aaatgttcta tttttaattat accgctatca | 480 |
| ttccaaagga ggatggcata taatacaaag gcttattaat ttgactagaa aatttaaaac | 540 |
| attactctga aattgtaact aaagttagaa agttgatttt aagaatccaa acgttaagaa | 600 |
| ttgttaaagg ctatgattgt ctttgttctt ctaccacca ccagttgaat ttcatcatgc | 660 |
| ttaaggccat gattttagca atacccatgt ctacacagat gttcacccaa ccacatccca | 720 |
| ctcacaacag ctgcctggaa gagcagccct aggcttccac gtactgcagc ctccagagag | 780 |
| tatctgaggc acatgtcagc aagtcctaag cctgttagca tgctggtgag ccaagcagtt | 840 |
| tgaaattgag ctggacctca ccaagctgct gtggccatca acctctgtat ttgaatcagc | 900 |
| ctacaggcct cacacacaat gtgtctgaga gattcatgct gattgttatt gggtatcacc | 960 |
| actggagatc accagtgtgt ggctttcaga gcctcctttc tggctttgga agccatgtga | 1020 |
| ttccatcttg cccgctcagg ctgaccactt tatttctttt tgttcccctt tgcttcattc | 1080 |
| aagtcagctc ttctccatcc taccacaatg cagtgccttt cttctctcca gtgcacctgt | 1140 |
| catatgctct gatttatctg agtcaactcc tttctcatct tgtccccaac accccacaga | 1200 |
| agtgctttct tctcccaatt catcctcact cagtccagct tagttcaagt cctgcctctt | 1260 |

```
aaataaacct ttttggacac acaaattatc ttaaaactcc tgtttcactt ggttcagtac    1320
cacatgggtg aacactcaat ggttaactaa ttcttgggtg tttatcctat ctctccaacc    1380
agattgtcag ctccttgagg gcaagagcca cagtatattt ccctgtttct tccacagtgc    1440
ctaataatac tgtggaacta ggttttaata atttttttaat tgatgttgtt atgggcagga    1500
tggcaaccag accattgtct cagagcaggt gctggctctt tcctggctac tccatgttgg    1560
ctagcctctg gtaacctctt acttattatc ttcaggacac tcactacagg gaccagggat    1620
gatgcaacat ccttgtcttt ttatgacagg atgtttgctc agcttctcca acaataagaa    1680
gcacgtggta aaacacttgc ggatattctg gactgttttt aaaaaatata cagtttaccg    1740
aaaatcatat aatcttacaa tgaaaaggac tttatagatc agccagtgac caaccttttc    1800
ccaaccatac aaaaattcct tttcccgaag gaaaagggct ttctcaataa gcctcagctt    1860
tctaagatct aacaagatag ccaccgagat ccttatcgaa actcatttta ggcaaatatg    1920
agttttattg tccgtttact tgtttcagag tttgtattgt gattatcaat taccacacca    1980
tctcccatga agaagggaa cggtgaagta ctaagcgcta gaggaagcag ccaagtcggt    2040
tagtggaagc atgattggtg cccagttagc ctctgcagga tgtggaaacc tccttccagg    2100
ggaggttcag tgaattgtgt aggagaggtt gtctgtggcc agaatttaaa cctatactca    2160
ctttcccaaa ttgaatcact gctcacactg ctgatgattt agagtgctgt ccggtggaga    2220
tcccacccga acgtcttatc taatcatgaa actccctagt tccttcatgt aacttccctg    2280
aaaaatctaa gtgtttcata aatttgagag tctgtgaccc acttaccttg catctcacag    2340
gtagacagta taactaac aaccaaagac tacatattgt cactgacaca cacgttataa    2400
tcatttatca tatatataca tacatgcata cactctcaaa gcaaataatt tttcacttca    2460
aaacagtatt gacttgtata ccttgtaatt tgaaatattt tctttgttaa aatagaatgg    2520
tatcaataaa tagaccatta atcag                                          2545

<210> SEQ ID NO 11
<211> LENGTH: 1630
<212> TYPE: DNA
<213> ORGANISM: Homo sapiens

<400> SEQUENCE: 11
ccaaccacaa gcaccaaagc agagggggcag gcagcacacc acccagcagc cagagcacca     60
gcccagccat ggtccttgag gtgagtgacc accaagtgct aaatgacgcc gaggttgccg    120
ccctcctgga gaacttcagc tcttcctatg actatggaga aaacgagagt gactcgtgct    180
gtacctcccc gccctgccca caggacttca gcctgaactt cgaccgggcc ttcctgccag    240
ccctctacag cctcctctttt ctgctggggc tgctgggcaa cggcgcggtg gcagccgtgc    300
tgctgagccg gcggacagcc ctgagcagca ccgacacctt cctgctccac ctagctgtag    360
cagacacgct gctggtgctg acactgccgc tctgggcagt ggacgctgcc gtccagtggg    420
tctttggctc tggcctctgc aaagtggcag gtgccctctt caacatcaac ttctacgcag    480 gagcccctcct gctggcctgc atcagctttg accgctacct gaacatagtt catgccaccc    540
agctctaccg ccggggggccc ccggcccgcg tgaccctcac ctgcctggct gtctggggc    600 tctgcctgct tttcgccctc ccagacttca tcttcctgtc ggcccaccac gacgagcgcc    660
tcaacgccac ccactgccaa tacaacttcc cacaggtggg ccgcacggct ctgcgggtgc    720
tgcagctggt ggctggcttt ctgctgcccc tgctggtcat ggcctactgc tatgcccaca    780
tcctggccgt gctgctggtt ccaggggcc agcggcgcct gcgggccatg cggctggtgg    840
```

```
tggtggtcgt ggtggcettt gccctctgct ggaccccta tcacctggtg gtgctggtgg      900
acatcctcat ggacctgggc gctttggccc gcaactgtgg ccgagaaagc agggtagacg     960
tggccaagtc ggtcacctca ggcctgggct acatgcactg ctgcctcaac ccgctgctct    1020
atgcctttgt aggggtcaag ttccgggagc ggatgtggat gctgctcttg cgcctgggct    1080
gccccaacca gagagggctc cagaggcagc catcgtcttc ccgccgggat tcatcctggt    1140
ctgagacctc agaggcctcc tactcgggct tgtgaggccg gaatccgggc tcccctttcg    1200
cccacagtct gacttccccg cattccaggc tcctccctcc ctctgccggc tctggctctc    1260
cccaatatcc tcgctcccgg gactcactgg cagcccagc accaccaggt ctcccgggaa     1320
gccaccctcc cagctctgag gactgcacca ttgctgctcc ttagctgcca agccccatcc    1380
tgccgcccga ggtggctgcc tggagcccca ctgcccttct catttggaaa ctaaaacttc    1440
atcttcccca agtgcgggga gtacaaggca tggcgtagag ggtgctgccc catgaagcca    1500
cagcccaggc ctccagctca gcagtgactg tggccatggt ccccaagacc tctatatttg    1560
ctcttttatt tttatgtcta aaatcctgct taaaactttt caataaacaa gatcgtcagg    1620
accaaaaaaa                                                            1630
```